(12) United States Patent
Butler et al.

(10) Patent No.: US 11,216,947 B2
(45) Date of Patent: Jan. 4, 2022

(54) MATERIAL IDENTIFICATION USING MULTI-ENERGY CT IMAGE DATA

(71) Applicant: MARS BIOIMAGING LIMITED, Christchurch (NZ)

(72) Inventors: Anthony Philip Howard Butler, Christchurch (NZ); Christopher James Bateman, Christchurch (NZ); Philip Howard Butler, Christchurch (NZ); Peter Francis Renaud, Christchurch (NZ)

(73) Assignee: MARS BIOIMAGING LIMITED, Christchurch (NZ)

( * ) Notice: Subject to any disclaimer, the term of this patent is extended or adjusted under 35 U.S.C. 154(b) by 86 days.

(21) Appl. No.: 16/844,018

(22) Filed: Apr. 9, 2020

(65) Prior Publication Data

US 2020/0242761 A1 Jul. 30, 2020

Related U.S. Application Data

(62) Division of application No. 15/567,623, filed as application No. PCT/NZ2016/050064 on Apr. 20, 2015, now Pat. No. 10,685,437.

(30) Foreign Application Priority Data

Apr. 20, 2015 (NZ) ........................ 707176

(51) Int. Cl.
*G06T 7/00* (2017.01)
*A61B 6/03* (2006.01)
(Continued)

(52) U.S. Cl.
CPC ............ *G06T 7/0012* (2013.01); *A61B 6/032* (2013.01); *A61B 6/482* (2013.01); *A61B 6/505* (2013.01);
(Continued)

(58) Field of Classification Search
CPC ......... G06T 7/0012; G06T 5/002; G06T 5/20; G06T 11/008; G06T 2200/04;
(Continued)

(56) References Cited

U.S. PATENT DOCUMENTS

2005/0068317 A1* 3/2005 Amakai ................ G06T 7/001
345/419
2006/0079746 A1* 4/2006 Perret ................ A61B 5/02007
600/407

(Continued)

*Primary Examiner* — Ali Bayat
(74) *Attorney, Agent, or Firm* — Taft Stettinius & Hollister LLP; Ryan O. White; Derek B. Lavender

(57) ABSTRACT

Disclosed are methods for identification and quantification of a number of different materials within an object using one or more multi-energy CT imaging devices and the image data sets produced therefrom. Identification and quantification of different materials is achieved by using the following three properties: solve only for sparse solutions; separate the soft tissue problem from the dense material problem; and use a combinatorial approach to allow for simple application of different constraints to different combinations of materials. Also disclosed are one or more computer program products, computer systems or computer implemented methods for the identification of multiple materials within an object.

21 Claims, 31 Drawing Sheets

(a)

(b)

(51) Int. Cl.
*A61B 6/00* (2006.01)
*G01N 23/046* (2018.01)
*G06K 9/40* (2006.01)
*G06K 9/62* (2006.01)
*G06T 5/00* (2006.01)
*G06T 5/20* (2006.01)
*G06T 11/00* (2006.01)

(52) U.S. Cl.
CPC ............. *G01N 23/046* (2013.01); *G06K 9/40* (2013.01); *G06K 9/6202* (2013.01); *G06K 9/6267* (2013.01); *G06T 5/002* (2013.01); *G06T 5/20* (2013.01); *G06T 11/008* (2013.01); *G06T 2200/04* (2013.01); *G06T 2207/10081* (2013.01); *G06T 2207/20032* (2013.01); *G06T 2207/30008* (2013.01); *G06T 2207/30052* (2013.01)

(58) Field of Classification Search
CPC . G06T 2207/10081; G06T 2207/20032; G06T 2207/30008; G06T 2207/30052; A61B 6/482; A61B 6/505; A61B 6/032; G01N 23/046; G06K 9/40; G06K 9/6202; G06K 9/6267
USPC .......................................................... 382/131
See application file for complete search history.

(56) References Cited

U.S. PATENT DOCUMENTS

| | | | | |
|---|---|---|---|---|
| 2009/0304248 | A1* | 12/2009 | Zalis | ...................... G06T 7/155 |
| | | | | 382/131 |
| 2010/0054563 | A1* | 3/2010 | Mendonca | ............. A61B 6/037 |
| | | | | 382/131 |
| 2010/0329529 | A1* | 12/2010 | Feldman | .............. G06K 9/4619 |
| | | | | 382/131 |
| 2015/0003706 | A1* | 1/2015 | Eftestol | ..................... G06T 7/40 |
| | | | | 382/131 |
| 2015/0078641 | A1* | 3/2015 | Tan | ........................... G06T 7/12 |
| | | | | 382/131 |
| 2017/0358078 | A1* | 12/2017 | Hoff | ......................... G06T 7/11 |
| 2018/0005417 | A1* | 1/2018 | Schieke | .................... G06T 7/30 |

* cited by examiner (a) Water
(b) Lipid
(c) Adipose
(d) Brain
(e) Skeletal Muscle
(f) Lung Tissue
(g) Blood
(h) Cortical Bone Iohexol
(i) 50mg(I)/ml
(j) 100mg(I)/ml
(k) 150mg(I)/ml
(l) 200mg(I)/ml Gadodiamide
(m) 50mg(Gd)/ml
(n) 100mg(Gd)/ml
(o) 150mg(Gd)/ml
(p) 200mg(Gd)/ml

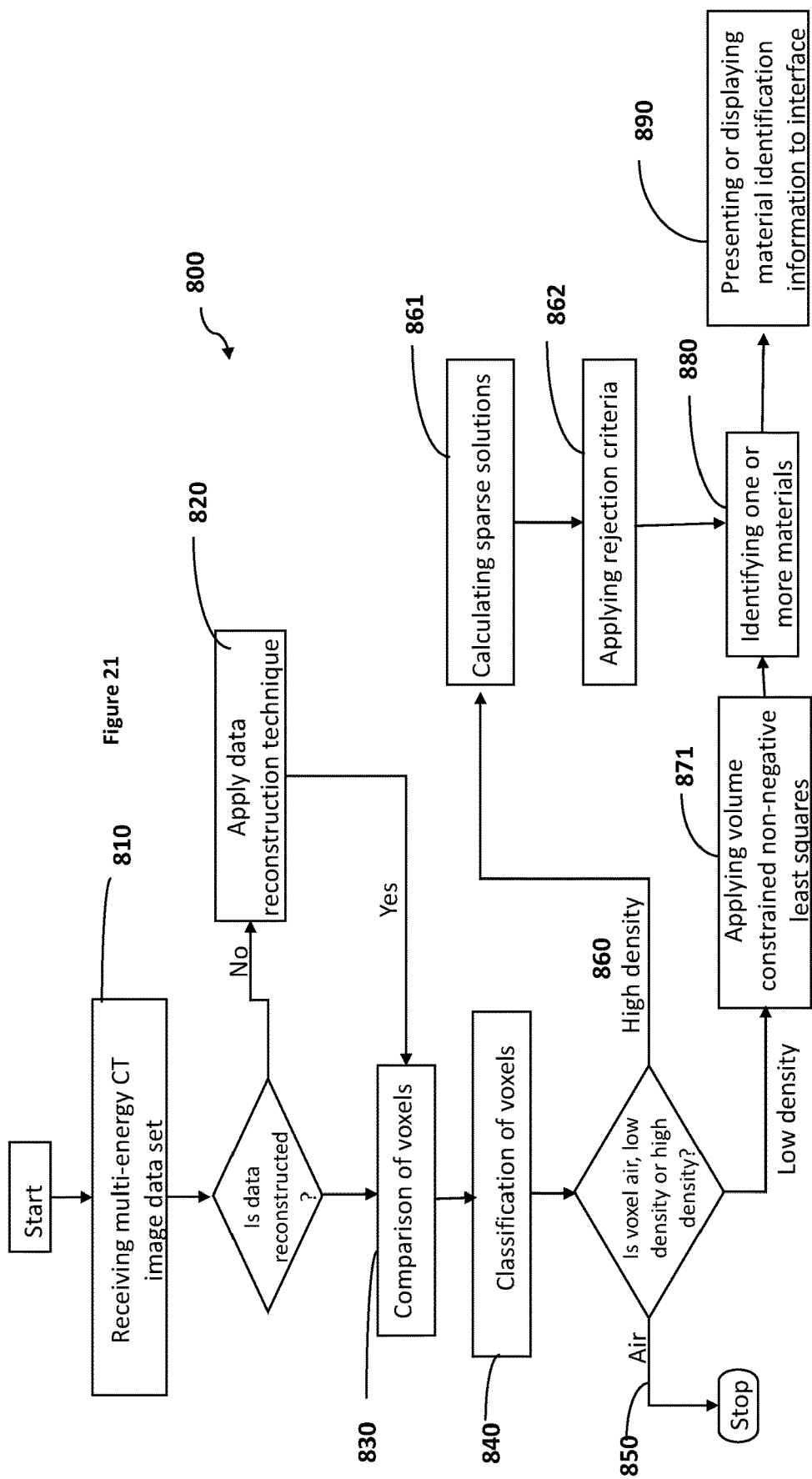

MATERIAL IDENTIFICATION USING MULTI-ENERGY CT IMAGE DATA

INCORPORATION BY REFERENCE

This application is a divisional of U.S. application Ser. No. 15/567,623 filed on Oct. 19, 2017 which is a U.S. National Phase of International PCT Application No. PCT/NZ2016/050064 filed on Apr. 20, 2016, which claims priority to NZ Application No. 707176 filed on Apr. 20, 2015, the contents of each application are herein incorporated by reference in their entirety.

FIELD OF INVENTION

This invention relates to the use of multi-energy computed tomography (CT) to identify and to quantify different materials within an object. More specifically, methods for processing multi-energy CT images are discussed, with reference to different applications.

BACKGROUND TO THE INVENTION

Multi-energy computed tomography (CT) is an x-ray imaging modality which produces 3D images of the inside of objects. CT scanners use polychromatic x-ray sources which emit a full rainbow of x-rays with various colours (x-ray energies). In regular CT there is no distinction made between the different energies of x-rays. However x-rays are absorbed differently by different materials in the body, and differently again for x-rays of different energies. Multi-energy CT measures the absorption of x-rays in different energy ranges. Using the differences in x-ray absorption in these energy ranges it is possible to discriminate between (identify) and quantify various materials in an object.

A major role of material analysis algorithms in multi-energy CT is to assign to each voxel in the reconstructed CT image the quantity of one or more materials from a dictionary of possible materials which may be present. This poses a significant problem as many of the materials that one would include in this dictionary have very similar x-ray attenuation properties. When the dictionary has a large number of similar materials then the inversion techniques used for material analysis algorithms are numerically unstable—producing nonsensical results.

Another common problem faced by all material detection and quantification algorithms is the incorrect identification of one material as another. There are three types of material misidentification which are typically encountered. The first type results from numerical instability when decomposing into a basis containing a large number of materials. Large material basis sets are ill-conditioned due to the similarities in attenuation between different materials. The second type results from omitting materials from the decomposition to achieve a more stable inversion. This however will project non-represented materials onto the given basis, describing them as a combination of different materials. The third type occurs when material decomposition is done on poor quality data with significant image artefacts such as excessive noise.

The problems above have made it difficult to identify and quantify large numbers of different materials within a multi-energy CT scan. Known material decomposition methods have achieved the discrimination of four different materials (excluding air) or five (including air) using multi-energy CT. However, it would be advantageous to establish a method that is able to discriminate and identify larger numbers of different materials using a multi-energy CT scanning system.

OBJECT OF THE INVENTION

It is an object of the invention to provide a method or methods for more effective quantification of different materials within an object using image data generated from a multi-energy CT imaging apparatus.

Alternatively, it is an object to provide new methods for post reconstruction material decomposition of multi-energy spectral CT data.

Alternatively, it is an object of the invention to provide an improved method, system and computer program for selection and presentation of a material decomposition algorithm to be used on image data generated using a multi-energy computer tomography (CT) system.

Alternatively, it is an object of the invention to provide an improved method, system and computer program product for improved quantification of different materials within an object.

Alternatively, it is an object of the invention to at least provide the public with a useful choice.

Alternatively, it is an object of the invention to provide a method and system to identify and quantify various different materials intrinsic to humans and animals.

SUMMARY OF THE INVENTION

According to a first embodiment of the invention there is provided a method for selecting a material decomposition algorithm using image data generated using a multi-energy computer tomography (CT) system, the method including;
    a) scanning an object using a multi-energy CT system to produce a set image data;
    b) applying one or more reconstruction techniques to the set image data to produce a set of reconstructed voxels;
    c) comparing each voxel to a reference set of material signal amplitude and noise properties in order to classify the voxels into air, low density or high density voxels; and
    d) based on the determination of c) selecting a first material decomposition method to be applied to low density voxels and/or selecting a second material decomposition method to be applied to higher density voxels.

According to a second embodiment of the invention there is provided a computer-implemented method for selecting and presenting a material decomposition algorithm using image data generated using a multi-energy computer tomography (CT) imaging system using a computer program product, the method including;
    a) scanning an object using a multi-energy CT system to produce a set of image data;
    b) sending the set of image data to a processor;
    c) receiving the set image data set in relation to an object;
    d) storing said data on a data storage medium;
    e) processing the data using one or more reconstruction techniques to produce a data set of reconstructed voxels;
    f) comparing each voxel in the reconstructed data set to a reference set of material signal amplitude and noise properties stored on a data storage medium;
    g) classifying the voxels into air, low density or high density voxels;

h) based on the determination of g) selecting a first material decomposition method to be applied to low density voxels and/or selecting a second material decomposition method to be applied to higher density voxels; and i) presenting the selected first and/or second decomposition method to an interface.

Preferably, the step of classifying voxels as air, low density or high density voxels includes comparing individual voxels to a reference distribution of a specific reference material using the Mahalanobis distance metric and Euclidian distance metric.

More preferably, the step of classifying voxels further includes the step of filtering the data to remove noise.

According to a third embodiment of the invention, there is provided a system for selecting and presenting a material decomposition algorithm using image data generated using a multi-energy computer tomography (CT) imaging system, the system comprising:

a) a means for scanning an object using a multi-energy CT system to produce a set of image data;

b) a means for sending the set of image data to a processor;

c) a means for receiving the set of multi-energy CT image data set in relation to an object;

d) a means for storing said data on a data storage medium;

e) a means for processing the data using one or more reconstruction techniques to produce a data set of reconstructed voxels;

f) a means for comparing each voxel in the reconstructed data set to a reference set of material signal amplitude and noise properties stored on a data storage medium;

g) a means for classifying the voxels into air, low density or high density voxels;

h) a means for, based on the determination of g), selecting a first material decomposition method to be applied to low density voxels and/or selecting a second material decomposition method to be applied to higher density voxels; and i) a means for presenting the selected first and/or second decomposition method to an interface.

According to a fourth embodiment of the invention there is provided a method for selecting a material decomposition algorithm using image data generated using a multi-energy computed tomography (CT) imaging system, the method including;

a) receiving reconstructed or non-reconstructed multi-energy CT image data in relation to an object;

b) if non-reconstructed, applying one or more reconstruction techniques to the set of images to produce a set of reconstructed voxels;

c) comparing the each voxel to a reference set of material signal amplitude and noise properties in order to classify the voxels into air, low density or high density voxels; and d) based on the determination of c) selecting a first material decomposition method to be applied to low density voxels and/or selecting a second material decomposition method to be applied to higher density voxels.

According to a fifth embodiment of the invention there is provided a computer-implemented method for selecting a material decomposition algorithm using image data generated using a multi-energy computer tomography (CT) imaging system using a computer program product, the method including;

a) receiving a reconstructed or non-reconstructed multi-energy CT image data set in relation to an object;

b) storing said data on a data storage medium;

c) if data received in a) is non-reconstructed, processing the data using one or more reconstruction techniques to produce a data set of reconstructed voxels;

d) comparing each voxel in the reconstructed data set to a reference set of material signal amplitude and noise properties stored on a data storage medium;

e) classifying the voxels into air, low density or high density voxels;

f) based on the determination of e) selecting a first material decomposition method to be applied to low density voxels and/or selecting a second material decomposition method to be applied to higher density voxels; and g) presenting the selected first and/or second decomposition method to an interface.

Preferably, the method further includes the step of scanning an object using a multi-energy CT system to produce a set of image data and the step of sending image data.

More preferably, the step of classifying voxels as air, low density or high density voxels includes comparing individual voxels to a reference distribution of a specific reference material using the Mahalanobis distance metric and Euclidian distance metric.

More preferably, the step of classifying voxels further includes the step of filtering the data to remove noise.

According to a sixth embodiment of the invention, there is provided a system for selecting and presenting a material decomposition algorithm using image data generated using a multi-energy computer tomography (CT) imaging system, the system comprising:

a) a means for receiving a reconstructed or non-reconstructed multi-energy CT image data set in relation to an object;

b) a means for storing said data;

c) a means for processing the data using one or more reconstruction techniques to produce a data set of reconstructed voxels;

d) a means for comparing each voxel in the reconstructed data set to a reference set of material signal amplitude and noise properties stored on a data storage medium;

e) a means for classifying the voxels into air, low density or high density voxels;

f) a means for selecting a first material decomposition method to be applied to low density voxels and/or selecting a second material decomposition method to be applied to higher density voxels; and g) a means for presenting the selected first and/or second decomposition method to an interface.

Preferably, the system includes a means for scanning an object using a multi-energy CT system to produce a set of image data and a means for sending image data.

According to a seventh embodiment of the invention there is provided a method for material quantification of data produced by a multi-energy CT system to identify and/or quantify one or more materials represented by the data, the material quantification method including the steps of:

a) for each of a plurality of reconstructed voxels contained within the data, enforcing a sparse solution for a maximum number of material combinations using 0-norm minimisation;

b) applying rejection criteria to the solution of a) to identify one or more specific materials.

According to an eighth embodiment of the invention, there is provided a computer-implemented method for identifying and/or quantifying, and presenting one or more materials represented by data produced by a multi-energy CT system using a computer program product, the method comprising:

a) receiving, directly or indirectly, an image data set from a multi-energy CT imaging apparatus and storing said data on a data storage medium;
b) calculating, for each of a plurality of voxels contained within the data set, a sparse solution for a maximum number of material combinations using 0-norm minimisation using a processor;
c) storing said sparse solutions on a data storage medium;
d) applying rejection criteria to the sparse solutions of b) to identify one or more materials; and
e) presenting the materials identified in d) via an interface.

Preferably, the step of calculating the sparse solutions further includes the steps of;

i) determining all combinations of the maximum number of materials present in the CT image data set;
ii) for each combination, constructing a reduced material matrix $M_r$;
iii) calculating a non-negative linear least squares solution $x_r$ for the sub problem $M_r x_r$=one voxel;
iv) determining which solution from iii) has the smallest least square error out of all the tested combinations determined in i);
v) selecting the solution determined in iv) as the best sparse solution.

Preferably the step of applying rejection criteria to the sparse solutions further includes the steps of;

i) identifying combinations of materials pre-determined not to be found in the same voxel and rejecting said combinations; and/or
ii) setting acceptable solution ranges for each material, and rejecting any sub-problem with a solution outside these ranges.

Preferably, the method includes decomposing data from five or more different materials.

Preferably, the multi-energy CT imaging apparatus used in the method uses two or more energy bands.

More preferably, the multi-energy CT imaging apparatus uses between two-eight energy bands.

More preferably, the method includes decomposing data from six different materials using four energy bands.

In preferred embodiments, the method includes the step of de-noising the data/images for each energy range prior to decomposition.

More preferably, the step of de-noising includes applying a cylindrical median filter for reducing high frequency noise.

In preferred embodiments the method includes the further step of enforcing one or more constraints to the individual material combinations.

According to a ninth embodiment of the invention, there is provided a system for identifying and/or quantifying one or more materials represented by data produced by a multi-energy CT system, the system comprising:

a) a means for directly or indirectly receiving an image data set from a multi-energy CT imaging apparatus;
b) a means for storing said data;
c) a means for calculating, for each of a reconstructed voxel contained within the image data set, a sparse solution for a maximum number of material combinations using 0-norm minimisation;
d) a means for storing said sparse solutions;
e) a means for applying rejection criteria to the sparse solutions of c) to identify one or more specific materials; and
f) a means for presenting the materials identified in d).

According to a tenth embodiment of the invention there is provided a method for identifying and/or quantifying one or more materials in an object using images produced by a multi-energy CT system, the method including the steps of;

a) scanning an object using a multi-energy CT system to produce an image data set;
b) applying one or more reconstruction techniques to the image data set to produce a set of spatially-reconstructed voxels;
c) comparing the density of each voxel to a reference set of material densities in order to classify the voxels into air, low radiographic density or high radiographic density voxels;
d) based on the determination of c) selecting a first material decomposition method to be applied to low density voxels and/or selecting a second material decomposition method to be applied to higher density voxels; and
e) applying a first material decomposition method to the low density voxels, the first material decomposition method including using volume constrained non-negative linear least squares to aid material identification; and/or
f) applying a second material decomposition method to the high density voxels, the second material decomposition method including using a method that aids material identification by enforcing a sparse representation of the material composition for each voxel.

Preferably, the step of applying a second material decomposition method further includes one or more of the steps as outlined in the seventh embodiment of the invention and the subsequent preferred embodiments.

According to an eleventh embodiment of the invention there is provided a computer implemented method for identifying and/or quantifying one or more materials in an object using images produced by a multi-energy CT system using a computer program product, the method including the steps of:

a) scanning an object using a multi-energy CT system to produce an image data set;
b) sending the image data set to a processor;
c) receiving the image data set in relation to an object;
d) storing said data on a data storage medium;
e) processing the data using one or more reconstruction techniques to produce a data set of reconstructed voxels;
f) comparing the radiographic density of each voxel to a reference set of material radiographic densities in order to classify the voxels into air, low density or high density voxels;
g) based on the determination of f), selecting a first material decomposition method to be applied to low density voxels and/or selecting a second material decomposition method to be applied to higher density voxels;
h) applying a first material decomposition method to the low density voxels, the first material decomposition method including using volume constrained non-negative linear least squares to aid material identification; and/or
i) applying a second material decomposition method to the high density voxels, the second material decomposition method including using an method that aids material identification by enforcing a sparse representation of the material composition for each voxel;

j) identifying specific materials with the object based on the solutions from h) and i); and k) presenting material identification information on an interface.

Preferably, the step of classifying voxels as air, low density or high density voxels includes comparing individual voxels to a reference distribution of a specific reference material using the Mahalanobis distance metric and Euclidian distance metric.

More preferably, the step of classifying voxels further includes the step of filtering the data to remove noise.

Preferably, the step of applying a second material decomposition method further includes one or more of the steps as outlined in the eighth embodiment of the invention and the subsequent preferred embodiments.

According to a twelfth embodiment of the invention there is provided a system for identifying and/or quantifying one or more materials represented by data produced by a multi-energy CT system, the system comprising:

a) a means for scanning an object using a multi-energy CT system to produce an image data set;

b) a means for sending the image data set to a processor;

c) a means for receiving the image data set in relation to an object;

d) a means for storing said data on a data storage medium;

e) a means for processing the data using one or more reconstruction techniques to produce a data set of reconstructed voxels;

f) a means for applying one or more reconstruction techniques to the set of projection images to produce a set of reconstructed voxels;

g) a means for comparing the radiographic density of each voxel to a reference set of material radiographic densities in order to classify the voxels into air, low density or high density voxels;

h) a means for selecting a first material decomposition method to be applied to low density voxels and/or selecting a second material decomposition method to be applied to higher density voxels;

i) a means for applying a first material decomposition method to the low density voxels, the first material decomposition method including using volume constrained non-negative linear least squares to aid material identification; and/or j) a means for applying a second material decomposition method to the high density voxels, the second material decomposition method including using an method that aids material identification by enforcing a sparse representation of the material composition for each voxel;

k) a means for identifying specific materials within the object based on the solutions from i) and j); and l) a means for presenting material identification information on an interface.

According to a thirteenth embodiment of the invention there is provided a method for identifying and/or quantifying one or more materials using images produced by a multi-energy CT system, the method including the steps of:

a) receiving a number of reconstructed or non-reconstructed multi-energy CT image data sets in relation to an object;

b) if non-reconstructed, applying one or more reconstruction techniques to the image data set to produce a set of reconstructed voxels;

c) comparing each voxel in the reconstructed data set to a reference set of material signal amplitude and noise properties and classifying the voxels into air, low density or high density voxels;

d) based on the determination of c) selecting a first material decomposition method to be applied to low density voxels and/or selecting a second material decomposition method to be applied to higher density voxels; and e) applying a first material decomposition method to the low density voxels, the first material decomposition method including using volume constrained non-negative linear least squares to aid material identification; and/or f) applying a second material decomposition method to the high density voxels, the second material decomposition method including using an method that aids material identification by enforcing a sparse representation of the material composition for each voxel.

According to a fourteenth embodiment of the invention there is provided a computer implemented method for identifying and/or quantifying a number of materials in an object using image data produced by a multi-energy CT system using a computer program product, the method including the steps of:

a) receiving a reconstructed or non-reconstructed multi-energy CT image data set in relation to an object;

b) storing said data on a data storage medium;

c) if data received in a) is non-reconstructed, processing the data using one or more reconstruction techniques to produce a data set of reconstructed voxels;

d) comparing each voxel in the reconstructed data set to a reference set of material signal amplitude and noise properties stored on a data storage medium;

e) classifying the voxels into air, low density or high density voxels;

f) based on the determination of e), selecting a first material decomposition method to be applied to low density voxels and/or selecting a second material decomposition method to be applied to higher density voxels;

g) applying a first material decomposition method to the low density voxels, the first material decomposition method including using volume constrained non-negative linear least squares to aid material identification; and/or h) applying a second material decomposition method to the high density voxels, the second material decomposition method including using an method that aids material identification by enforcing a sparse representation of the material composition for each voxel;

i) identifying specific materials with the object based on the solutions from g) and h); and j) presenting material identification information to an interface.

Preferably, the method includes the step of scanning an object using a multi-energy CT system to produce an image data set and the step of sending the image data set.

Preferably, the step of classifying voxels as air, low density or high density voxels includes comparing individual voxels to a reference distribution of a specific reference material using the Mahalanobis distance metric and Euclidian distance metric.

More preferably, the step of classifying voxels further includes the step of filtering the data to remove noise.

Preferably, the step of applying a second material decomposition method further includes one or more of the steps as outlined in the eighth embodiment of the invention and the subsequent preferred embodiments.

According to a fifteenth embodiment of the invention there is provided a system for identifying and presenting a number of different materials represented by data produced by a multi-energy CT system, the system comprising:
  a) a means for receiving a reconstructed or non-reconstructed multi-energy CT image data set in relation to an object;
  b) a means for storing said data on a data storage medium;
  c) a means for processing the data using one or more reconstruction techniques to produce a data set of reconstructed voxels;
  d) a means for comparing each voxel in the reconstructed data set to a reference set of material signal amplitude and noise properties stored on a data storage medium;
  e) a means for classifying the voxels into air, low density or high density voxels;
  f) a means for selecting a first material decomposition method to be applied to low density voxels and/or selecting a second material decomposition method to be applied to higher density voxels;
  g) a means for applying a first material decomposition method to the low density voxels, the first material decomposition method including using volume constrained non-negative linear least squares to aid material identification; and/or
  h) a means for applying a second material decomposition method to the high density voxels, the second material decomposition method including using an method that aids material identification by enforcing a sparse representation of the material composition for each voxel;
  i) a means for identifying specific materials with the object based on the solutions from g) and h); and
  j) a means for presenting material identification information on an interface.

Preferably, the system includes a means for scanning an object using a multi-energy CT system to produce a set of image data and a means for sending image data.

In preferred embodiments of the invention, the data is medical data and the low density reconstructed voxels represent soft tissue.

In further preferred embodiments the data is medical data and the high density voxels represent bone, implants, metals and/or contrasting agents.

According to a sixteenth embodiment of the invention there is provides a method for identification or quantification of one or more components within, or excised from an animal or human, the method including the steps of:
  a) scanning the animal, human or part thereof using a multi-energy CT scanner to produce an image data set or receiving a multi-energy CT image data set for the animal, human or part thereof;
  b) quantifying or identifying the one or more components based on the CT image data set using any one or more of the computer implemented methods of the eighth and fourteenth embodiments of the invention.

Preferably, the component to be identified or quantified is selected from plaque, cancer, cancerous tumours or markers and biological identifiers thereof, components associated with the inflammatory process or infection, bone or cartilage, pathogens, crystals, lipids or fats.

Preferably, the method includes the step of administering a nanocontrast agent targeted to the component to be identified to the animal, human or part thereof prior to scanning.

Preferably, the component to be identified is an atheroma or atherosclerosis plaque, or components within an atheroma or plaque.

Preferably, the nanocontrast agents are selected from agents comprising nanoparticles of one or more metals.

More preferably, the metals are selected from gold, gadolinium, iodine, hafnium, tantalum, bismuth, ytterbium, platinum, yttrium and/or rubidium.

In further preferred embodiments, the nanocontrast agent further includes a biologically active component.

More preferably the biologically active component is selected from a ligand, antibody or part of an antibody.

Preferably, method includes a calibration step wherein known concentrations of the nanoparticles are imaged and a calibration curve is generated.

In one preferred embodiment, the method includes quantifying components within ex-vivo and in-vivo tissue. More preferably ex-vivo and in-vivo samples are quantified simultaneously.

According to a seventeenth embodiment of the invention there is provided a method for measuring drug penetration into animal tissue, the method including the steps of:
  a) administering a nanocontrast agent targeted to drug to be identified within the tissue;
  b) scanning the tissue using a multi-energy CT scanner to produce an image data set;
  c) quantifying the drug within the tissue based on the image data set using any one or more of the computer implemented methods of the eighth and fourteenth embodiments of the invention.

According to an eighteenth embodiment of the invention there is provided a method for monitoring or identifying the presence of, or changes in specific tissue, tissues or components in an animal or human including the steps of:
  a) scanning the tissue or component using a multi-energy CT scanner to produce an image data set;
  b) quantifying the tissue(s) or components of interest within the animal or human based on the image data set using any one or more of the computer implemented methods of the eighth and fourteenth embodiments of the invention;
  c) repeating steps a) and b) over a period of time to generate information identifying the presence of, or changes in specific tissue, tissues or components over time; and
  d) developing a treatment plan for the animal or human based on the information provided from step c).

In preferred embodiments the method includes the step of administering a nanocontrast agent targeted to the specific tissue or component prior to scanning.

In one embodiment the method includes monitoring one or more arteries to determine, identify and/or manage the onset or progress of atherosclerosis.

In one embodiment the method includes monitoring cartilage health to determine, identify and/or manage the onset or progress of cartilage degeneration.

In an alternative embodiment the method includes monitoring bone health to determine, identify and/or manage the onset or progress of osteoarthritis or osteoporosis.

In an alternative embodiment the method includes monitoring a bone/implant interface to determine, identify and/or measure the ingrowth of bone into the implant.

In a further alternative embodiment the method includes monitoring biomarkers of specific cancers to determine, identify and/or manage the onset or progress of cancer.

In an alternative embodiment the method includes monitoring one or more specific markers of an inflammatory cell to determine, identify and/or manage the inflammation or infection.

In further alternative embodiments the method includes monitoring one or more pathogens to determine, identify and/or manage the pathogen and/or the pathogenic response.

According to a nineteenth embodiment of the invention there is provided a method for determining bone and/or cartilage health in an animal or human, the method including the steps of:
- a) scanning the bone and/or cartilage using a multi-energy CT scanner;
- b) quantifying the bone and/or cartilage within the animal or human based on the CT data using any one or more of the computer implemented methods of the eighth and fourteenth embodiments of the invention.

Preferably, the method of determining bone and/or cartilage health includes measuring or quantifying one or more of bone densitometry, trabecular thickness and/or orientation and/or spacing, collagen content in cartilage, fibrous tissue or bone, assessment of bone cancer, or disease, infection or inflammation of bone or adjacent cartilage.

More preferably the measurement is bone densitometry of a bone or part thereof and the method includes the step of determining the calcium hydroxyapatite concentration of the bone or part thereof.

Even more preferably, the step of determining the calcium hydroxyapatite concentration includes measuring the energy dependent Hounsfield units in the volume of bone or part thereof, reading the corresponding hydroxyapatite concentration from a calibration curve derived from measuring energy dependent Hounsfield units in a reference set of known concentrations of hydroxyapatite.

Preferably, the method of determining bone and/or cartilage health also includes measuring or quantifying bone densitometry, trabecular thickness and/or bone ingrowth to an implant surface, at a bone-implant interface.

Preferably, the method of determining bone and/or cartilage health includes the step of extracting molecular information relating to an ionic contrast agent and bone from an anatomical joint.

More preferably, the method includes the steps of
- a) injecting an ionic contrast agent into the joint space; and
- b) acquiring multi-energy images of the cartilage-subchondral interface.

In one preferred embodiment the ionic contrast agent is selected from an iodine or gadolinium based contrast agent.

According to a twentieth embodiment of the invention there is provided a method for identifying and/or quantifying biomarkers of specific cancers in an animal or human, the method including:
- a) scanning a tissue or region of interest in an animal or human using a multi-energy CT scanner to produce an image data set;
- b) identifying and/or quantifying biomarkers within the animal or human tissue based on the image data set using any one or more of the computer implemented methods of the eighth and fourteenth embodiments of the invention.

Preferably, the method of detecting, localizing and/or quantify biomarkers of specific cancers includes the further step of administering a nanocontrast agent to label specific tumour cell markers and/or markers of the cellular immune response including macrophages, T cells, and other immune response cell types at any tumour site, prior to the scanning step.

Preferably, the nanocontrast agent is or includes a functionalised nanoparticle.

Preferably, two or more different target components of the cancer are measured using a single 3D volume scan.

Preferably, the method step of identifying and/or quantifying biomarkers includes the step of quantifying specific drug delivery to a tumour site.

More preferably the method includes combining the drug or pharmaceutical with the nanocontrast agent or separately labelling the drug with a metal marker.

According to a twenty-first embodiment of the invention there is provided a method for identifying and/or quantifying pathogens in an animal or human, the method including:
- a) scanning a tissue or region of interest in an animal or human using a multi-energy CT scanner to produce an image data set;
- b) identifying and/or quantifying pathogens within the animal or human tissue based on the image data set using any one or more of the computer implemented methods of the eighth and fourteenth embodiments of the invention.

Preferably, the method includes the step of administering to the animal or human two or more different nanocontrast agents targeted to different potential pathogens, prior to scanning, for imaging together in a single multi-energy CT scan.

According to an twenty-second embodiment of the invention there is provided a method for determining the growth of tissue associated with an implanted scaffold or engineered tissue in an animal or human, the method including:
- a) scanning a tissue or region of interest in an animal or human using a multi-energy CT scanner to produce an image data set;
- b) identifying and/or quantifying the growth of tissue associated with an implanted scaffold or engineered tissue within the animal or human based on the image data set, using any one or more of the computer implemented methods of the eighth and fourteenth embodiments of the invention.

More preferably, the method further includes one or more of the steps of:
- identifying the implanted scaffold or engineered tissue within the animal or human;
- quantifying the type and/or quantity of new tissue associated with the scaffold or engineered tissue; and/or
- determining the resorption of the scaffold or engineered tissue.

Even more preferably, the step of identifying the implanted scaffold or engineered tissue includes identifying a material from which the scaffold or engineered tissue is made or identifying a material eluting from a scaffold or engineered tissue.

Even more preferably, the step of quantifying the type and quantity of new tissue associated with the scaffold or engineered tissue includes targeting specific cells or tissue types with nanocontrast agents prior to imaging.

More preferably the nanocontrast agent is delivered to the target cells or tissues by injection, topical application, or by incorporation within an implantable scaffold or stent.

Preferably, the method includes the further step of routinely determining the growth of tissue associated with an implanted scaffold or engineered tissue over a period of time and determining the success or likely success of the implanted scaffold or tissue based on the growth of the associated tissue.

According to an twenty-third embodiment of the invention there is provided a method for identifying and/or quantifying intracellular or extracellular lipid in the body or an animal or human, the method including:

a) scanning a tissue or region of interest in an animal or human using a multi-energy CT scanner to produce an image data set;
b) identifying and/or quantifying intracellular or extracellular lipid within the animal or human based on the image data set, using any one or more of the computer implemented methods of the eighth and fourteenth embodiments of the invention.

Preferably, the method includes identifying and/or quantifying myelination or intra-tumoral lipids.

According to an twenty-fourth embodiment of the invention there is provided a method for identifying and/or quantifying pore sizes in animal of human tissue, the method including:
a) scanning a tissue or region of interest in an animal or human using a multi-energy CT scanner to produce an image data set;
b) identifying and/or quantifying pore sizes within tissue or region of interest in the animal or human based on the image data, using any one or more of the computer implemented methods of the eighth and fourteenth embodiments of the invention.

Preferably, the method includes quantifying pores size by administering to an animal or human nanomaterials of one or more sizes and measuring nanoparticle content at a region of interest.

Preferably, the pore sizes measured are selected from pores in the liver, spleen, blood vessels or blood-brain barrier.

Preferably, method includes performing multi-energy CT imaging 12-36 hours following administration of nanoparticles to the animal or human. More preferably the imaging is performed 18-24 hours after administration of the nanoparticles.

According to an twenty-fifth embodiment of the invention there is provided a method for detecting and identifying benign and/or malignant breast diseases in an animal or human, the method including:
a) scanning a tissue or region of interest in an animal or human using a multi-energy CT scanner to produce an image data set;
b) identifying and/or quantifying benign and/or malignant breast diseases within tissue or region of interest in the animal or human based on the image data set, using any one or more of the computer implemented methods of the eighth and fourteenth embodiments of the invention.

Preferably, the method further includes one of more of the following steps:
identifying and/or quantifying lipid of fat within the breast;
identifying and/or quantifying microcalcifications within the breast;
administering to the animal or human targeted nanocontrast agents specific to breast tumour target cells prior to imaging, then identifying and/or quantifying the agent within breast tissue post imaging.

In one preferred embodiment the nanocontrast agents are targeted to oestrogen receptors or HER-2 receptors.

According to a twenty-sixth embodiment of the invention there is provided a method for measuring activation of a pro-drug in an animal or human, the method including the steps of:
a) labelling an active component of the pro-drug with a first nanocontrast agent;
b) labelling an inactive component of the pro-drug with a second nanocontrast agent;
c) administering the labelled pro-drug to the animal or human prior to imaging;
d) performing a first scan of the target area in the animal or human using a multi-energy CT scanner to produce an image data set;
e) determining the presence of and if present, measuring the inactive and active components of the pro-drug at the target area based on the image data set using any one or more of the computer implemented methods of the eighth and fourteenth embodiments of the invention;
f) after a pre-determined period of time, performing a second scan of the target area in the animal or human using a multi-energy CT scanner to produce a second image data set; and
g) determining the presence of and if present, measuring the inactive and active components of the pro-drug at the target area based on the second image data set using any one or more of the computer implemented methods of the eighth and fourteenth embodiments of the invention;
wherein the presence of the active component and absence of, or decrease in the quantity of the inactive component at step g) indicates drug activation.

According to a twenty-seventh embodiment of the invention there is provided a method for identification or quantification of a component within, or excised from an animal or human, the method including the steps of:
a) scanning the animal, human or part thereof using a PET or SPECT scanner;
b) using the results of step a), identifying a region of interest within the animal or human;
c) administering a nanocontrast agent to the animal or human targeted to the region of interest or drug to be delivered to that region;
d) scanning the animal or human using a multi-energy CT scanner to produce an image data set; and
e) quantifying the nanocontrast agent based on the image data set using any one or more of the computer implemented methods of the eighth and fourteenth embodiments of the invention.

Preferably, the region of interest is a residual cancer site and the nanocontrast agent is targeted to determine drug delivery to the residual cancer site.

Further embodiments of the invention, which should be considered in all their novel aspects, will become apparent to those skilled in the art upon reading of the following description which provides at least one example of a practical application of the invention.

For the purposes of this application the terms "low density voxels" and "high density voxels" should be taken to mean voxels containing low atomic number materials and high atomic number materials respectively.

"Soft tissue" items are low (radiographic) density and the definition includes tissue such as adipose tissue, brain (grey/white matter), skeletal muscle, lung tissue and blood, lipids and water. These examples of soft tissue contain a very high fraction of low atomic number atoms, largely organic molecules. Soft tissue of contains low levels of salts, such as NaCl or KCl. These are in relatively small amounts and are not of levels high enough to make significant contribution to the radiographic density, or to the mass density.

"Image data" is defined as any data directly or indirectly derived from one or more x-ray detectors of a multi-energy CT system. It typically consists of, but is not limited to, numbers (counts, or other brightness measures) for some or all the energy ranges of the multi-energy capabilities of the x-ray detector(s).

An "Image data set" refers to a full set of data, including numbers for every pixel, for every projection image of a particular object being scanned. Without loss of generality, the term "image data set" as used within the specification includes both a full set of image data, or any subset of a full set of image data.

Example of high density materials are bone, cartilage, implants or scaffolds implanted into the body, and metals or heavy metals, including those forming part of nanocontrast agents such as gold, gadolinium, iodine, hafnium, tantalum, bismuth, ytterbium, platinum, yttrium and/or rubidium as a selection of non-limiting examples.

It should be noted that multi-energy CT is often called spectral CT to distinguish it from the original dual-energy modalities. However it has now become commonplace to also refer to dual-energy as spectral. To avoid any confusion that may occur we have refrained from using the term "spectral" where possible. In place of this we use dual-energy to specifically refer to the dual-energy modalities, and we use the term multi-energy to refer to both dual-energy CT and modalities of CT capable of measuring more than two energy ranges such as the MARS scanner.

BRIEF DESCRIPTION OF THE DRAWINGS

One or more embodiments of the invention will be described below by way of example only, and without intending to be limiting, with reference to the following drawings, in which:

FIG. 21 shows a computer implemented method for the identification of materials within an object method in a further embodiment of the invention;

DETAILED DESCRIPTION OF PREFERRED EMBODIMENTS OF THE INVENTION

Figure 1:
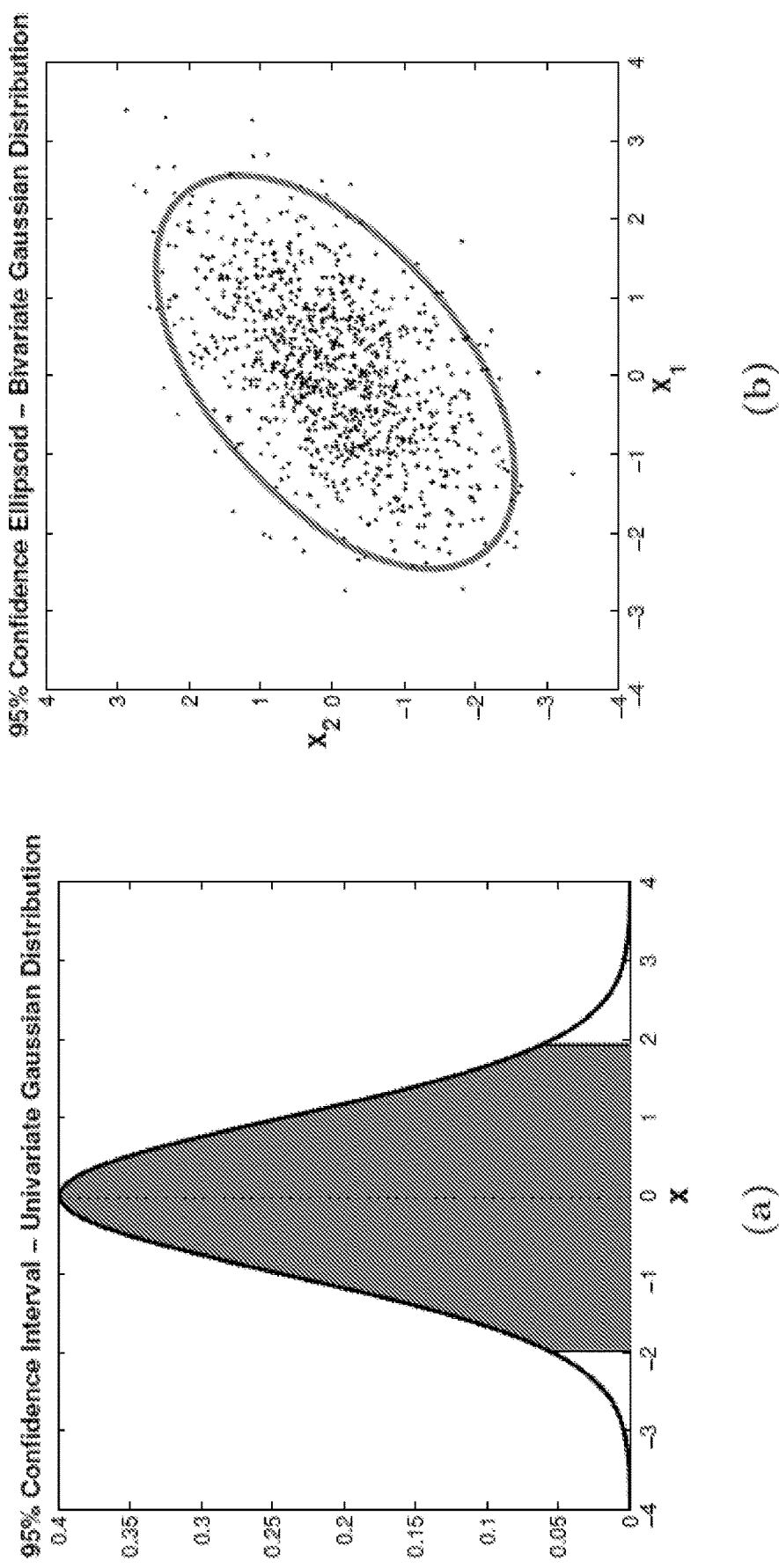
FIG. 1 shows (a) An example of a 95% confidence interval (shaded region) for a univariate Gaussian distribution and (b) An example of a 95% confidence ellipsoid (inside the blue ellipse) for a bivariate Gaussian distribution.

The invention generally relates to the methods for identification and quantification of a number of different materials within an object using one or more multi-energy CT imaging devices and the image data sets produced therefrom. The invention also relates to one or more computer program products, computer systems or computer implemented methods for the identification of multiple materials within an object.

One embodiment of this invention discloses a material quantification algorithm which will be discussed below as the "MARS-MD" or "MARS-MD algorithm" or "MARS-MD program". The purpose of this algorithm is to identify large numbers of different materials simultaneously from data collected by a multi-energy CT scanner. In summary, this is achieved by using the following three properties: solve only for sparse solutions; separate the soft tissue problem from the dense material problem; and use a combinatorial approach to allow for simple application of different constraints to different combinations of materials. It is shown that this algorithm may easily decompose six different materials using four energy bands.

A more detailed discussion of the methods developed is given below with reference to the use of the methods for the purposes of medical imaging of human tissues. This application is not intended to be limiting, and it is envisaged the techniques and methods discussed herein may be applied to a wide range of applications, both within the medical field and outside of it. More specifically, the methods described below relate to the imaging of human tissue in various applications, with reference to FIGS. 1-33.

MARS-MD is a material quantification algorithm for processing multi-energy CT datasets produced by one or more multi-energy CT scanners. The overall material decomposition algorithm of the present invention first uses a statistical segmentation technique (SST) algorithm to determine whether a reconstructed voxel is either low density material or high density material which will then determine the type of material decomposition algorithm used for that voxel.

Following the application of the SST algorithm, voxels containing low density material will be decomposed into lipid and water using volume constrained non-negative least squares. Voxels with high density material will be decomposed using a new method which will be referred to herein for the purposes of the description only as the combinatorial material decomposition (CMD) or "CMD algorithm". The full material matrix used by the MARS-MD program has been experimentally determined using scans of phantoms with known composition.

The first algorithm used within in the MARS-MD algorithm is referred to as the SST algorithm. Multi-energy CT data not only contains intensity information in the relative differences in attenuation between materials, it also contains spectral information from the differences in attenuation across energy. The segmentation technique described herein separates multi-energy CT data based on both spectral and intensity information. The SST algorithm uses confidence ellipsoids to analyse spectral information.

The aim of this segmentation procedure is to identify each voxel as one of three material classes: either air, low radiographic density, or high radiographic density. When applied to medical imaging as in the example given in the description, the voxels may be identified as air, soft tissue or dense voxels. For other applications other density related characteristics related to the specific materials within the voxels may be used.

When using the present invention for medical purposes, soft tissue is assumed to be primarily composed of lipid, water and protein such as adipose tissue, muscle, blood or cartilage. Radiographically dense materials are considered to be bone, metal or tissue containing contrast pharmaceuticals. These groups of materials have been chosen since the linear attenuation for air is strictly less than that for soft tissues and the linear attenuation for soft tissues is strictly less than that for dense materials.

SST breaks the segmentation process into two parts. The first stage of SST compares each voxel to the boundary materials of the soft tissue material class using the Mahalanobis distance metric. All voxels found to be within the 95% confidence ellipsoid of either boundary materials are preferentially assigned to the soft tissue class as they are considered to be spectrally identical. Any voxel found to be outside both 95% confidence ellipsoids are assigned based on comparing their Euclidean norms to that of the boundary materials: if less than lipid then the voxel is assigned to air; if between lipid and water then is assigned to soft tissue; and if greater than water then is assigned to dense materials.

In statistics, a confidence interval is a range of values that measurements from a given distribution can be considered reliable for a given confidence level. If the interval has a confidence level of 95%, then 95% of all measurements taken from that distribution would be expected to be contained within that confidence interval, as shown in FIG. 1.

It is typically not sufficient to approximate a multi-variate data with a collection of uni-variate confidence intervals. This is because as well as having variance in each variable there is also covariance between variables. To consider the effect of covariance, the confidence interval needs to be replaced by a confidence ellipsoid, shown as (b) in FIG. 1. A measurement is found to be inside a confidence ellipsoid if the Mahalanobis distance between the measurement and the mean of the distribution it was sampled from is less than or equal to the value of the $\chi^2$ distribution for the associated confidence level.

The Mahalanobis distance metric, $D_M(x, \mu)$, is a measure of how close a measurement x from a distribution is to the distribution mean $\mu$, taking into account correlations in the data. For a multivariate normal distribution with covariance $\Sigma$, the Mahalanobis distance between any measurement x and the distribution mean $\mu$, is given by $$D_M(x,\mu)^2=(x-\mu)^T\Sigma(x-\mu)$$

The second stage of SST is the application of a median filter to each of the air/soft-tissue/dense images obtained above. This is required as the allocation process in the first stage will typically contain salt and pepper noise. The covariance matrix used in the calculation of the Mahalanobis distance in SST is obtained by sampling a homogeneous region of air in a single slice of the volume. It is assumed that this matrix is representative of the covariance matrix for the entire volume.

The Statistical Segmentation Technique Algorithm can be represented as below (ALG 1.0), where X represents binary images for each material class, $\mu$ represents linear attenuation and $\upsilon$ represents a linear attenuation vector.

---

Select air region in volume, use to calculate estimate for $\Sigma$.
Set E = number of energies.
Set a zero image for each $X_{air}$, $X_{soft\ tissue}$ and $X_{dense\ material}$.
Set $\lambda$ equal to the $\chi^2$ value for p = 0.05 with E variables.

Calculate $\|\mu_{water}\|_2^2$ and $\|\mu_{lipid}\|_2^2$.
for (every voxel v in volume) do Calculate $D_M(v, \mu_{water})$, $D_M(v, \mu_{lipid})$ and $\|v\|_2^2$.
    if ($D_M(v, \mu_{water}) \leq \lambda$ OR $D_M(v, \mu_{lipid}) \leq \lambda$) then
        Set   $X_{soft\ tissue}(v) = 1$.
    else if ($\|v\|_2^2 < \|\mu_{lipid}\|_2^2$) then

```
            Set X_air(v) = 1.
        end if
        if (||μ_lipid||₂² < ||v||₂² < ||μ_water||₂²) then
            Set X_soft tissue(v) = 1.
        end if
        if (||μ_water||₂² < ||v||₂²) then
            Set X_dense material(v) = 1.
        end if
    end if
end for
Apply a median filter to each X_air, X_soft tissue and X_dense material.
```

Figure 2:
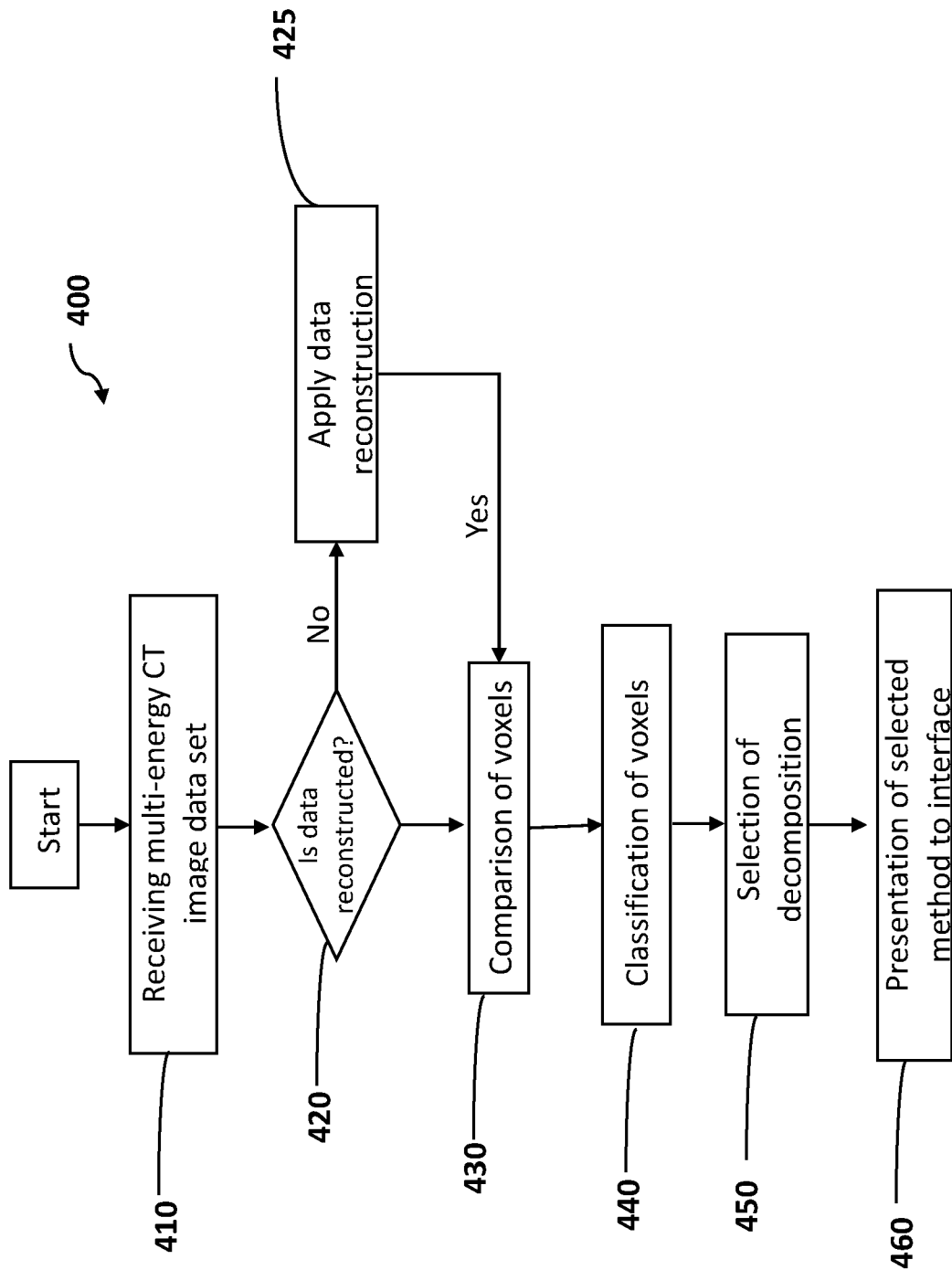
FIG. 2 shows a computer implemented method for selection of a decomposition method in one embodiment of the invention.
Figure 3:
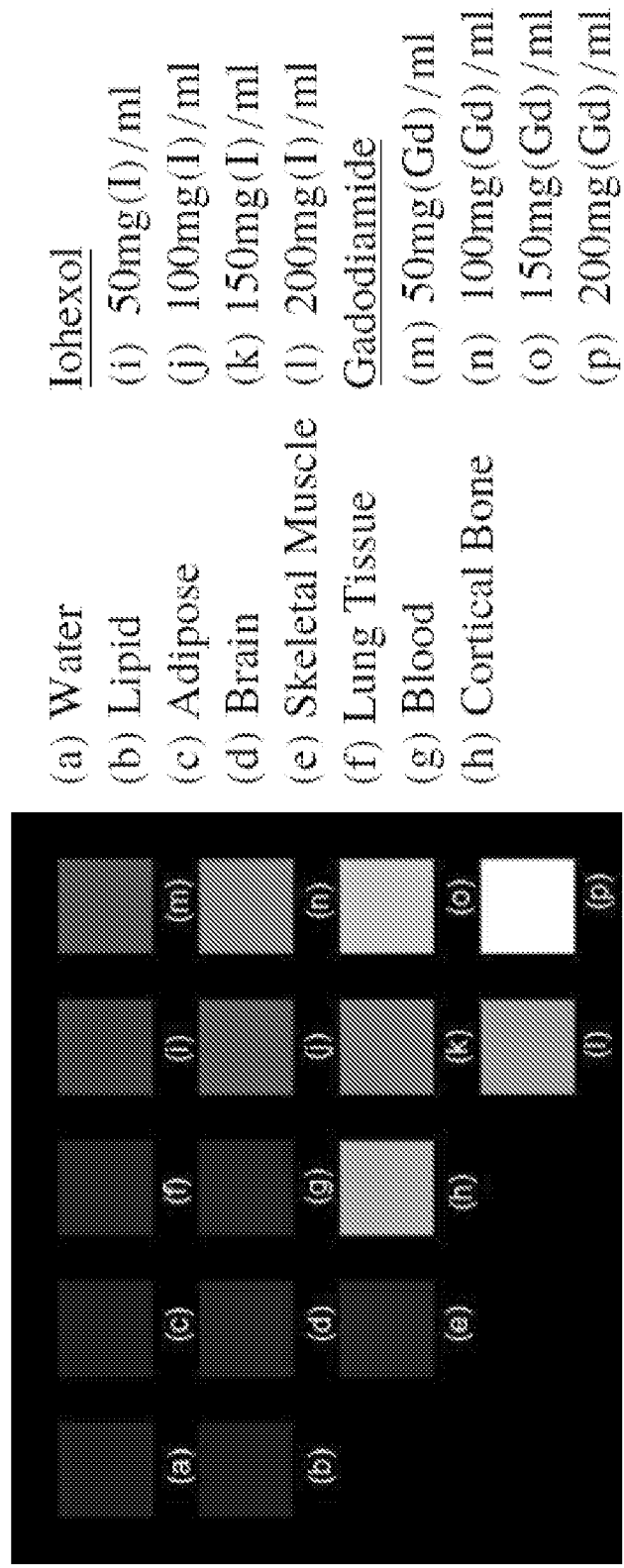
FIG. 3 shows a simulated phantom containing a variety of soft tissue and dense materials. Each material region is 100×100 voxels in size and surrounded by air.

The SST algorithm 100 as applied to a computer program product is summarised in FIG. 2. In the method described in FIG. 2, image data from a multi-energy CT scan is received by a processor. It is envisaged that multi-energy CT image data may be generated from a scanning system directly linked to the processing system, or received from a remote location via a network. Image data is received by processor 410 then if non-reconstructed, is reconstructed with algorithm 425 using known data reconstruction techniques, for example an algebraic reconstruction technique, to produce a set of reconstructed voxels. Reconstructed voxel data is then compared to a reference set of material signal amplitude and noise properties 430 stored in a database and the voxels then classified into air, low density or high density voxels 440 based on comparison with the reference set.

Based on the determination of voxel density during the classification step, a first material decomposition method is selected to be applied to low density voxels and a second material decomposition method is selected to be applied to higher density voxels 450. Information regarding the selection of the appropriate decomposition method is communicated to an interface 460. In preferred embodiments of the invention the interface is an application program interface (API) although a range of other known interfaces are encompassed by the scope of the invention, including, but not limited to user interfaces, software and hardware interfaces.

A simulated phantom was used to investigate how the SST algorithm worked with a range of different tissues and for images with different signal to noise ratio (SNR). The simulated phantom can be seen more clearly in FIG. 3. The simulated phantom contained a range of soft tissue materials including adipose tissue, brain (grey/white matter), skeletal muscle, lung tissue and blood (whole). These along with lipid and water are the phantom's soft tissue class materials. Dense materials chosen for the phantom include cortical bone along with various concentrations of Iohexol™ (iodine) and Gadodiamide™ (gadolinium) solutions—which are commonly used as part of commercial contrast pharmaceuticals. Each material region in the simulated data is 100×100 voxels in size.

The upper segmentation boundary ($\mu_{water}$ in Alg. 1.0) was chosen to be $\mu_{blood}$ as it is the highest attenuating soft tissue of those selected. The lower segmentation boundary was chosen to be $\mu_{lipid}$. Six subtracted energy bands were constructed from a simulation of a 120 kVp tungsten x-ray spectrum passing through 12 mm Al filtration. The effective lower boundaries of these energy bands are 30.4, 37.0, 45.5, 56.1, 68.2 and 92.9 keV. In addition the effective upper boundary of all these energy bins is 120 keV. Linear attenuation coefficients for each material at each effective energy band were obtained from the NIST XCOM database, a web database produced by the National Institute of Standards and Technology, currently available at www.nist.gov.

Figure 4:
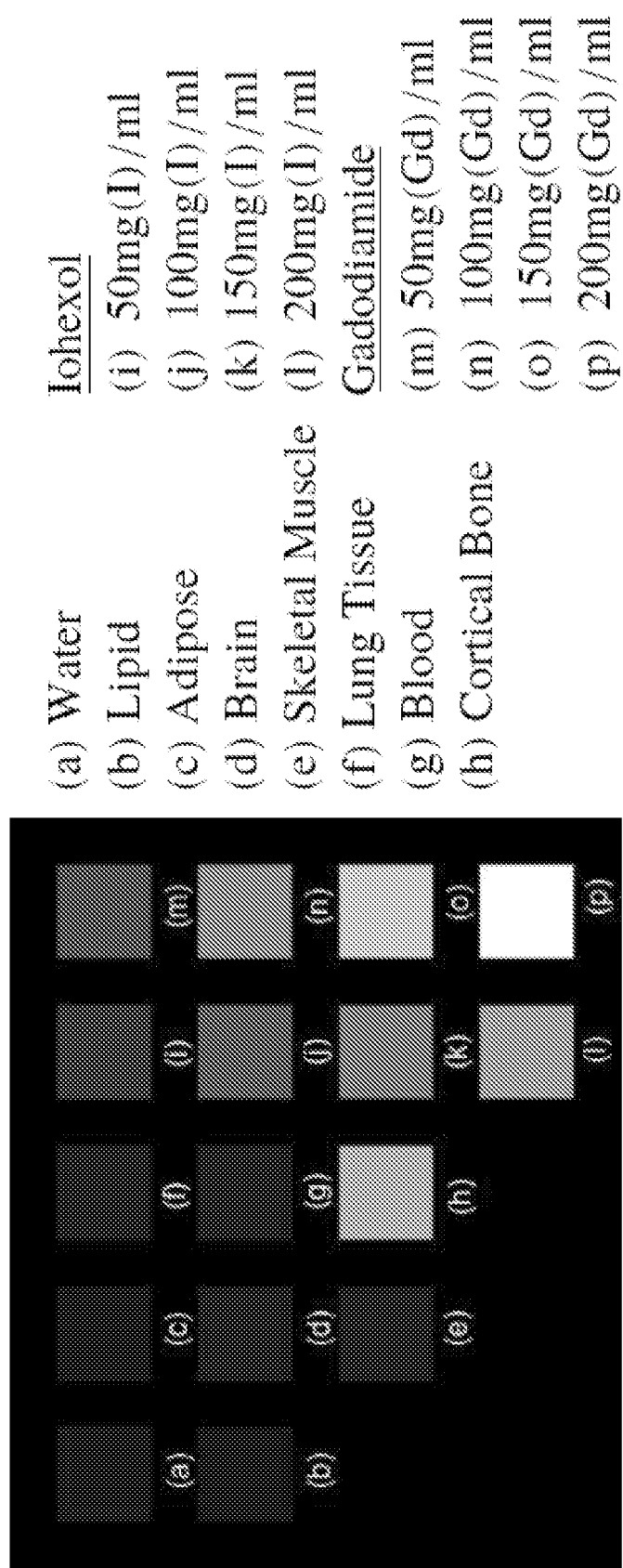
FIG. 4 shows a simulated phantom containing a variety of soft tissues and dense materials, each material region being 100×100 voxels in size and surrounded by air.

FIG. 4 shows a simulated phantom containing a variety of soft tissues and dense materials, each material region being 100×100 voxels in size and surrounded by air.

Figure 5:
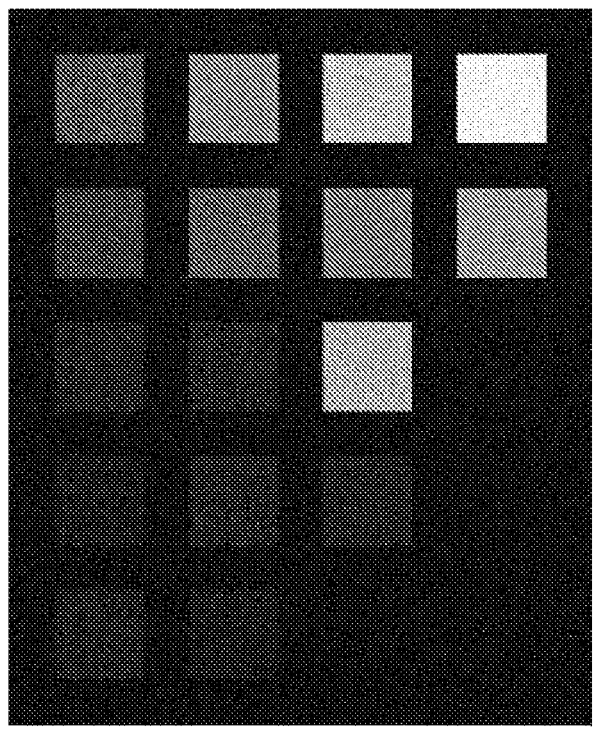
FIG. 5 shows a simulated phantom with two different levels of white Gaussian noise added, SNR=10 and SNR=20.
Figure 5:
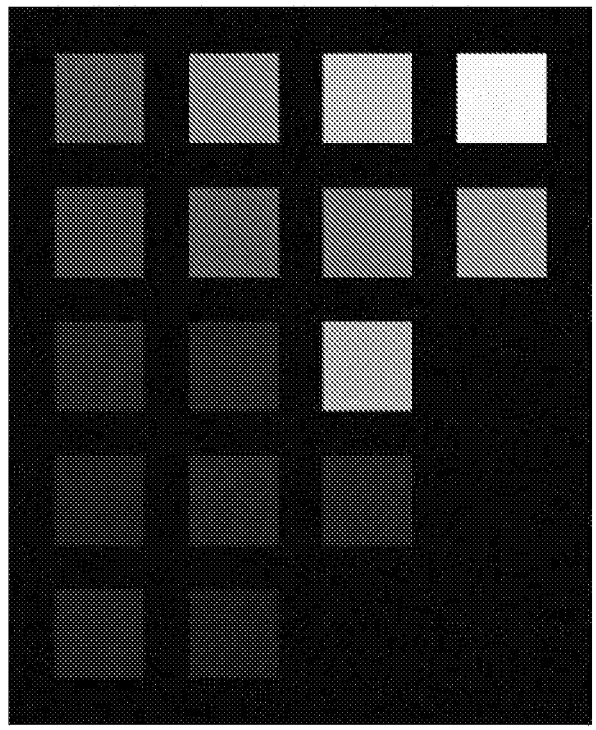

The SST algorithm was tested at six different levels of SNR—10, 20, 30, 40, 50, and 60. This was done by adding white Gaussian noise to the simulated dataset. FIG. 5 shows the 30.4 to 37.0 keV image for SNR of 10 and 20.

Results

Figure 6:
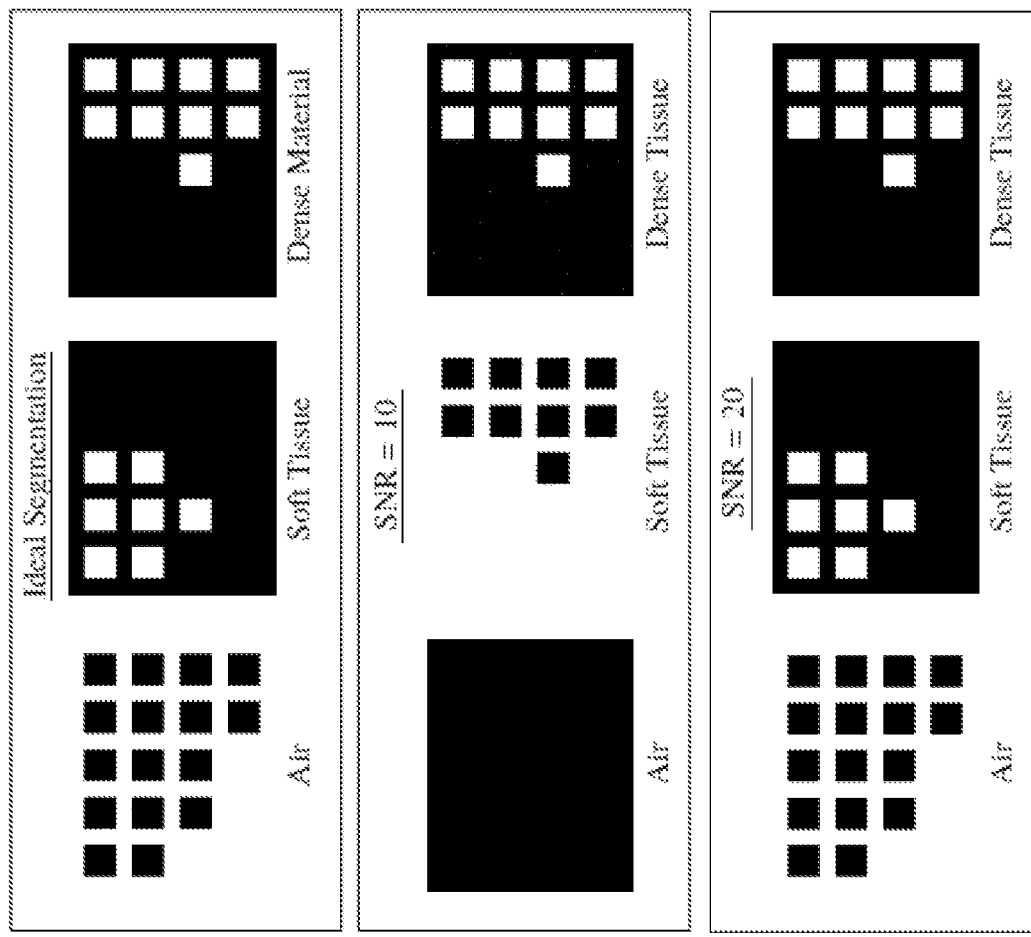
FIG. 6 Ideal segmentation outcome and the segmentation results for SNR=10 and SNR=20.

It was found that there is greater than 99.99% correct voxel assignment for all SNR values tested apart from an SNR of 10. As shown in FIG. 5, the test with an SNR of 10 allocated air voxels to the soft tissue class. FIG. 6 shows the ideal segmentation outcome results for SNR=10 and SNR=20. It is seen that air is incorrectly allocated to the soft tissue class for SNR=10, whereas SNR=20 provides near perfect segmentation.

The allocation of voxels to the wrong material class in the SST algorithm was investigated. This was tested using samples of 9216 simulated air voxels (assumed to have zero effective attenuation) and white Gaussian noise added with SNR ranging from 10 to 20 (in steps of one). This SNR range was chosen due to the previous section's results suggesting the SNR limit for the algorithm's success lies within this range. Two tests were performed:

1. Measuring the percentage of air voxels assigned to the correct material class when two different parameters are varied—the number of energy bands (ranging from 1-6) and the SNR of the energy bands (ranging from 10-20). All energy bands in the given number of energy bands and SNR level each have the same SNR.

2. Determining the effect that using energy bands at different levels of SNR has on the segmentation.

Starting with a fixed number of energy bands each with the same SNR (chosen to be 5 energy bands with SNR=16), add another energy band to the segmentation with and SNR ranging between 10-20. The purpose of these tests is to find both the minimum SNR for successful segmentation, and to determine how this minimum changes when different quality spectral information is used (i.e. different numbers of energy bins and different levels of noise in each energy bin).

Figure 7:
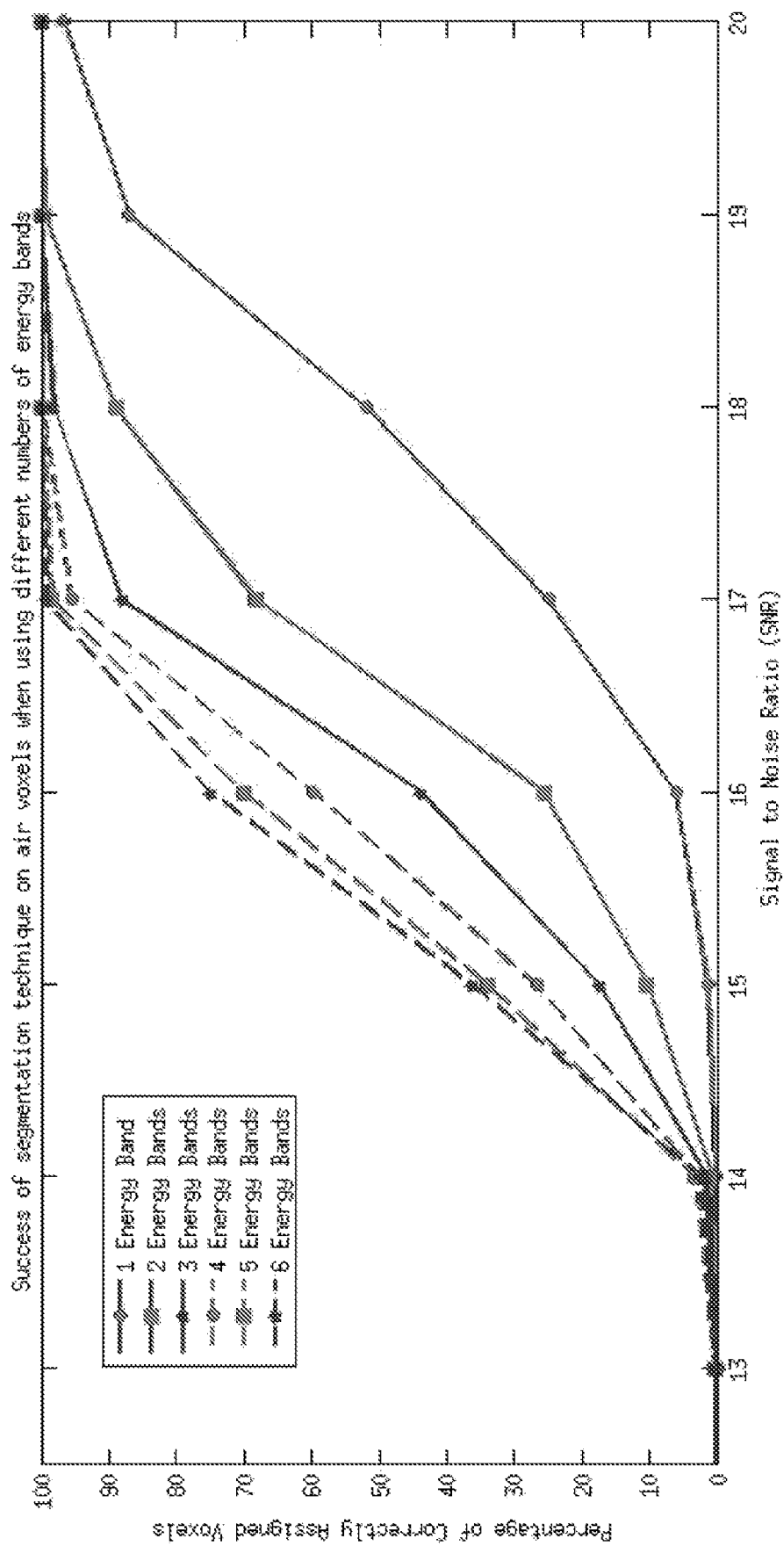
FIG. 7 shows the percentage of air voxels correctly assigned during segmentation for varying numbers of energy bands and levels of SNR.
Figure 8:
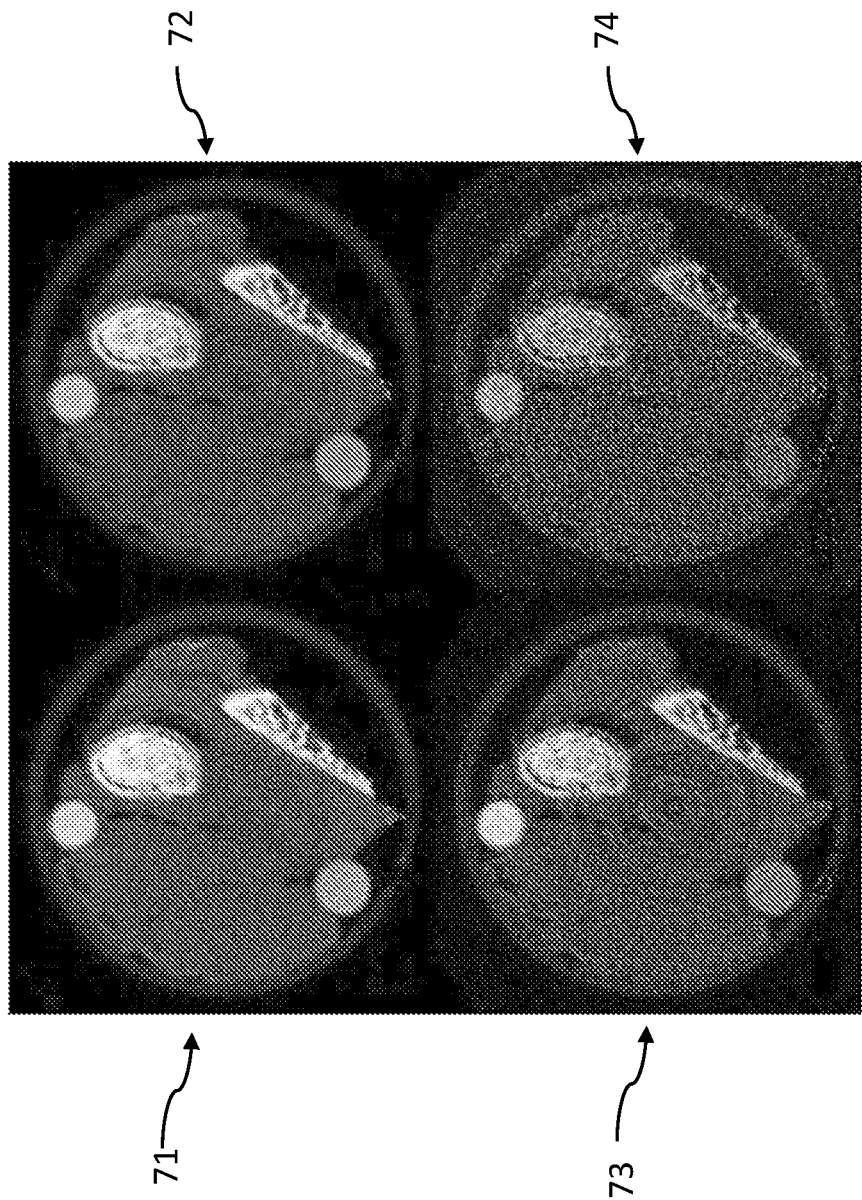
FIG. 8 shows a multi-energy CT scan of lamb meat phantom. The top PCR tube (circle) contains a KI solution and the bottom PCR tube contains a $CaCl_2$ solution.

The results from the first test shown in FIG. 7 indicate that if more energy ranges are included in the segmentation (assuming identical SNR) then more voxels will be assigned correctly at lower SNR levels. There is a significant difference in performance when moving from using no spectral information (1 energy band) to using spectral information (2+ energy bands). The degree of improvement from each additional extra energy added however decreases as more energy bands are included.

The second test showed that when an extra energy band is added to the segmentation the following is observed: If the added energy band has higher SNR than the other energy bands then the segmentation is improved—as would be expected; if it has lower SNR then the segmentation will typically be worse. There is however a buffer region where the benefit of including another energy band is greater than the negative effects of that energy band having lower SNR (if the difference in SNR between the new and other energy bands is small enough), which will result in an improved segmentation.

Example Using SST

A phantom was made with lamb meat, bone and PCR tubes containing CaCl2 and KI solutions. The phantom was then scanned with a MARS multi-energy CT scanner equipped with a CdTe Medipix-3RX detector operating in charge summing mode. The acquisition simultaneously measured four energy ranges: 14.7-80 keV (shown as 71 in FIG. 8), 19.7-80 keV (72), 32.8-80 keV (73) and 44.8-80 keV (74). Each energy range was reconstructed separately using an algebraic reconstruction technique and the resulting images shown in FIG. 8.

Figure 9:
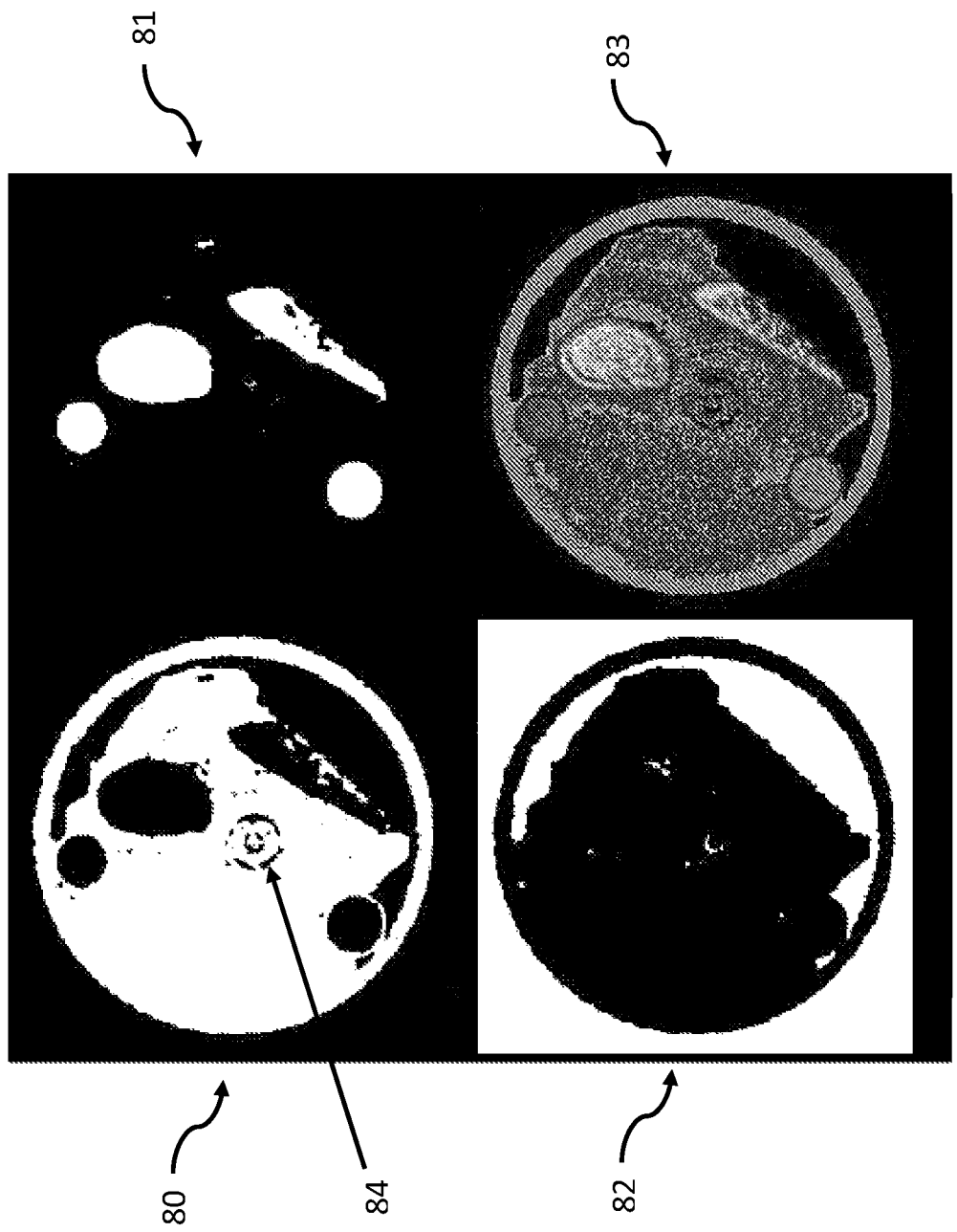
FIG. 9 shows the material classes produced by SST algorithm applied to lamb meat phantom reconstruction. Material decomposition image also included (bottom right)—artificial colouring used in material decomposition image: lipid=yellow, water=red, calcium (bone)=grey, and iodine=green.

The SST algorithm was applied to the reconstructed lamb meat phantom data during material analysis. Each different material in the sample was mostly found to identify with the appropriate material class as shown in FIG. 9, which shows a soft tissue class map 80, dense tissue/contract class map 81, air class map 82 and material decomposition 83. The main exception to this is in regions containing significant artifacts, for example the ring artifact 84 which is clearly visible in the soft tissue class map 80. The result of material decomposition (using the algorithm presented later in the description) is also shown in FIG. 9 at 83.

It is evident from the results in FIG. 7 that the segmentation algorithm can manage noisier data when multi-energy data (instead of single-energy) is used. This demonstrates that there is much benefit to be gained from integrating spectral information into segmentation techniques used in multi-energy x-ray imaging.

The simulations that are presented here analyse how the algorithm performs with simple Gaussian noise. Real world measurements however are corrupted with many different types of noise, for example electrical noise and ring artifacts. The segmentation of the lamb meat phantom is provided to show that this algorithm also performs reasonably well with real data.

Combinatorial Material Selection

It is well established that the method of ordinary linear least squares, when used for material decomposition, does not perform well when attempting to decompose data into a large number of materials. This poor performance is in part due to the similarities between the attenuation properties of materials which are typically of interest in this problem (e.g. lipid, water, protein, bone, metal and iron). Including many such materials into the material decomposition problem results in a material matrix which has a high condition number (i.e. is close to singular) and therefore is typically too ill-conditioned to solve using ordinary linear least squares.

To overcome this limitation, extra information or approximations about the data are generally used. Some examples of these include: adding constraints for either volume or mass conservation within voxels; using an estimate of the data's covariance matrix to add further stability to the inversion; and assuming that there is a maximum number of materials per voxel, a number that is less than the number of materials in the material matrix (this also known as a sparse solution).

Disclosed below is an algorithm that uses a combinatorial approach to finding a sparse solution to the material decomposition problem. For the purposes of this specification this algorithm will be referred to as the combinatorial material decomposition or CMD algorithm.

First a brief introduction is given to sparse solutions to problems and how they are found. Then the combinatorial material decomposition algorithm will be disclosed. Finally analysis of a "six material four energy" material decomposition of experimental data using the combinatorial material decomposition algorithm is presented.

Finding Sparse Solutions

Suitable solutions to the material decomposition problem are typically sparse. For example, if a material basis contains four materials (bone, lipid, water and iodine) then a voxel representing bone is described using only one of the four basis materials (i.e. bone) and a voxel representing iodine pharmaceutical in blood will be well described using two of the basis materials (i.e. water and iodine).

A solution to a problem is said to be sparse if the number of basis elements required to describe the solution is less than the total number of elements in the basis. This can be described more formally by the following: given a basis B with N elements $$B \triangleq \{x_1, x_2, \ldots, x_N\} \quad (4.2)$$

a measurement f is said to have a sparse representation in that basis if the number of non-zero coefficients $a_j$ in the decomposition of f into that basis is less than N, where $$f(B) \triangleq a_1 x_1 + a_2 x_2 + \ldots + a_N x_N \quad (4.3)$$

If f(B) has k<N non-zero coefficients then f is said to be k-sparse in B.

When determining which method is suitable for solving a given problem (such as material decomposition) it is important to know if desired solution should be sparse. This is because various techniques, such as least squares, favour finding non-sparse solutions. This concept of a technique of preferentially finding either a sparse or non-sparse solution is shown in FIG. 10.

This example shows the result of minimizing a residual vector w using three norms. The thick grey lines represents constant value of the objective function (also known as objective function contours or p-norm balls) and the thin grey diagonal line represents all feasible solutions to the problem. If the objective function contour is blown up (i.e. the value of the objective function is increased) then where it first hits the diagonal line of feasible solutions is the solution that is found by solving the optimization problem with the given norm. It can be seen from this example that techniques such as least squares will almost never provide a sparse solution, where as minimizing the equivalent 0-norm or 1-norm problems will almost always provide a sparse solution.

Minimisation problems using these sparsity promoting norms are typically associated with compressed sensing (or compressive sampling). This class of techniques is well known for its achievement of overcoming the Nyquist sampling rate limitations of classical signal processing techniques. They also have applications in image and signal de-noising. Compressed sensing works by transforming a non-sparse signal into a space where it has a sparse representation (for example—using a wavelet transform). The given problem (such as de-noising) is then solved in the transform space as a sparse optimization problem using either the 0-norm or 1-norm. Using the 0-norm for optimization is usually avoided as it is a non-convex problem requiring combinatorial methods to solve (of which the length of time required is infeasible in applications dealing with large systems). The 1-norm is preferred over the 0-norm for compressed sensing as it provides a convex optimization problem.

Figure 10:
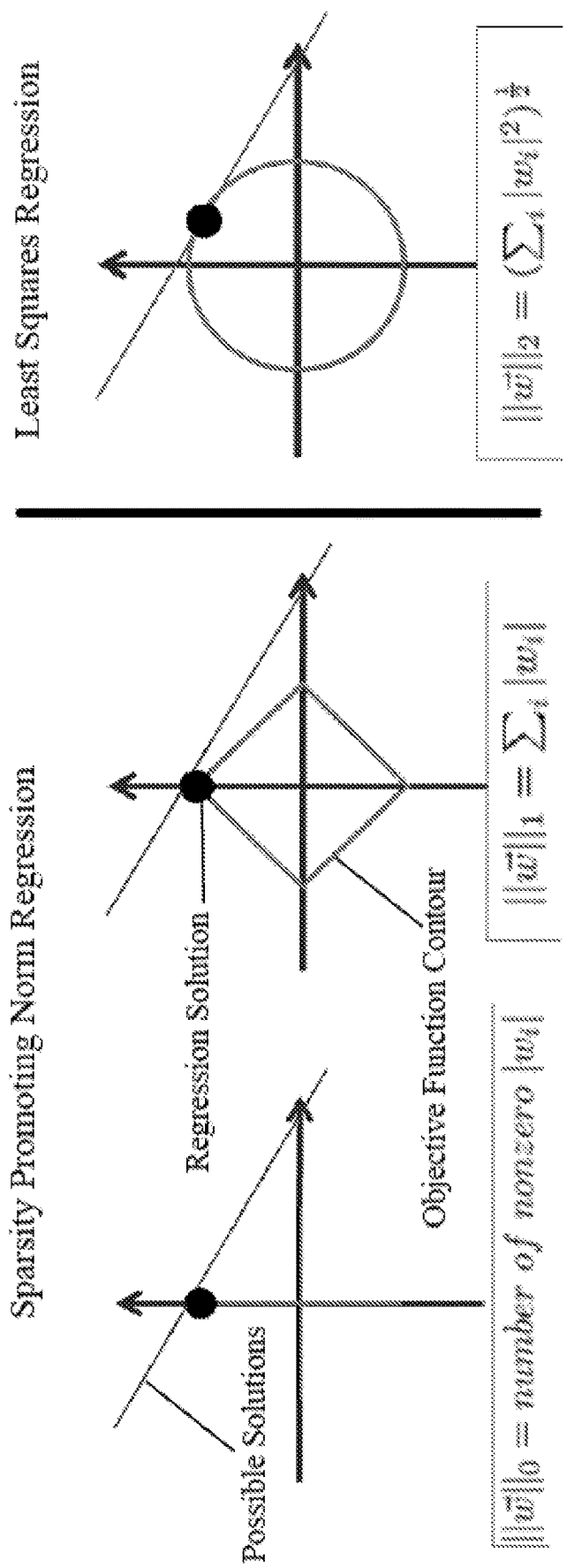
FIG. 10 shows objective function contours (red) from minimizing a residual vector ~w using the 0-norm, 1-norm and 2-norm.

FIG. 10 shows objective function contours from minimizing a residual vector w using the 0-norm, 1-norm and 2-norm. The solution returned by the respective minimization is given by where the contour touches the line of feasible solutions. Sparse solutions are promoted by using 0-norm and 1-norm minimization, whereas 2-norm minimization will rarely produce sparse solutions.

Combinatorial Material Decomposition (CMD) Algorithm

The combinatorial material decomposition (CMD) is an algorithm developed by the inventors which uses 0-norm minimization to achieve sparse solutions. The 0-norm was considered ideal for sparse material decomposition for the following reasons: having to check each combination of materials enables non-physical solutions and solutions with unlikely combinations of materials to be explicitly rejected; and each voxel in material decomposition is treated as an independent problem with few variables, therefore it does not take an unreasonably long time to calculate the desired sparse material combinations. The CMD algorithm (Alg. 2.0 below) is best described in two parts, first the calculation of sparse solutions for the data set and then the solution rejection criteria used to remove non-physical solutions.
Calculating Sparse Solutions As stated earlier, given a voxel in a reconstructed multi-energy CT scan b the system of equations required to be solved for material decomposition is $Mx=b$ where M is the material matrix containing N materials and x is the vector describing the composition of the voxel.

The sparse solutions problem being solved in CMD is given by;

$$\min_{x} \; \|Mx - b\|_2^2 \; \text{s.t.} \; \|x\|_0 \le k, \; x_j \ge 0 \; \forall \; j \qquad (4.4)$$

where k is the maximum level of sparsity (number of materials) allowed in the solution and k<N.

This problem is solved by first determining all combinations of k and fewer materials represented by the material matrix. For each combination a reduced material matrix $M_r$ is constructed using the respective materials, then the non-negative linear least squares solution $x_r$ is calculated for the sub-problem $M_r x_r = b$. The solution which has the smallest least square error out of all the tested combinations is then selected as the best solution.

A clear advantage of this algorithm is that the success of the problem is limited by material sparsity rather than the number of energy bands. By this we mean that if you have for example two energy bands (dual-energy) then standard least squares (without constraints such as mass conservation) limits the material matrix to two materials before it is under-determined (or rank deficient). However, with this type of algorithm it is the "reduced material matrices" that are used in the least squares procedure, and therefore it is the "reduced material matrices" that are limited to two materials (i.e. the maximum level of sparsity). This means that the CMD algorithm can have a full material matrix with more materials than energies without ever having to deal with the problems associated with under-determined non-square matrices.
Solution Rejection Criteria As stated above, using a combinatorial algorithm enables an easy method to reject solutions which either are non-physical or consist of an unlikely combination of materials. The CMD algorithm described below (Alg. 2.0) is given by the base formulation above combined with the following two rejection criteria:

1. Combinations of materials which are pre-determined not to be found in the same voxel are automatically rejected. For example it would be expected that bone would generally not be found in the same voxel as soft tissue or iodine intra-vascular contrast, therefore those combinations can be rejected.

2. An acceptable solution range is set for each material, any sub-problem with a solution substantially outside of these ranges is automatically rejected. For example, the density of bone does not vary wildly from 1.9 g/ml therefore if a solution found to be 0.02 g/ml or 10 g/ml it could be assumed to be non-physical and rejected. Another important example for this rejection criterion is for contrast pharmaceuticals, where the lowest acceptable solution can be set to be the lowest detectable concentration that is measurable by the given multi-energy CT system.

---
Algorithm 2.0 Combinatorial Material Decomposition (CMD)
---

Set maximum sparsity level k.
Calculate all combinations of 1, . . . , k materials.
Set combinations to be excluded.
Set allowed solution range for each material.
Assign each combination r with the corresponding sub-material matrix $M_r$.
for (each voxel $v_i$ in reconstructed volume) do
    Set initial best square error $\varepsilon_{best} = 10^6$ (or some other very large number)
    Set initial best solution $x_{best} = \vec{0}$.
    for (each combination r) do
        if (combination not excluded) then
            Calculate the non-negative least square estimate x of the system $M_r x = b$.
            if ($\|M_r x - b\|_2^2 < \varepsilon$ and solution is in allowed range) then
                Set $x_{best} = x$ and $\varepsilon_{best} = \|M_r x - b\|_2^2$.
            end if
        end if
    end for
    Set the solution to $v_i$ to be $x_{best}$.
end for

---

The CMD algorithm can be used for material decomposition of experimental data into six materials using only four energy bands. For comparison, the CMD result is compared to results obtained from using linear least squares and non-negative linear least squares material decomposition methods (with the same data and material basis).

Figure 11:
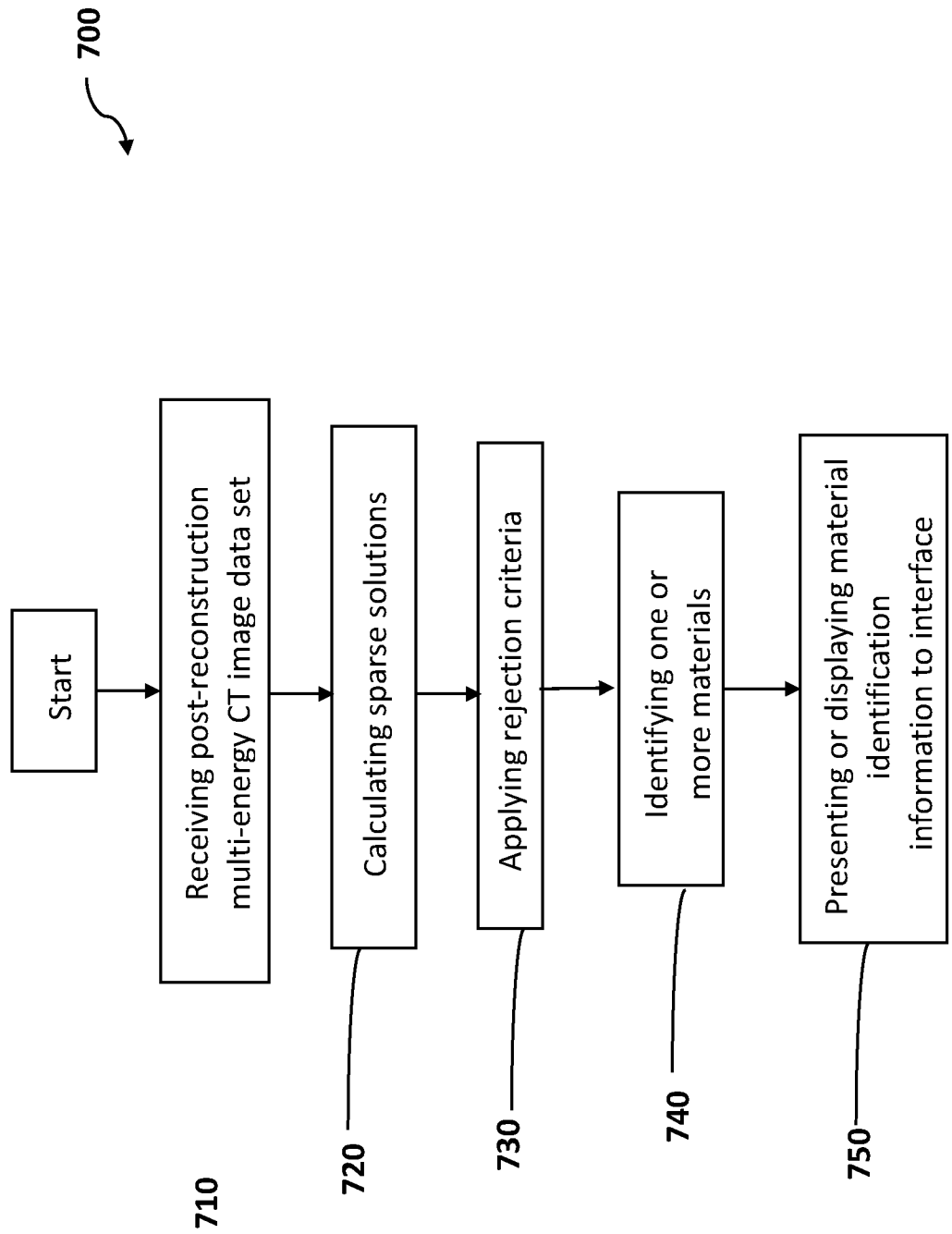
FIG. 11 shows a computer implemented method for the identification of materials within an object method in one embodiment of the invention.
Figure 12:
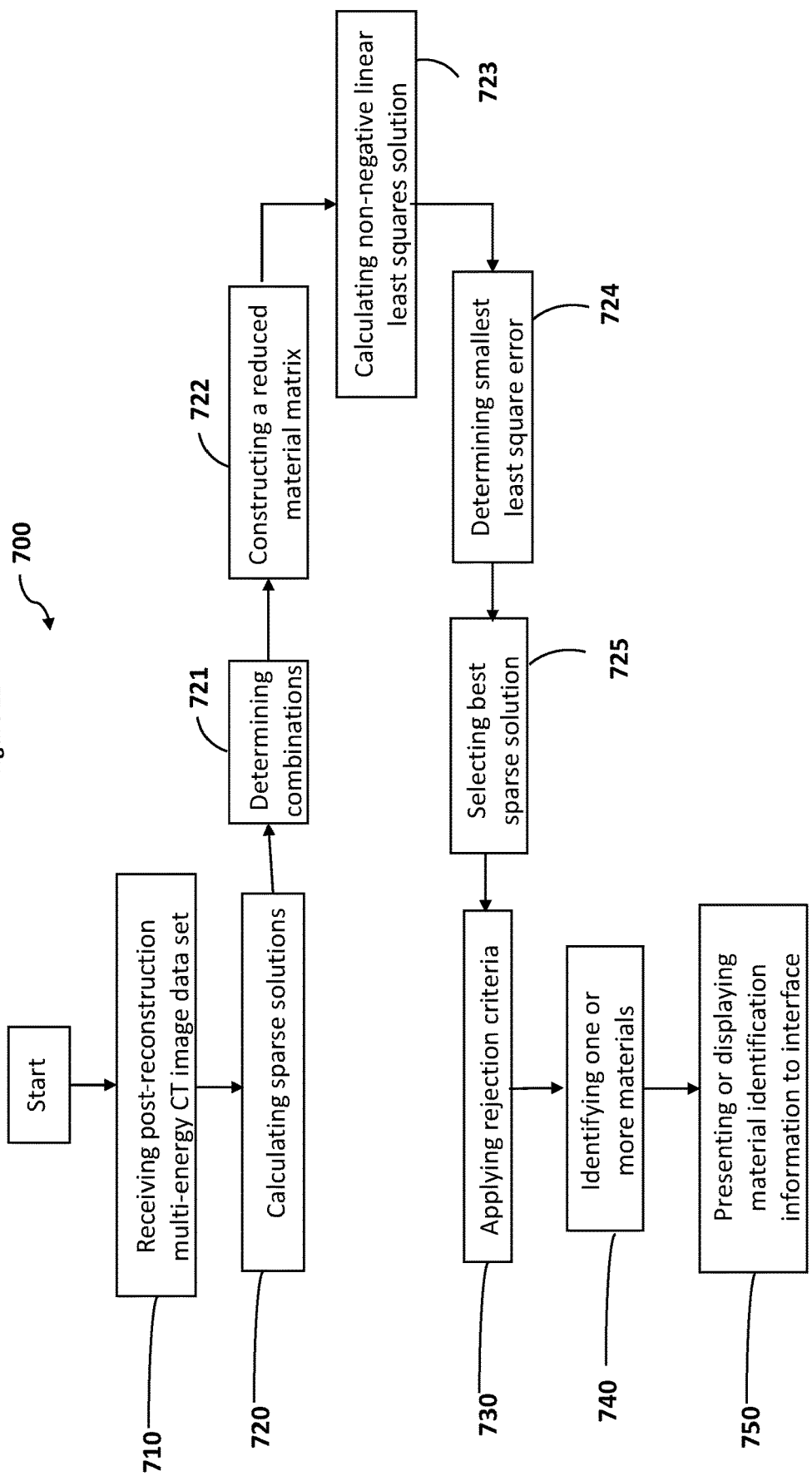
FIG. 12 shows the computer implemented method of FIG. 10 with further detail on the calculation of sparse solutions.
Figure 13:
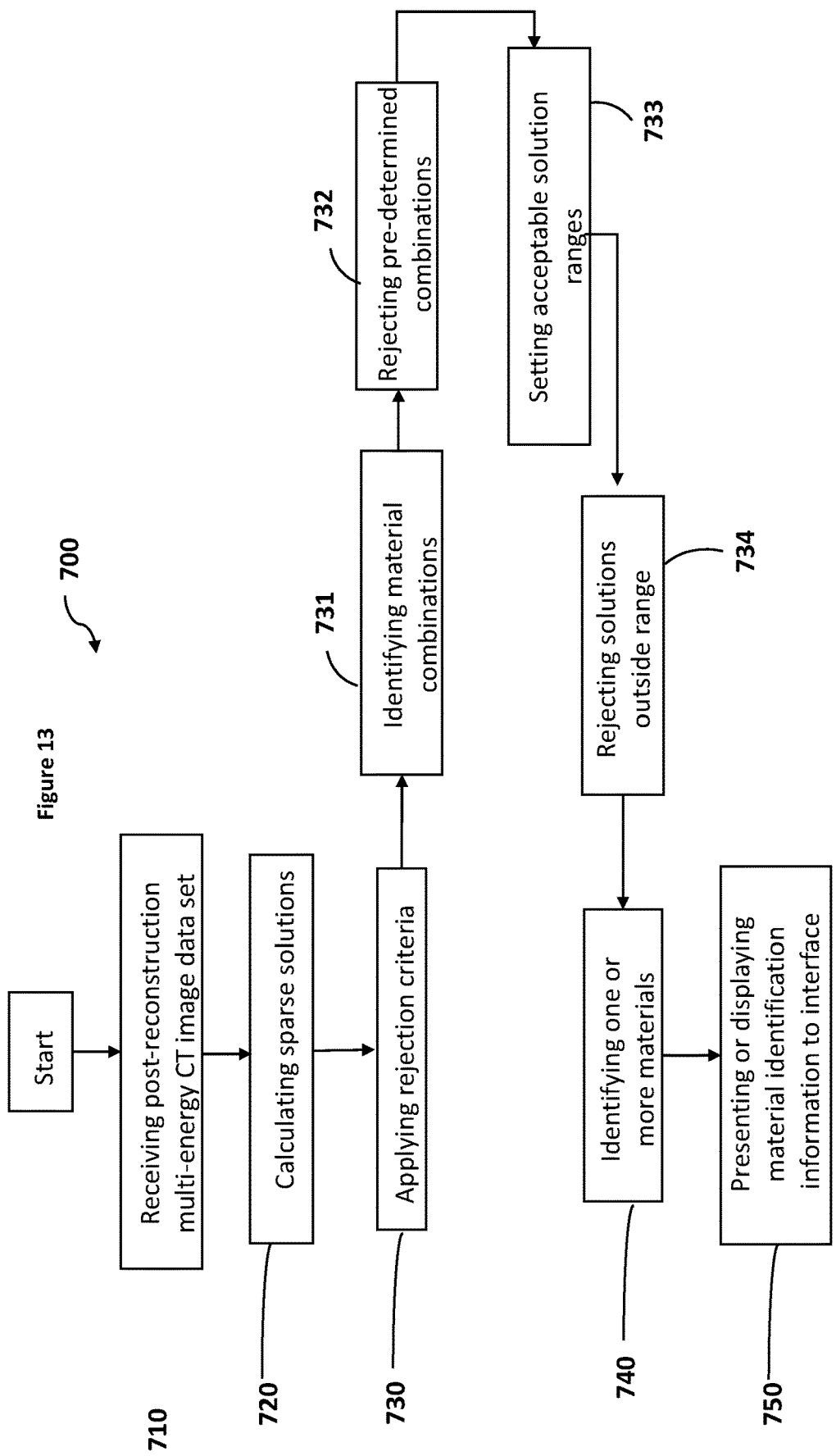
FIG. 13 shows the computer implemented method of FIG. 10 with further detail on the application of rejection criteria.
Figure 21A:
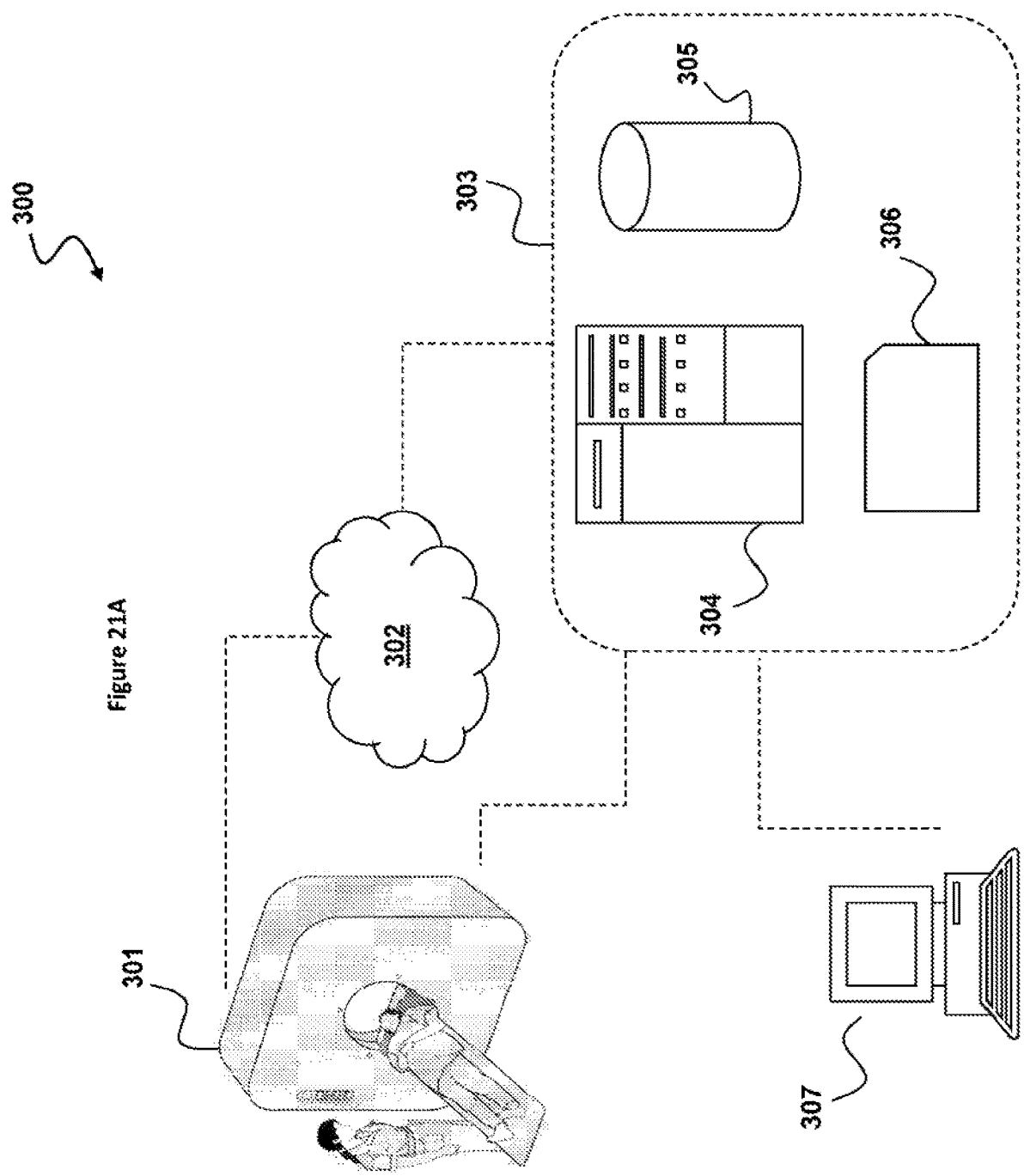
FIG. 21A shows a representation of one embodiment of a system for implementing any one or more of the methods shown in FIG. 2, 11-13 or 21.
Figure 21B:
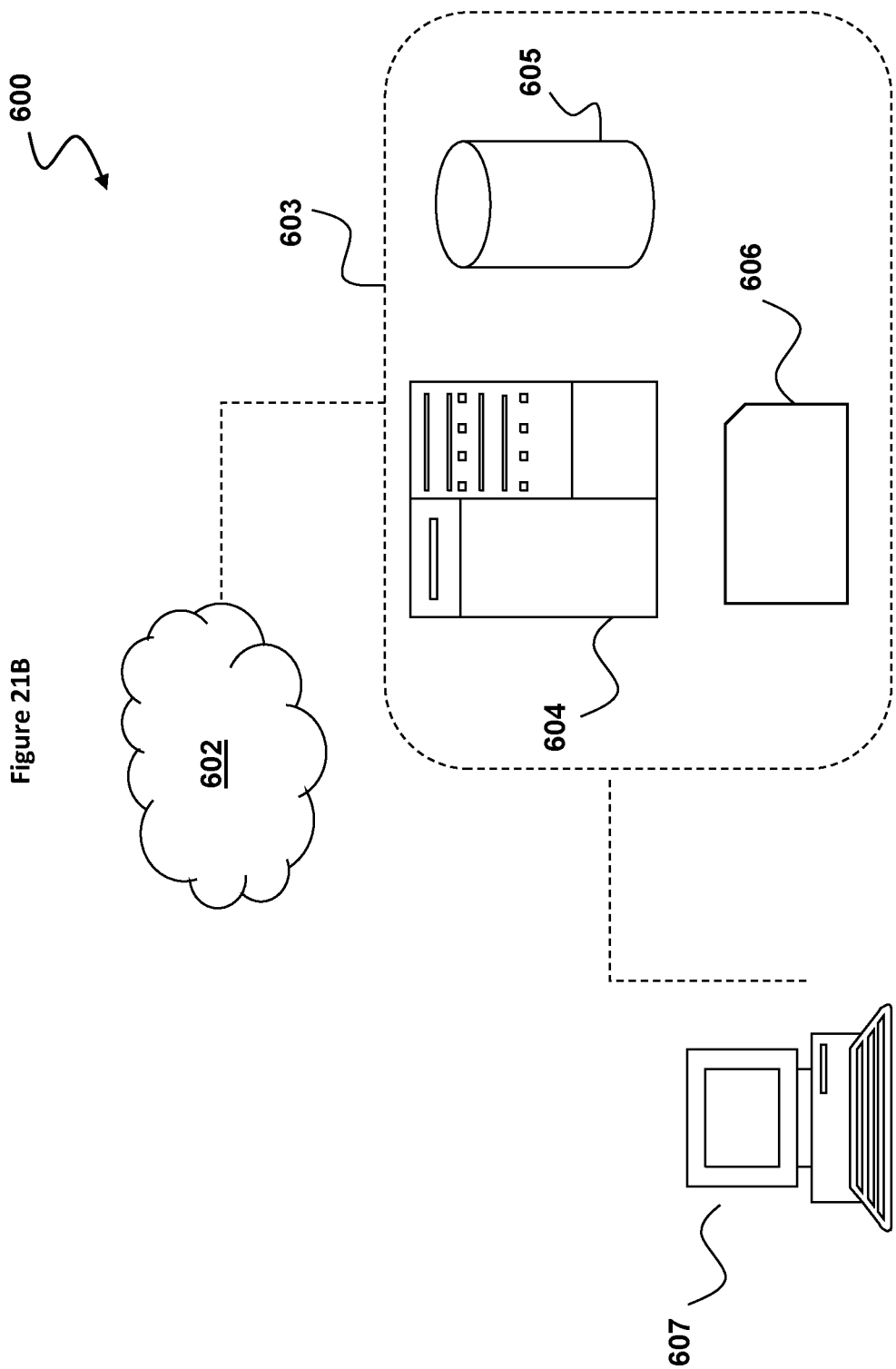
FIG. 21B shows a representation of an alternative embodiment of a system for implementing any one or more of the methods shown in FIG. 2, 11-13 or 21.
Figure 22:
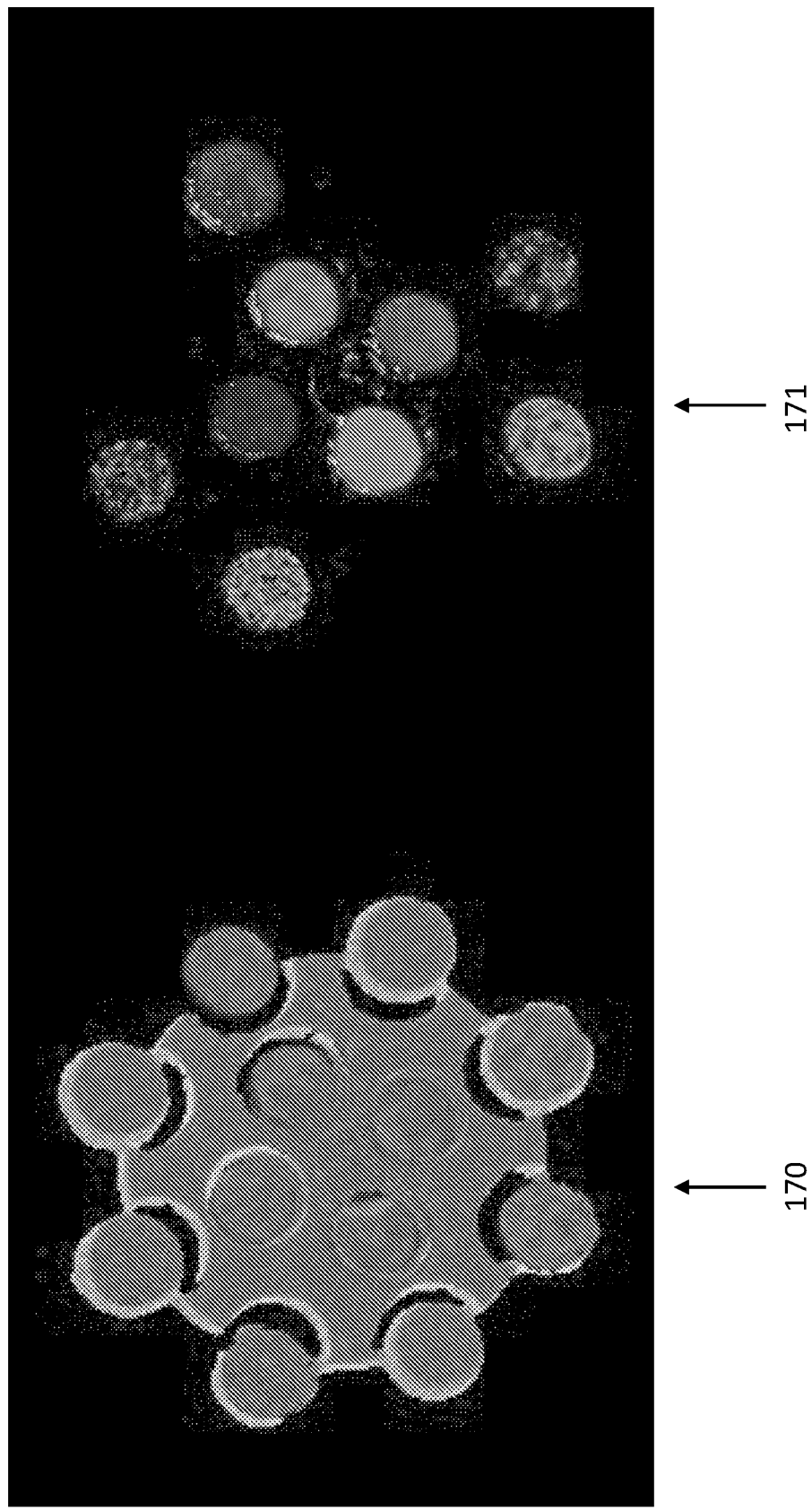
FIG. 22 shows representations of multi-contrast phantom MARS-MD decomposition.

The CMD algorithm in use as implemented by a computer software program can be seen in by method 700 in FIGS. 11-13. The methods described here may be carried out on one or more of the systems as shown in FIGS. 21A and 21B and described in further detail below.

As seen in FIG. 11, a multi-energy CT image data set is received by a processor 710. It is envisaged that the image data set may be generated within a system incorporating the processor described herein, or received over a network from an external system.

At 720 the processor then calculates, for each of the reconstructed voxels contained within the data, a sparse solution for a maximum number of material combinations using 0-norm minimisation. FIG. 12 provides further detail on the method steps for calculating sparse solutions, as represented by steps 721-725 and described using formula 4.4 above.

At 721 all combinations of the maximum number of materials present in the image data set are determined, including the determination of combinations of fewer than the maximum number of materials. For each combination, a reduced material matrix $M_r$ is constructed 722, then a non-negative linear least squares solution $x_r$ for the sub problem $M_r x_r =$ one voxel is determined at 723.

Determination of which solution from 723 has the smallest least square error out of all the tested combinations determined at 721 is then calculated and the best sparse solution 725 is determined. The best sparse solution is determined as the combination with the smallest least square error out of all the tested combinations.

Following the selection of the best sparse solution at 725, rejection criteria is applied to reject solutions which either are non-physical or consist of an unlikely combination of materials. FIG. 13 sets out the specific steps in further detail as 731-734 which are described further below.

Step 731 includes identifying material combinations that are pre-determined not to be found in the same voxel by comparison with information on the pre-determined combinations. Pre-determined material combinations may be stored in a database within the system of the present invention and may also include external databases, for example those accessed using the internet. Once identified, material combinations not to be found in the same voxel based on 731 are rejected 732.

Following rejection of pre-determined material combinations at 732, acceptable solution ranges are set for each material 733. The acceptable solution ranges will be set according to the object of materials being imaged and the common general knowledge around acceptable measurements for the object or sample of interest, as outlined by the examples given earlier in the description. The solution ranges should be taken as approximations and are designed in order to eliminate clear outliers, rather than those that are substantially near the range extremities. Solutions found substantially outside the acceptable ranges are rejected 734.

Following rejection of unsuitable data solutions, materials represented by the image data are determined 740 and the resulting information presented to a user interface 750. Examples of such user interfaces include graphical user interfaces or visual user interfaces including one or more monotone (grey scale or single colour) images, where the intensity is proportional to quantity in a voxel; and multi-colour images with different colours representing different materials.

The transform from the mathematical solutions to the material-quantified CT image can be obtained by, for example, allocating each material to a specific colour or a separate image. A 2D grey scale image is naturally described by a matrix of numbers proportional to the brightness of each pixel. Since the CMD algorithm constructs matrices of the contents of voxels, one for each of the basis materials, any 2D slice of the volume gives a matrix that can be displayed, one image per material. A set of such images can be visually represented by specific and distinctive colours, and if the solution is sufficiently sparse, the different coloured images combined into a single multi-colour image.

An example of the CMD algorithm outlined by FIG. 11-13 is given below.

Multi-Contrast Phantom Dataset

Figure 14:
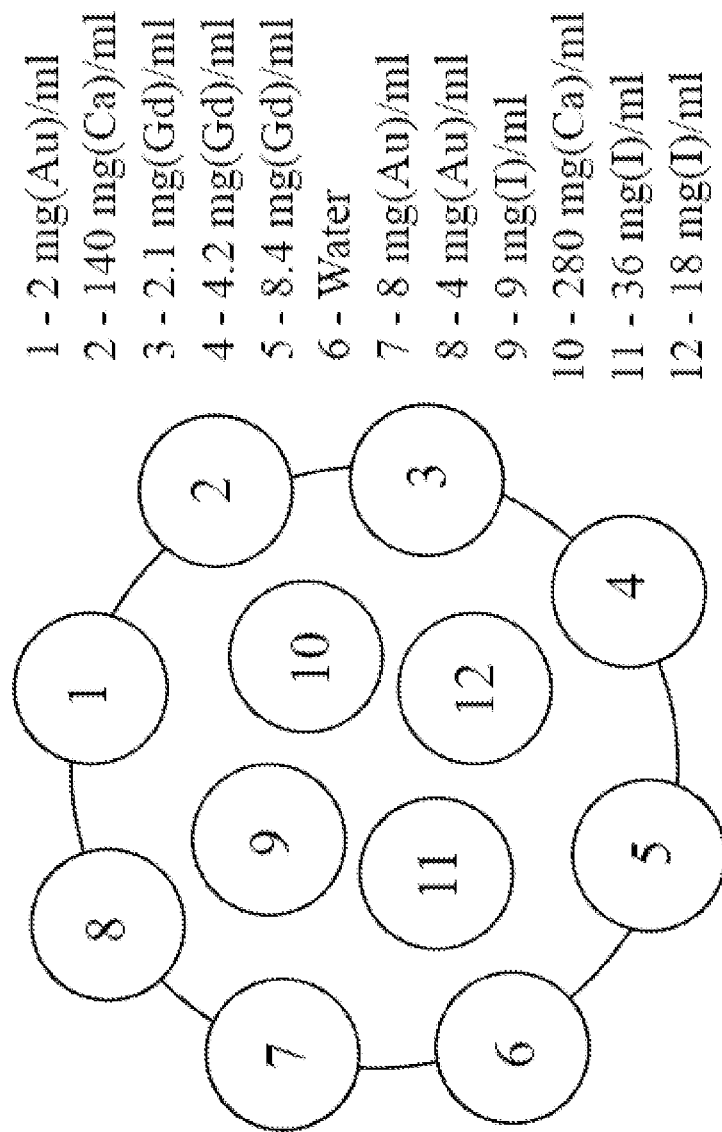
FIG. 14 shows a multi-contrast phantom layout with capillaries containing solutions of five different materials: Au nano-particles, Magnevist™ (gadolinium) and Omnipaque™ (iodine) contrast pharmaceuticals, CaCl2, and water.

A multi-contrast phantom consisting of a solid polymethyl methacrylate (PMMA) cylinder with four capillaries drilled in the middle and eight around the outer edge was prepared. Samples contained in small polymerase chain reaction tubes (PCR tubes) were inserted into each of the capillaries. Solutions for these capillaries are shown in FIG. 14 and include Au nano-particles at 2, 4, and 8 mg (Au)/ml; Magnevist™ (gadolinium based contrast pharmaceutical) at 2.1, 4.2, and 8.4 mg (Gd)/ml; Omnipaque™ (iodine based contrast pharmaceutical) at 9, 18, and 36 mg (I)/ml; CaCl2) at 140, and 280 mg (Ca)/ml; and water.

Figure 15:
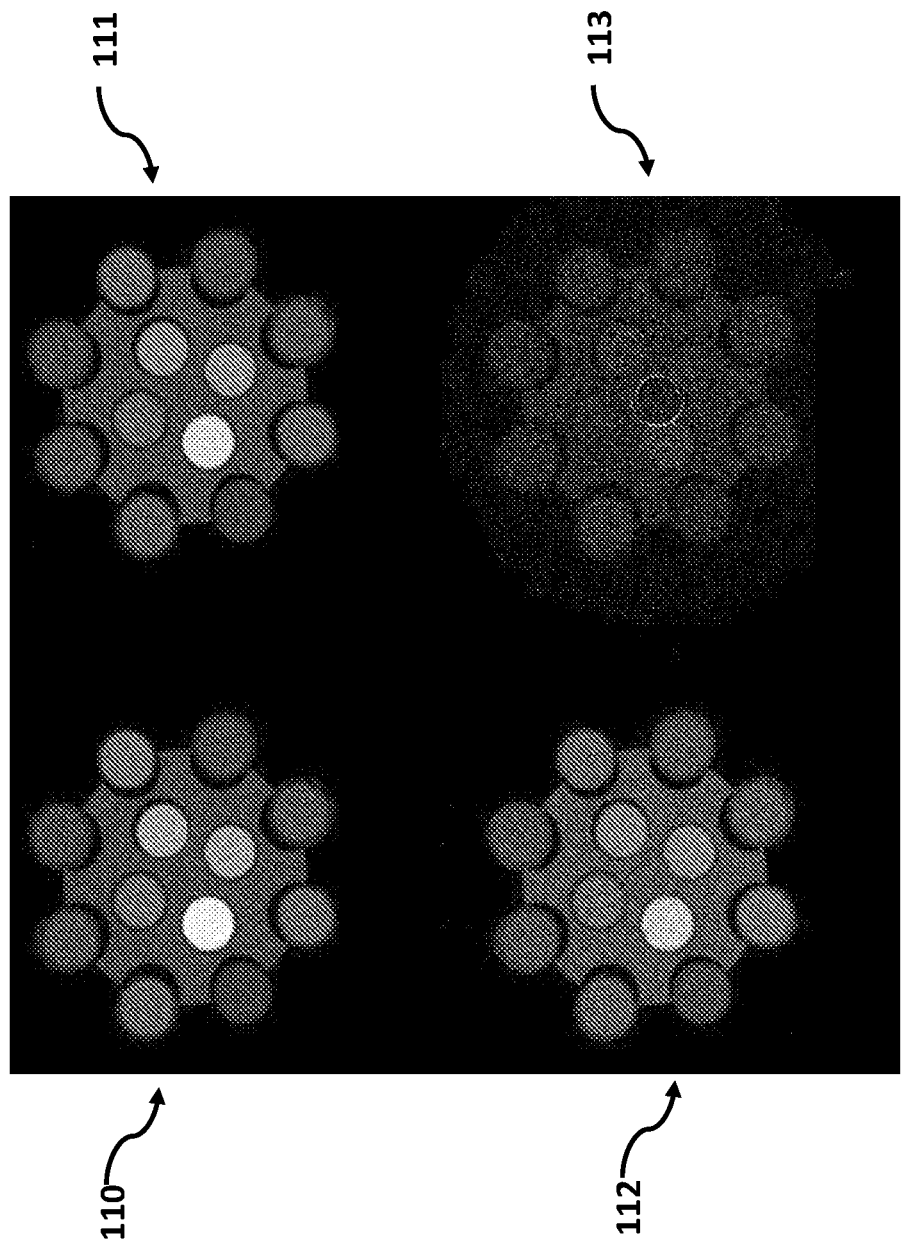
FIG. 15 shows a multicontrast phantom slice 12 following algebraic reconstruction.

The phantom was scanned using a CdTe-Medipix-3RX camera operating in charge-summing mode and a 120 kVp tungsten x-ray tube. Four energy bands were acquired at ranges of 27-120 (110 on FIG. 11), 33-120 (111), 55-120 (112), and 81-120 (113) keV. Each energy band was reconstructed independently using an algebraic reconstruction technique. Slice 12 of the reconstruction is shown in FIG. 15.

The basis for material decomposition consisted of effective mass attenuation coefficients calculated from the reconstructed images. Six materials were chosen: the five capillary materials—calcium, gadolinium, gold, iodine, and water (using the median of 1920 voxels each); and the PCR tube plastic was chosen for an estimate for lipid (using the median of 420 voxels).

The CMD algorithm was used for material decomposition into the six material basis using only the allowed combinations of materials: lipid and water, individual dense material (calcium, gadolinium, gold, and iodine), and dense material with water. No bounds were placed on the solution range (i.e. an allowed range of 0→∞ for each material). The data for each energy range was de-noised prior to decomposition by averaging together five adjacent images and applying a cylindrical median filter with a circle radius of 1 voxel (2 voxels for the 81-120 keV band).

Figure 16:
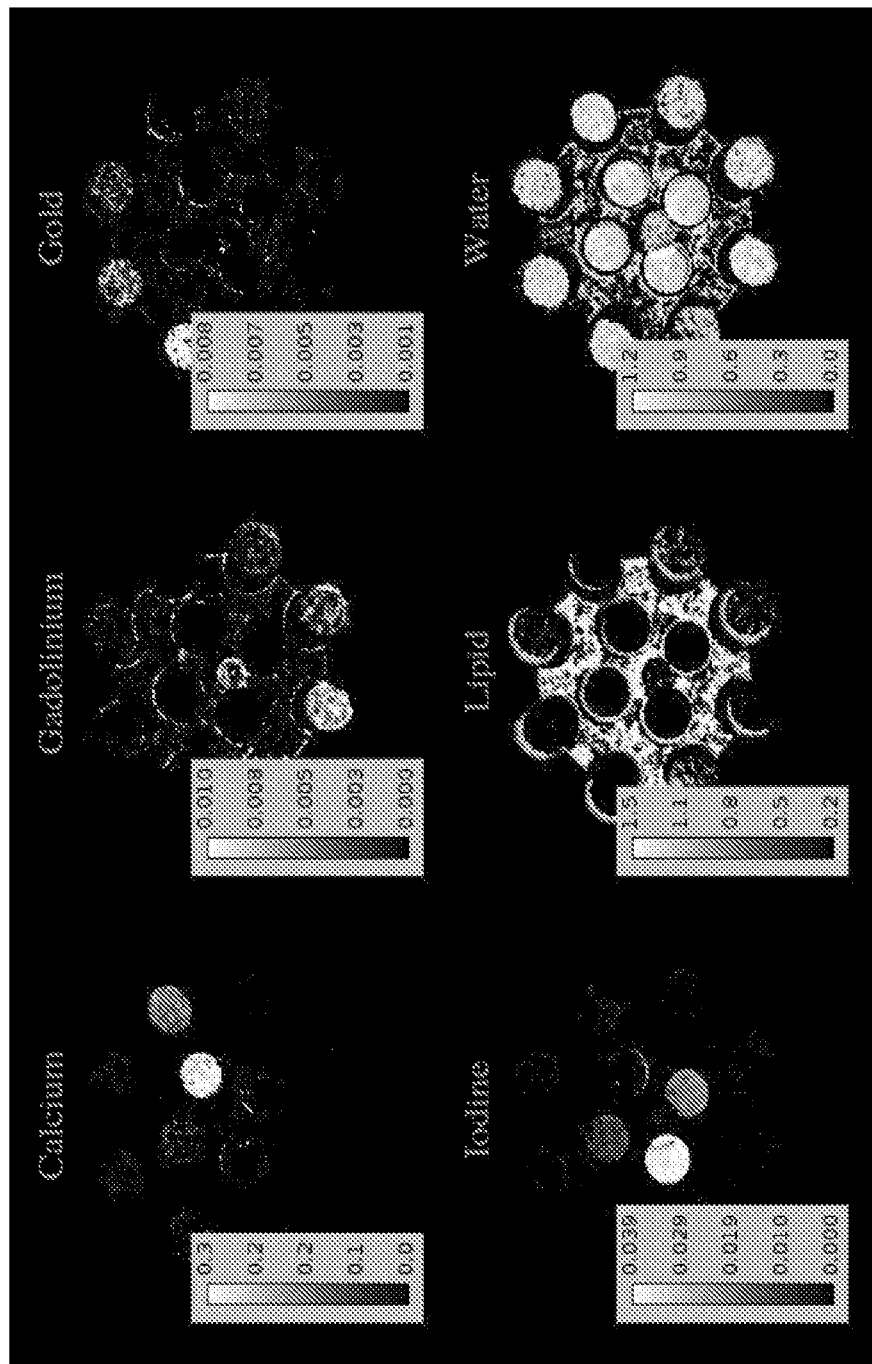
FIG. 16 shows the combinatorial material decomposition of a multi-contrast phantom, with the scale for each material in g/ml.
Figure 17:
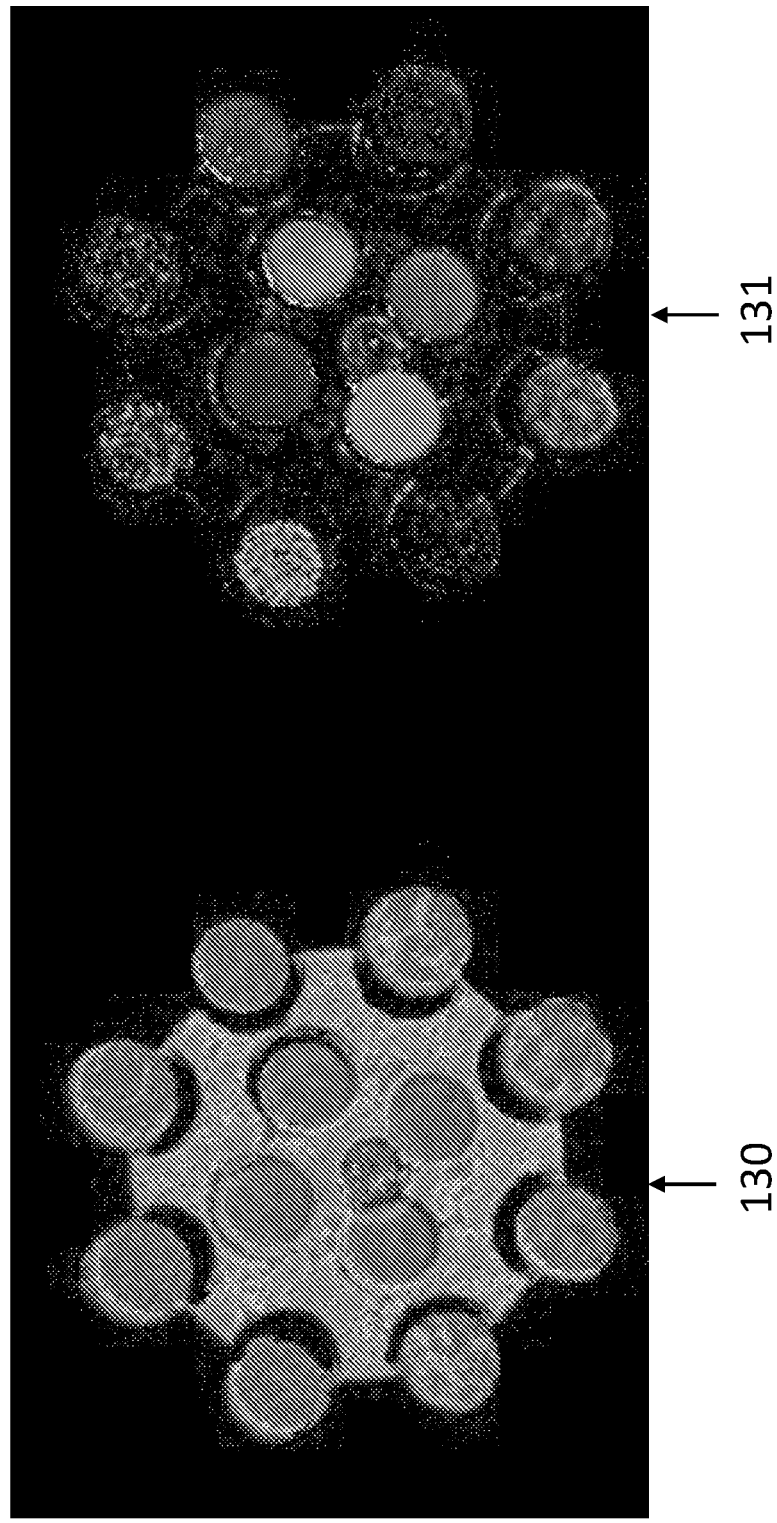
FIG. 17 shows the representations of multi-contrast phantom CMD decomposition comparing soft tissue and dense material.

The material decomposition result, shown in FIG. 16, has performed well by identifying all dense materials and water in the capillaries. A significant proportion of the PCR tube was also identified correctly in the lipid image. PMMA however was identified mostly as pure lipid with a density of 1.5 g/ml which is a non-physical result (pure lipid typically has a density in the range 0.90-0.95 g/ml). There was also a minor misallocation of dense materials across the image, the most prominent being gadolinium in PMMA. A representation of the decomposition is provided in FIG. 17, showing soft tissue 130 and dense material 131.

Moore-Penrose Pseudo Inverse and Non-Negative Linear Least Squares

For comparison, material decomposition on the same data was performed using two basic methods, linear least squares and non-negative linear least squares. Linear least squares was performed using the Moore-Penrose pseudo inverse $M^+=(M^TM)^{-1}M^T$. The material matrix used in both of these decompositions consisted of all six materials mentioned above (and 4 energies) used in the CMD decomposition. The results of these two methods are shown in FIGS. 18 and 19.

Figure 18:
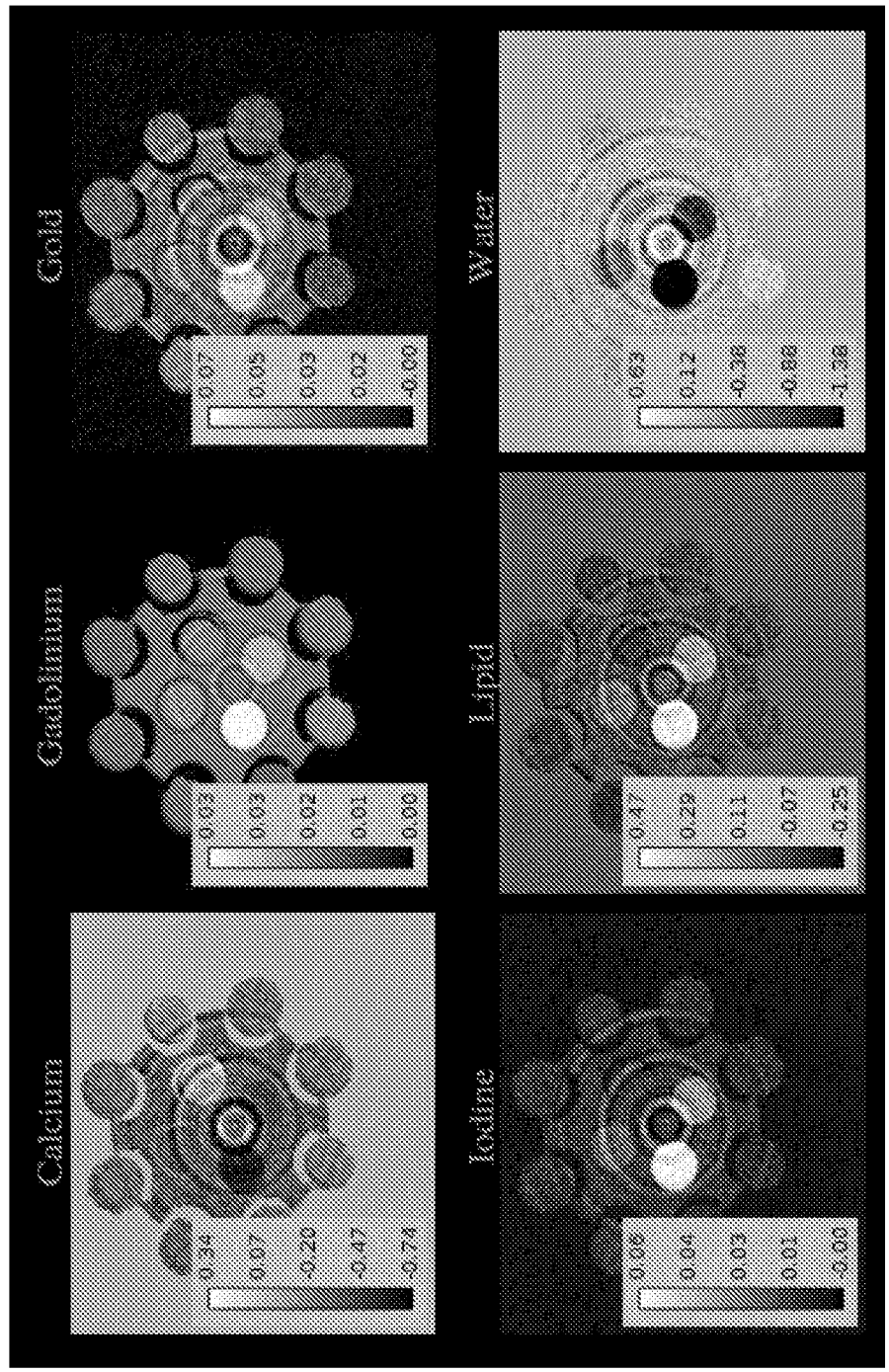
FIG. 18 shows the linear least squares material decomposition of multi-contrast phantom, with the scale for each material in g/ml.

FIG. 18 shows the results of the Moore-Penrose psuedo inverse (linear least squares) for each of the six materials used.

Figure 19:
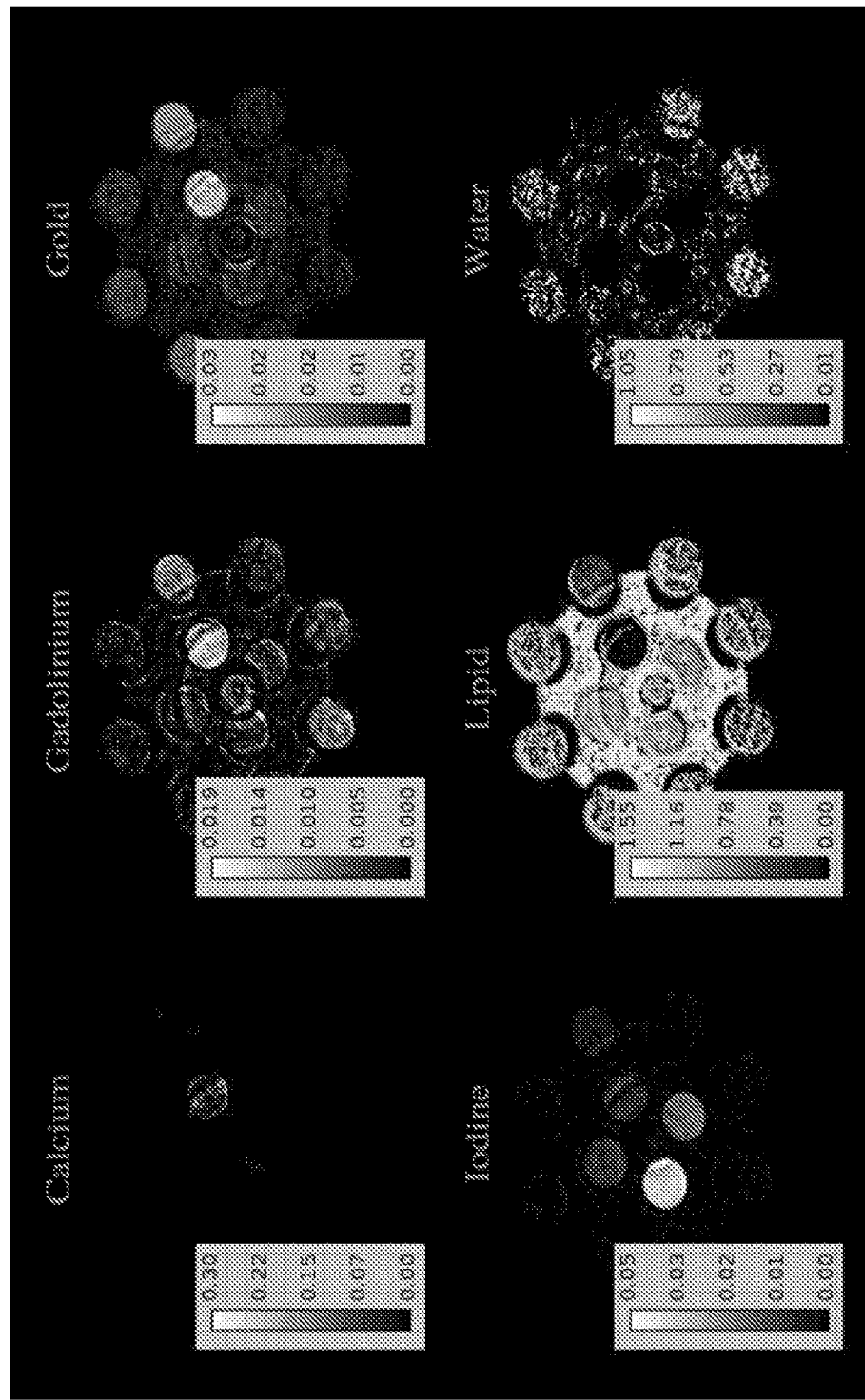
FIG. 19 shows the non-negative linear least squares material decomposition of multi-contrast phantom, with scale for each material in g/ml.

FIG. 19 shows the results of the non-negative linear least squares analysis for each of the six materials used.

It is clear from these results that both methods are unable to identify all six materials simultaneously. The linear least squares method both has highly negative results for some materials, and each voxel is given a significant allocation of almost every material (resulting in a copy of the entire phantom shown in each material image). However, this result is not surprising since the material matrix has fewer rows than columns. The non-negative linear least squares has performed slightly better than linear least squares at separating the lipid-water like part of the signal from the dense material part of the signal, however there is still significant mismatch between the dense materials.

The combinatorial material decomposition algorithm presented in this section is designed to aid material identification by enforcing a sparse representation of the material composition for each voxel. CMD does this by taking a large ill-conditioned material matrix and breaking it up into a set of smaller better conditioned material matrices, which are better suited for inversion. This method enables multi-energy CT data to be decomposed into a great number materials using few energy ranges, without inclusion of the volume or mass fraction conservation constraints.

The decomposition on the multi-contrast phantom using CMD, as seen in FIG. 16, shows that a reasonable six material decomposition with four energy bands can be achieved by enforcing a limit on the total number of materials allowed in a voxel. Minor misallocation of materials is observed (particularly in the lipid and gadolinium material images), however in general all material regions are well distinguished.

When compared to the results of the linear least squares and non-negative linear least squares decompositions, which significantly fail to separate any single material, the CMD result can be considered a success.

An advantage of the CMD algorithm structure is that further constraints can easily be enforced on individual material combinations. For example using either volume/mass fraction conservation or allowed solution ranges. Additional constraints can reduce the amount of material misallocation to improve the accuracy of the decomposition. The use of additional constraints will be shown in later in the description with the MARS-MD algorithm.

The CMD allowed concentration range for each material was not set in the above multi-contrast phantom example so as to demonstrate the potential of using algorithms for material decomposition that find sparse solutions. This constraint was originality devised to constrain calcium to the concentration range of bone to pre-empt any problems which may occur when comparing materials such as lipid, water and calcium (which do not have a K-edge in the diagnostic imaging range). In practice, this constraint only ever needs to be set when testing the algorithm on data with a high degree of noise.

The MARS-MD Algorithm

The MARS-MD algorithm uses SST to separate low attenuating soft tissue materials from high attenuating dense materials, enabling each case to be decomposed using a different material decomposition algorithm. The motivation for this approach is that suitable algorithm constraints can be picked specifically for each group of materials. For example, the volume conservation constraint is a good approximation for soft tissues (which is primary composed of lipid and water) but is violated for high concentrations of contrast pharmaceuticals (where the density of water changes due to electrostatic forces exhibited from heavy atoms in the contrast). The MARS-MD algorithm improves on the CMD algorithm by adding appropriate constraints to specific combinations of materials.

Three classes of voxels are identified using SST—air, soft tissue, and dense material. Air voxels are treated as empty by the MARS-MD algorithm. Soft tissue voxels are approximated as a combination of lipid and water and are assumed to satisfy volume conservation (since lipid can only dissolve in water through emulsion). Dense material voxels are considered to contain either a dense solid material (i.e. bone or metal) or contrast pharmaceutical in solution (i.e. iodine contrast in blood). Since lipid and water have similar attenuation properties they are approximated to contribute to the same material signal (water) if the voxel is classified as containing dense material.

The MARS-MD algorithm defined below can be summarised by the following steps: The SST algorithm is used to determine if a voxel contains soft tissue or dense material. If a voxel is identified as soft tissue then the voxel is decomposed into lipid and water using volume constrained non-negative linear least squares. If the voxel is identified as dense material then it is decomposed using the CMD algorithm. The material combinations checked in the CMD calculation include each dense material individually and each dense material paired with water. The acceptable solution range for each material in CMD is left unset (i.e. will allow solutions from $0 \rightarrow \infty$) in the version of MARS-MD as disclosed herein, although this is not intended to be limiting.

---

Algorithm 3.0 MARS-MD algorithm

---

Set CMD algorithm allowed material combinations, $\mathcal{M}$, to be individual dense materials and those materials paired with water.
Use SST algorithm to categorize voxels into either air, soft tissue, or dense material.
for (each voxel $v_j$ in reconstructed data) do
    if ($v_j$ assigned to air) then
        Set voxel solution to $\vec{0}$.
    end if
    if ($v_j$ assigned to soft tissue) then
        Decompose voxel into lipid and water using volume constrained non-negative linear least squares.
    end if
    if ($v_j$ assigned to dense tissue) then
        Decompose voxel using CMD algorithm with material combinations $\mathcal{M}$ and the allowed solution range $0 \rightarrow \infty$.
    end if
end for

---

The MARS-MD algorithm 800 as a computer implemented method is summarised in FIG. 21.

In the method described in FIG. 21, image data from a multi-energy CT scan is received by a processor. It is envisaged that multi-energy CT image data may be generated from a scanning system directly linked to the processing system, or received from a remote location via a network. Image data is received by processor 810 then if non-reconstructed, is reconstructed 820 using known data reconstruction techniques, for example an algebraic reconstruction technique, to produce a set of reconstructed voxels.

Reconstructed voxel data is then compared to a reference set of material signal amplitude and noise properties 830 stored in a database and the voxels then classified 840 into air 850, low density 870 or high density 880 voxels based on comparison with the reference set.

If the voxel is classified as air then the voxel is given a solution of zero attenuation and are exempt from further analysis. Voxels classified as low density 870 undergo application of volume constrained non-negative least squares calculation to aid in material identification. Volume constrained means that the volume fraction of lipid plus the volume fraction of water is at most 1. The volume is constrained to "at most 1" as there may be some air in the volume, such as in the lungs or in a voxel at an air-tissue boundary.

Voxels classified as high density 860 undergo further processing steps associated with the CMD algorithm as discussed above and shown in further details as steps 720-725 in FIG. 12 and steps 730-734 in FIG. 13.

Based on the results of the in steps 810 through to 871, identification of one or more specific materials is established and the information communicated to a user interface.

As with above, examples of such user interfaces include graphical user interfaces or visual user interfaces including one or more monotone (grey scale or single colour) images, where the intensity is proportional to quantity in a voxel; and multi-colour images with different colours representing different materials.

We can further compare the performance of the MARS-MD algorithm to the CMD algorithm. The first comparison shows that the MARS-MD algorithm improves on the six material decomposition of the multi-contrast phantom dataset presented for the CMD algorithm. A second comparison of these algorithms using a dataset named FatCaFe is presented to demonstrate the benefit that the segmentation component of MARS-MD has for reducing incorrect allocation of soft tissue materials as dense materials.

Figure 20:
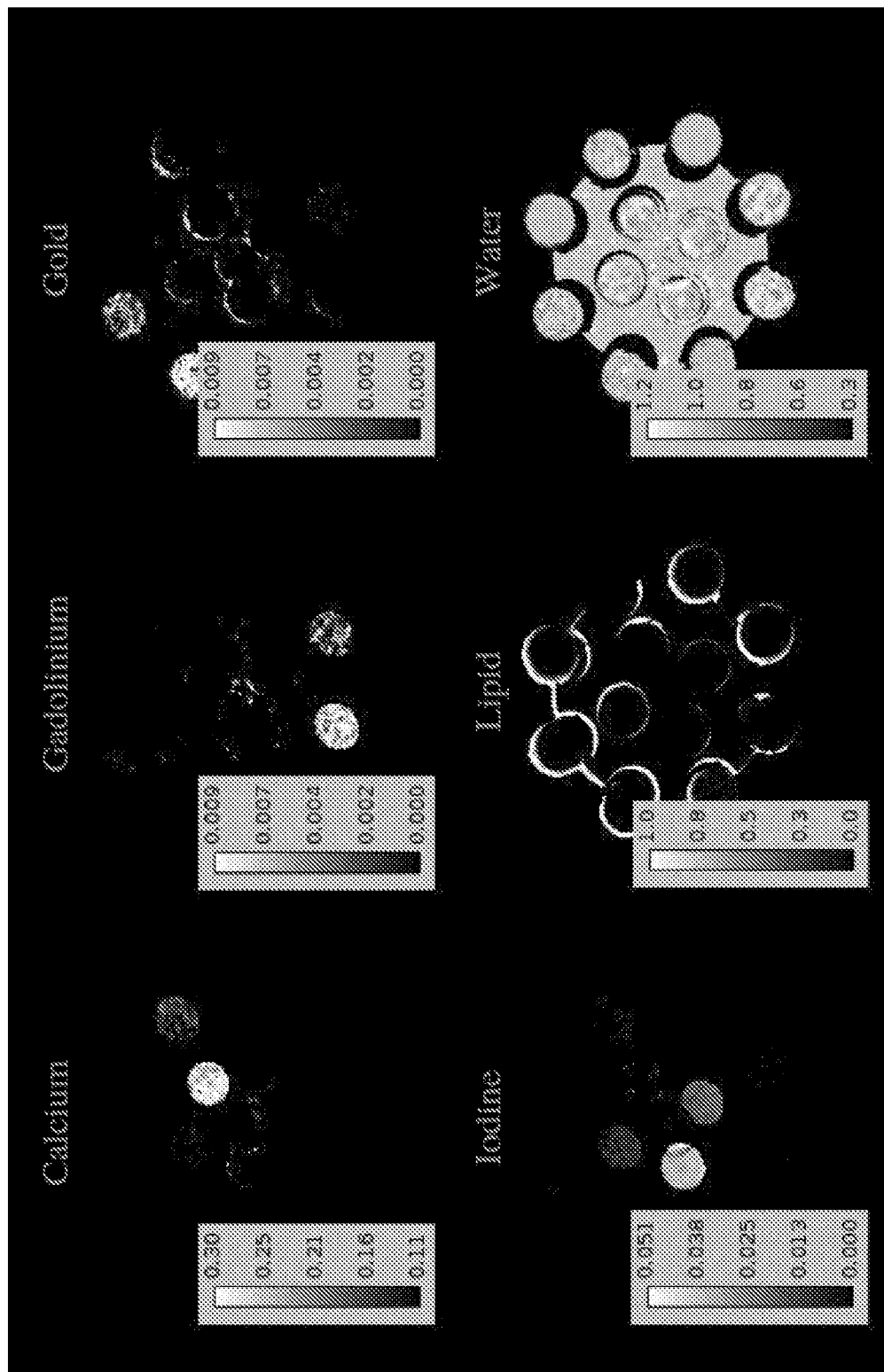
FIG. 20 shows the MARS-MD material decomposition of multi-contrast phantom, with the scale for each material in g/ml.

To show the general performance of the MARS-MD algorithm compared to the CMD algorithm it has been applied to the multi-contrast phantom dataset presented above for CMD (see FIG. 14) using identical image and material basis inputs. The covariance matrix for the MARS-MD algorithm was estimated from a large homogeneous region of air voxels. The results of the material decomposition algorithm using the MARS-MD algorithm is shown in FIG. 20, and a further representation of this is given in FIG. 22, where 170 shows the soft tissue MD and 171 shows the dense material MD.

The differences between the MARS-MD and CMD algorithms are in the segmentation to separate dense and soft tissue voxels, and the addition of a volume fraction conservation constraint on the lipid-water combination. Therefore any voxels identified as dense material will decompose exactly the same as they did in CMD; and soft tissue voxels are expected to have physically plausible solutions (unlike the 1.5 g/ml lipid solution from the CMD algorithm).

The lowest concentrations of gold and gadolinium in this decomposition example have been identified as water. This result is due to the SST segmentation identifying those concentrations to be indistinguishable from water in regards to the level of noise in the data. However, another consequence of the segmentation is that there is significantly less misidentification of dense materials in the water capillary and PMMA region.

There is significant improvement in the allocation of lipid and water in this decomposition compared to the CMD decomposition. The lipid image only identifies PCA tube plastic and edge blurring artifacts from the median filter. The water image shows water in every capillary. The lipid-water decomposition is also observed to be more robust due to the homogeneous allocation of water to PMMA.

Figure 23:
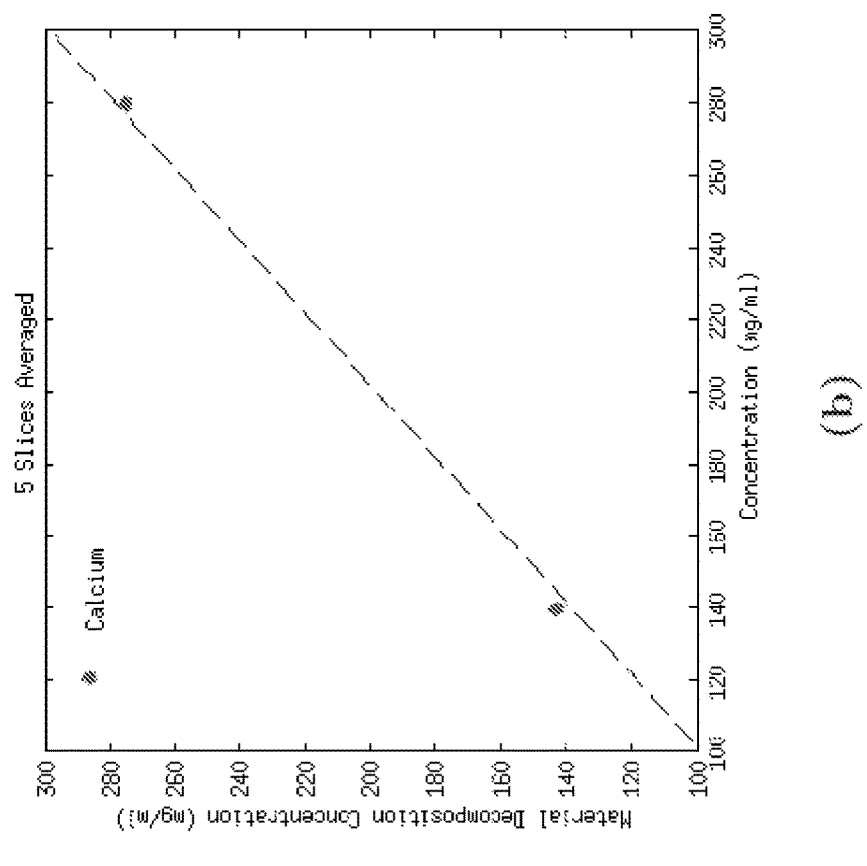
FIG. 23 shows material decomposition concentrations compared to the known concentrations of each dense material.
Figure 23:
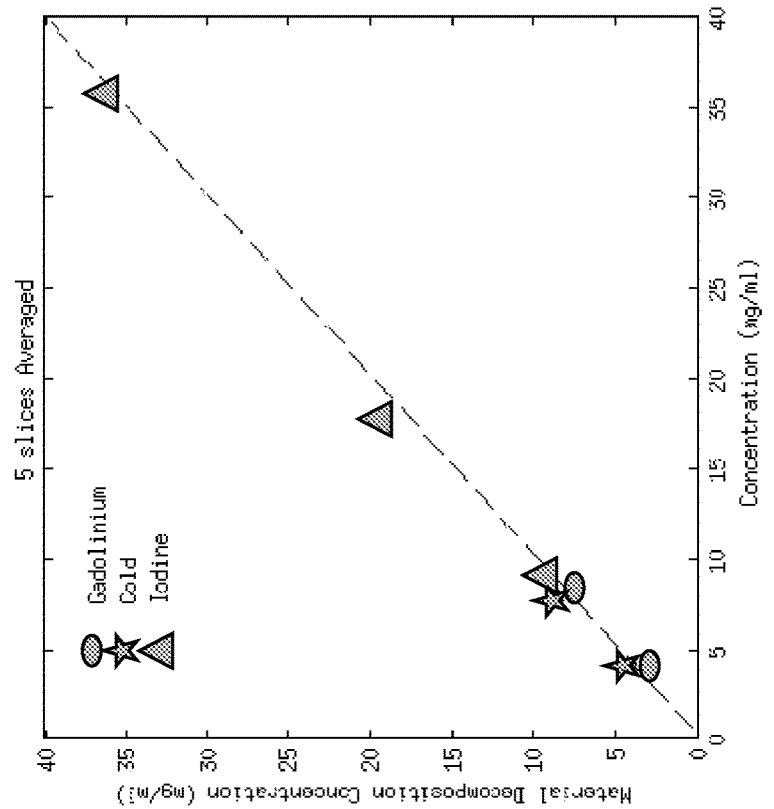

The median concentrations of each dense material region in the decomposition (from the material decomposition) were compared to the known concentrations of each solution as seen in FIG. 23, excluding the two concentrations which were identified as soft tissue. This result shows reasonable accuracy of the MARS-MD algorithm for this dataset. It should also be noted that this result will be the same for the CMD algorithm.

FatCaFe Phantom

FatCaFe is a known phantom dataset consisting of a solid PMMA cylinder with 6 capillaries filled with the materials: 2.0 mol/L CaCl2) solution, 0.4 mol/L Fe(NO3)3 solution, 0.01 mol/L iodine solution, sunflower oil, water, and air. Data was collected using a Medipix-3 (Si) quad detector; a 50 kVp tungsten x-ray beam; and measured using six energy bands (9.8-50, 15.1-50, 20.4-50, 25.6-50, 30.9-50 and 36.2-50 keV).

Figure 24:
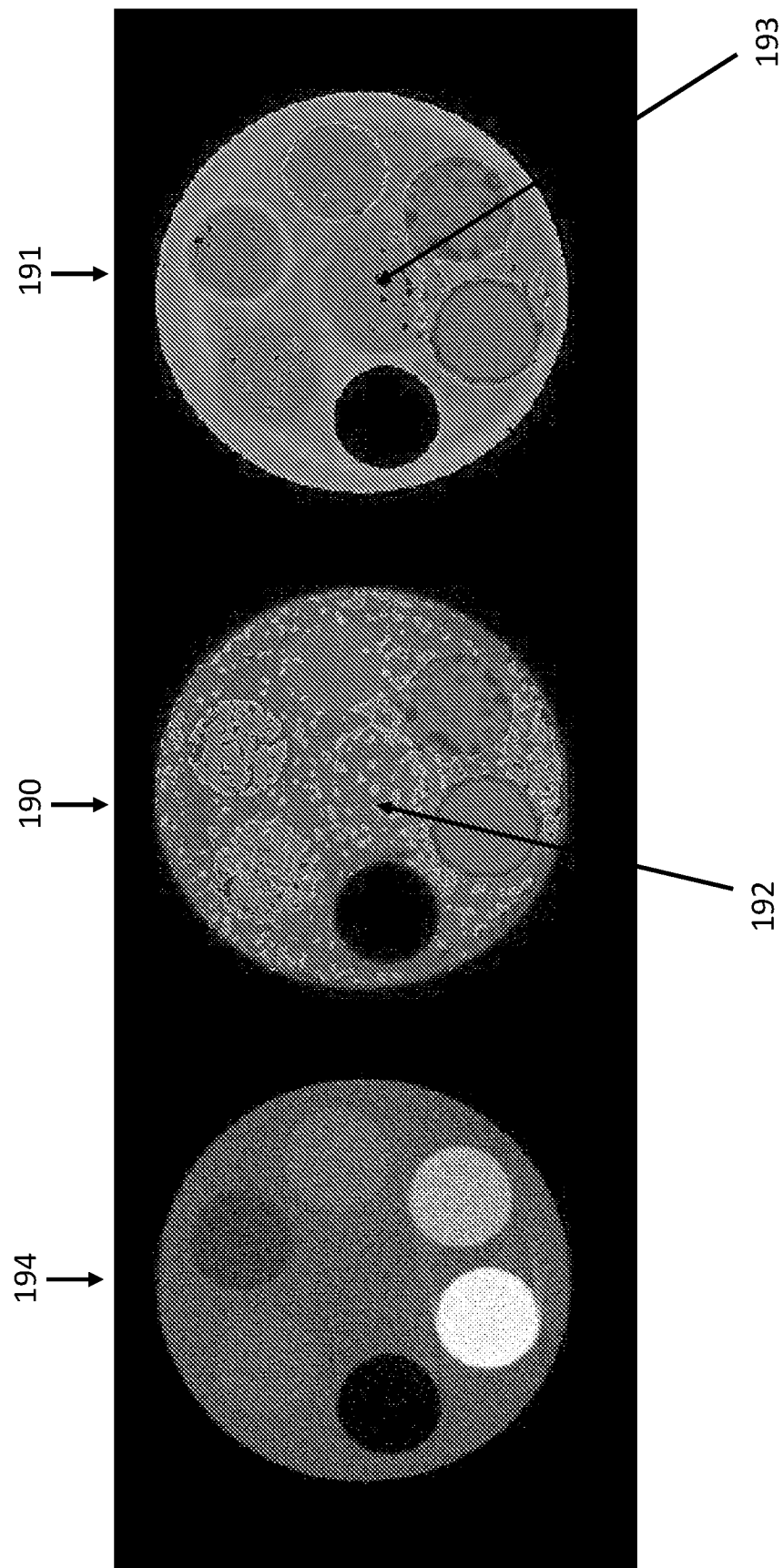
FIG. 24 shows a FatCaFe dataset and associated material decompositions using both CMD and MARS-MD.

Material decomposition of this dataset using CMD 190 and MARS-MD 191 algorithms are presented in FIG. 24 together with reconstructed image 194 which shows the differences in material identification using the different decomposition methods. The benefit of the segmentation step in the MARS-MD algorithm can be observed from the misidentification of PMMA as iodine in the CMD decomposition at position 192, when compared to the MARS-MD decomposition, where PMMA is correctly identified at position 193 as shown by the shaded circle which was absent at 192.

In one preferred embodiment of the invention, the MARS-MD algorithm disclosed is implemented using MATLAB program developed for post-spatial-reconstruction material decomposition of multi-energy CT datasets. The material decomposition used in this program is a version of the CMD algorithm that has been modified to separate the dense material and soft tissue problems and to apply the volume fraction conservation constraint to the soft tissue problem.

The separation of the soft tissue and dense material problems aid material decomposition by preventing noise in the soft tissue voxels being incorrectly decomposed into dense materials. As a consequence of this improvement, any low concentrations of dense materials whose signal is very close to or in the noise level will be selectively represented as soft tissue instead of dense material. However, this is not an issue if this cut-off concentration is close to the detection limit for the multi-energy CT scanner acquiring the data.

The mass attenuation coefficients for lipid and water are virtually identical for x-rays above 50 keV, where these x-rays contribute the majority of the signal measured in the human imaging range. Since lipid and water are immiscible, the relationship between conservation of volume fractions and linear attenuation intensity of soft tissues can hold more useful information than the multi-energy measurement by itself. This is illustrated in the addition of volume conservation to the soft tissue decomposition in the MARS-MD algorithm producing a more sensible result than the CMD algorithm.

It has been shown that the MARS-MD algorithm can easily achieve a reasonable six material decomposition using 4 energy bands in the human imaging range.

The computer implemented methods of the present invention may be operated using the systems as exemplified in FIGS. 21A and 21B.

In use the system 300 of FIG. 21A includes a multi-energy CT imaging system 301. Multi-energy CT images are taken of an object/sample or patient of interest and the image data set delivered via communications network 302 to computer system 303. Computer system 303 includes processor 304, data storage medium 305 and server 306.

Processor 304 receives the image data set from communications network 302 and implements the processing steps of the methods of the present invention together with data storage medium 305. Server 306 serves data from computer system 303 to interface 307.

Interface 307 may be an application program interface (API), a user interface, software or hardware interface.

FIG. 21B shows an alternate system 600 of the present invention, where multi-energy CT image data is received over a communications network 602 by a processor 604 within computer system 603. Multi-energy CT data is received over communications network 602 from an external source via known communications protocols for example, email, internet, FTP or HTML.

As with system 300 computer system 603 includes processor 604, data storage medium 605 and server 606. Processor 604 receives the image data set from communications network 602 and implements the processing steps of the methods of the present invention together with data storage medium 605. Server 606 serves data from computer system 603 to interface 607.

Interface 607 may be an application program interface (API), a user interface, software or hardware interface for example.

The various operations of methods described above may be performed by any suitable means capable of performing the operations, such as various hardware and/or software component(s), circuits, and/or module(s). Generally, any operations illustrated in the Figures may be performed by corresponding functional means capable of performing the same or equivalent operations.

The various illustrative modules and algorithm steps described in connection with the embodiments disclosed herein may be implemented as electronic hardware, computer software, or combinations of both. To clearly illustrate this interchangeability of hardware and software, various illustrative components, modules, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the embodiments of the invention.

The steps of a method or algorithm and functions described in connection with the embodiments disclosed herein may be embodied directly in hardware, in a software module executed by a processor, or in a combination of the two. If implemented in software, the functions may be stored on or transmitted over as one or more instructions or code on a tangible, non-transitory computer-readable medium.

A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD ROM, or any other form of storage medium known in the art.

A storage medium is coupled to the processor such that the processor can read information from, and write information to, the storage medium. In the alternative, the storage medium may be integral to the processor. Disk and disc, as used herein, includes compact disc (CD), laser disc, optical disc, digital versatile disc (DVD), floppy disk and blu ray disc where disks usually reproduce data magnetically, while discs reproduce data optically with lasers.

Combinations of the above should also be included within the scope of computer readable media. The processor and the storage medium may reside in an ASIC. The ASIC may reside in a user terminal. In the alternative, the processor and the storage medium may reside as discrete components in a user terminal.

The success of the MARS-MD algorithm can be contributed to the following three aspects: it searches for sparse solutions; the combinatorial nature of the algorithm which allows simple application of constraints to specific material combinations; and it prevents dense materials being allocated to low attenuating regions by segmenting the problem into two independent problems.

The MARS-MD algorithm in combination with multi-energy x-ray scanning as discussed above has a wide range of applications, both medical and otherwise. As would be appreciated by a person skilled in the art, the algorithms associated with MARS-MD may be added, modified or used in a single-step analysis with spatial reconstruction techniques in order to perform effectively for particular applications. Those skilled in the art will recognise that iterative methods of performing spatial reconstruction can be interwoven with the algorithms and methods described here, and such iterative methods will give rise to more rapid, and better material quantification, as the beam hardening artefacts that arise from the width of the energy ranges will be handled by such methods. However, the core methods performed by the algorithm will essentially remain unchanged. Some of those applications are discussed in further detail below in general terms which are non-intended to be limiting.

Unless otherwise stated, the use of the MARS-MD algorithm in conjunction with multi-energy x-ray technology, either alone or in conjunction with other methods, for material identification and quantification is assumed in each application. It should also be assumed that all methods relating to human or animal diagnosis or monitoring include both alive and deceased subjects, or tissue samples therefrom.

Where the below applications utilise the methods of the present invention or parts thereof, they are intended for use as computer implemented methods, utilising the systems and apparatus described above, or parts thereof.

Atherosclerosis Imaging

Atherosclerosis is an inflammatory disease which results in narrowing and hardening of the vascular system through the formation of atherosclerotic plaques, or atheromas in the arterial wall. These plaques are characterised by a lipid build up (lipid core) and calcifications (in older plaques). If an atherosclerotic plaque is unstable then it has the possibility of rupturing, causing heart attack, stroke or infarction and potentially death.

The methods described herein may be applied to multi-energy x-ray data to spatially locate and quantify components of atheroma plaque that indicate the plaque is unstable or vulnerable. The method may also be used to monitor the plaque serially over time with or without treatment to determine whether the plaque is becoming more or less vulnerable.

The use of the current methods in atheroma imaging allows in vivo "histology" of atheroma, and drug discovery for stabilising vulnerable atheroma plaque. Vulnerable or unstable in this context means a piece of plaque is likely to break off from the vessel wall and block a critical vessel downstream causing complications such as heart attack or stroke or infarction unless it is stabilized. The site of atheroma may be anywhere in the body—the carotid and coronary arteries are the sites for atheroma causing stroke and heart attack.

The specific components of vulnerable plaque that may be identified and quantified using multi-energy x-ray imaging include inflammatory cells such as monocytes and macrophages; lipid core; fibrous cap; haemorrhage (bleeding) within plaque and/or new vessels within plaque. This list is not intended to be limiting and other cell, tissue or material may also be quantified and identified.

The different components may be targeted with a nanocontrast agent comprising a nanoparticle of any shape, for example nanorods, based on metals such as gold, gadolinium, iodine, hafnium, tantalum, bismuth, ytterbium, platinum, yttrium, rubidium for example, that are coated with a material to make them safe to administer. Often a biologically active component such as a ligand or antibody or part of an antibody that will specifically bind to a specific cell surface marker, or be incorporated into a specific cell or tissue, with or without an accompanying pharmaceutical attached will also be incorporated. The nanocontrast agent may be delivered by injection, topical application, or incorporated within an implantable device or scaffold such as a metal or biological stent or other drug delivery system.

The quantification of the material (e.g. lipid, macrophages, fibrous tissue) is based on either measuring the tissue directly, or measuring the nanoparticle contrast marker tagged to that tissue. For nanocontrast agents, the quantification involves a calibration step where different but known concentrations of the metal (gold, gadolinium, iodine etc.) are imaged, Hounsfield units (HU) plotted against energy, and a calibration curve expressed as HU on x-axis, and concentration expressed in mg/ml or µg/µL is generated.

The energy related HU spectrum of the specific nanocontrast agent in the plaque is determined, and the concentration or amount of the nanocontrast at each spatial location is determined from the calibration curve.

The inventors have found that using the methods of the current invention, five or more different target components of the plaque, including drug delivery, can be measured from a single 3D volume scan. The quantification of drug delivery to the atheroma site can be obtained in the same way by combining the drug or pharmaceutical to the nanocontrast agent or separately labelling the drug with a metal marker (gold, gadolinium, iodine etc.).

The method may be applied to excised tissue samples, euthanized animals, live animals or humans. By repeating imaging at different time points in small animal models (mice, rats, rabbits etc.) or large animal models (pigs, sheep, deer, primates), or in humans, the inflammatory response can be monitored, allowing opportunities to modify treatments based on knowledge of the inflammatory process occurring in situ at each time point.

In use, multi-energy CT using MARS-MD material decomposition has been used for identifying signs of instability in atherosclerotic plaque. Material decompositions from two different studies are discussed below: identifying intrinsic plaque structure (without contrast) for categorising instability; and using targeted gold nano-particles to identify unstable thrombotic regions of plaque. All imaging has been done on excised atherosclerotic plaque.

The purpose of locating thrombotic regions inside a plaque is that they typically occur in unstable plaque, and therefore the number of thrombi can be used as a measure of plaque vulnerability.

Material decomposition in this work was used to distinguish regions of concentrated gold (at sites of thrombosis) from the calcifications which occur inside plaques.

Figure 25:
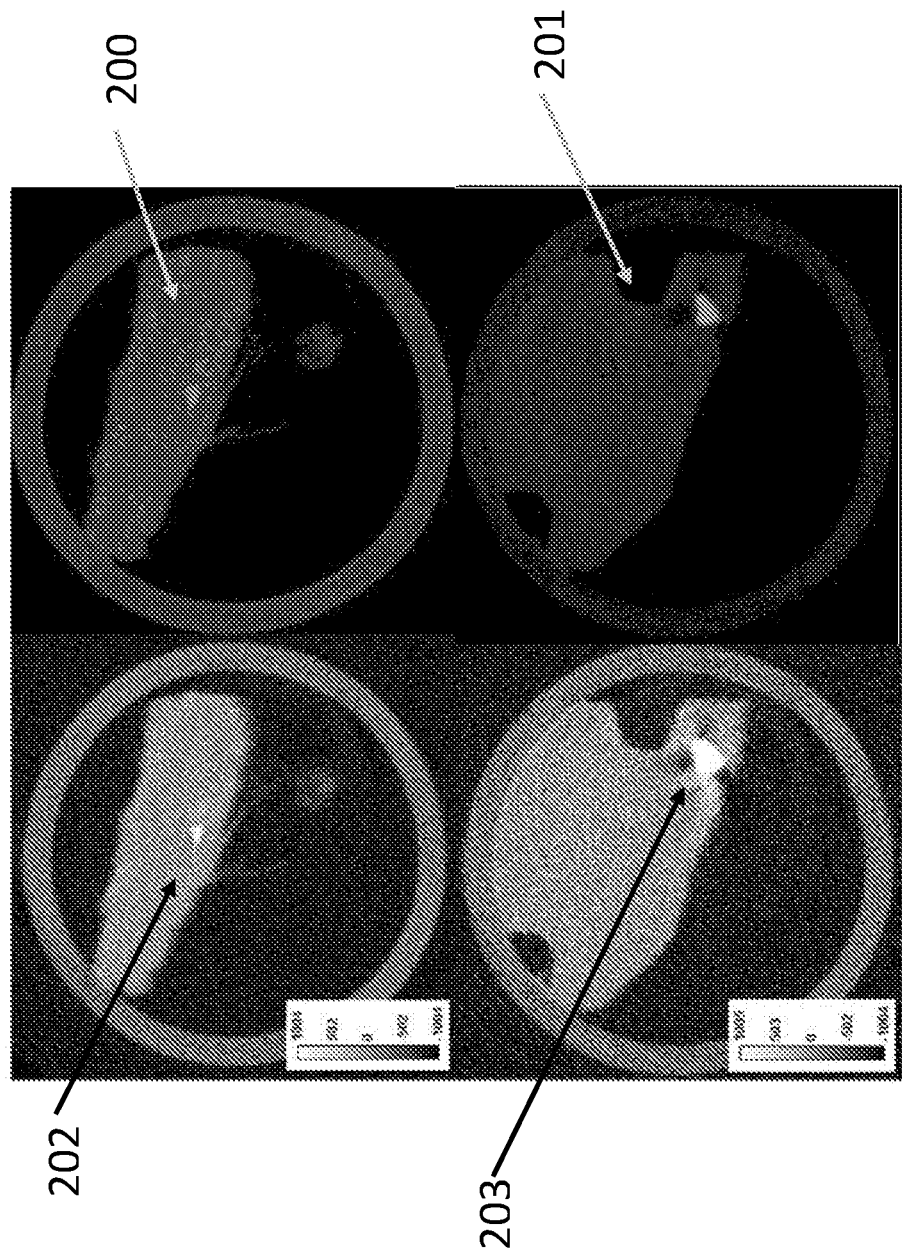
FIG. 25 shows material decomposition images of an atherosclorosis plaque.

Shaded material decomposition images of a plaque from this study are shown in FIG. 25, where image 200 shows a region where gold is attached to thrombosis in the plaque, whereas the image 201 shows a large calcification inside the plaque. Reconstructed Hounsfield unit images 202 and 203 are provided on the left hand side which show that the gold nano-particles at the thrombosis site and the calcification are indistinguishable in a standard CT scan. The data used for this material decomposition was collected using a CdTe-Medipix-2 (CdTe) MXR detector; 120 kVp tungsten x-ray beam; and measured using four energy bands (10-120, 25-120, 55-120 and 83-120 keV).

Studies using multi-energy CT to image atherosclerotic plaques without contrast pharmaceuticals were performed to identify the intrinsic structure of plaques (i.e. distribution of lipid core and calcifications) using multi-energy CT and find what correlations exist between the structure measurable by a multi-energy CT scanner and plaque vulnerability.

Figure 26:
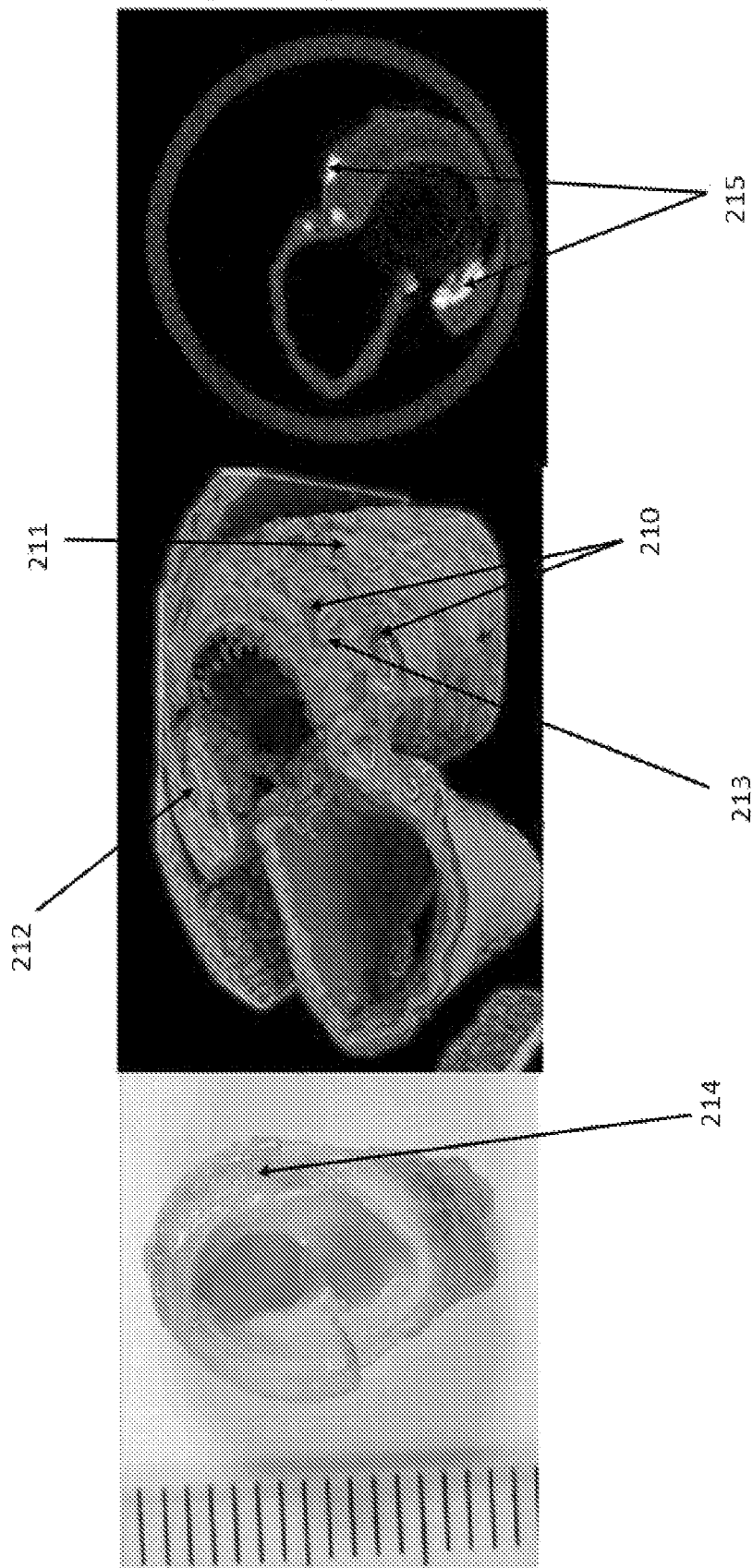
FIG. 26 shows a photo of atherosclerotic plaque prior to scanning, 3D material decomposition image of plaque, and reconstructed Hounsfield unit image of plaque.

A 3D material decomposition image generated using the material decomposition methods of the present invention of a plaque from a carotid artery is shown in FIG. 26. The different materials are indicated by different shaded areas, water 210, lipid 211 and calcium 212. The lipid core 213 in the plaque is visible in the decomposition image and can be matched to the lipid core 214 seen in the photo taken of the plaque prior to scanning. Calcifications 215 are shown in both the decomposed and reconstructed images that many calcifications are present in the plaque.

Bone Densitometry and Bone Health

Bone physiology is a dynamic process. Abnormalities of bone turnover are reflected in bone densitometry of the part of the bone nearest or involved in the disease process. For instance, the part of the bone near an inflamed joint becomes porotic (reduced density), cancer in bone can either increase or decrease the bone density and change the bone architecture and fracture risk increases in women with post-menopausal osteoporosis.

The methods of the present invention may be used to determine bone densitometry for any part of any bone by measuring the regional calcium hydroxyapatite concentration in situ. This is achieved by measuring the energy dependent Hounsfield units in the volume of bone of interest, reading the corresponding hydroxyapatite concentration from a calibration curve derived from measuring energy dependent Hounsfield units in a reference set of known concentrations of hydroxyapatite.

Using the methods of the present invention, bone densitometry can be measured at the same time as other features of bone health such as trabecular thickness, orientation and spacing, as well as cartilage health of the bone close to a joint; or assessment of cancer within bone; or infection or inflammation of bone or adjacent cartilage.

Exemplary imaging of osteoarthritic cartilage has also been undertaken using the methods of the present invention. In one example of this application excised cartilage samples were scanned in combination with an iodine contrast (Hexabrix) which has the property that it is drawn into osteoarthritic tissue. The purpose of this investigation was to develop a non-invasive method for diagnosing severity of osteoporosis arthritis.

The data used in the following material decomposition can be seen in FIGS. 27 and 28. The scan is of an excised arthritic human tibial plateau which has been incubated in an iodine contrast (Hexabrix) solution. The data was collected using a CdTe-Medipix-3RX (CdTe) detector; 80 kVp tungsten x-ray beam; and measured using four energy bands (20-80, 28-80, 30-80, and 40-80 keV).

Figure 27:
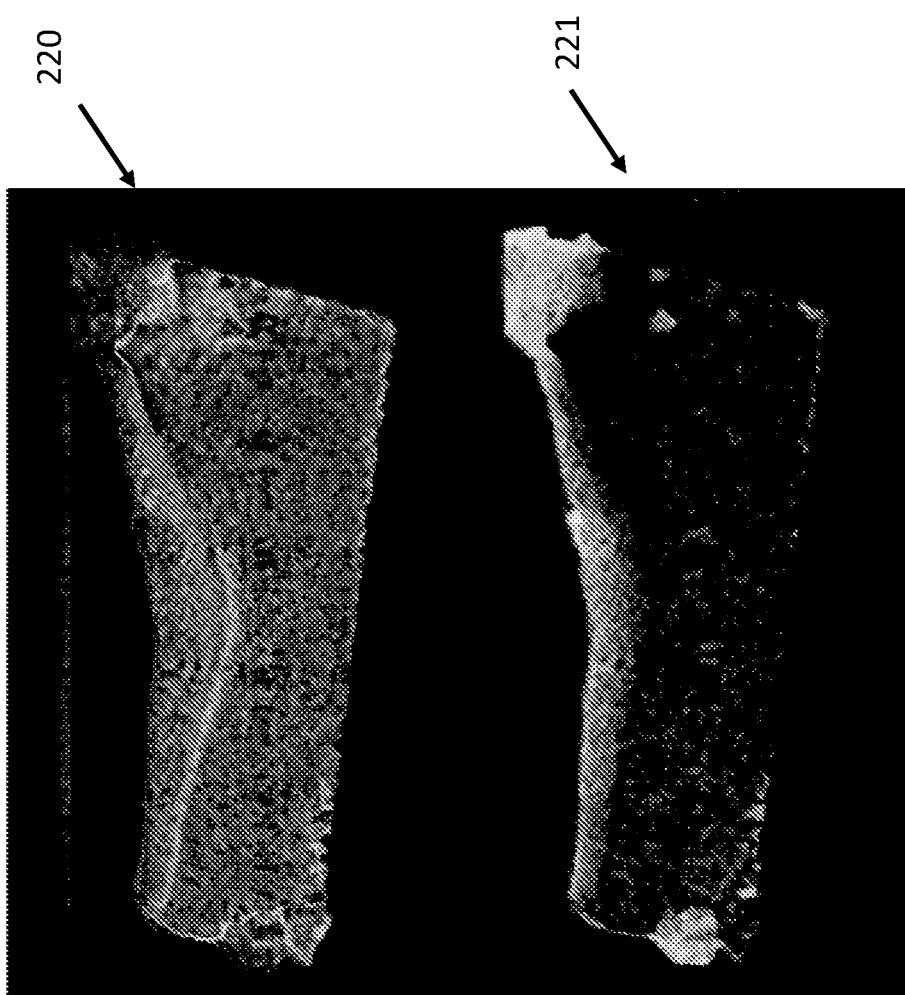
FIG. 27 shows a reconstructed Hounsfield unit image and material decomposition images of an excised arthritic human tibial plateau incubated in iodine contrast.
Figure 28:
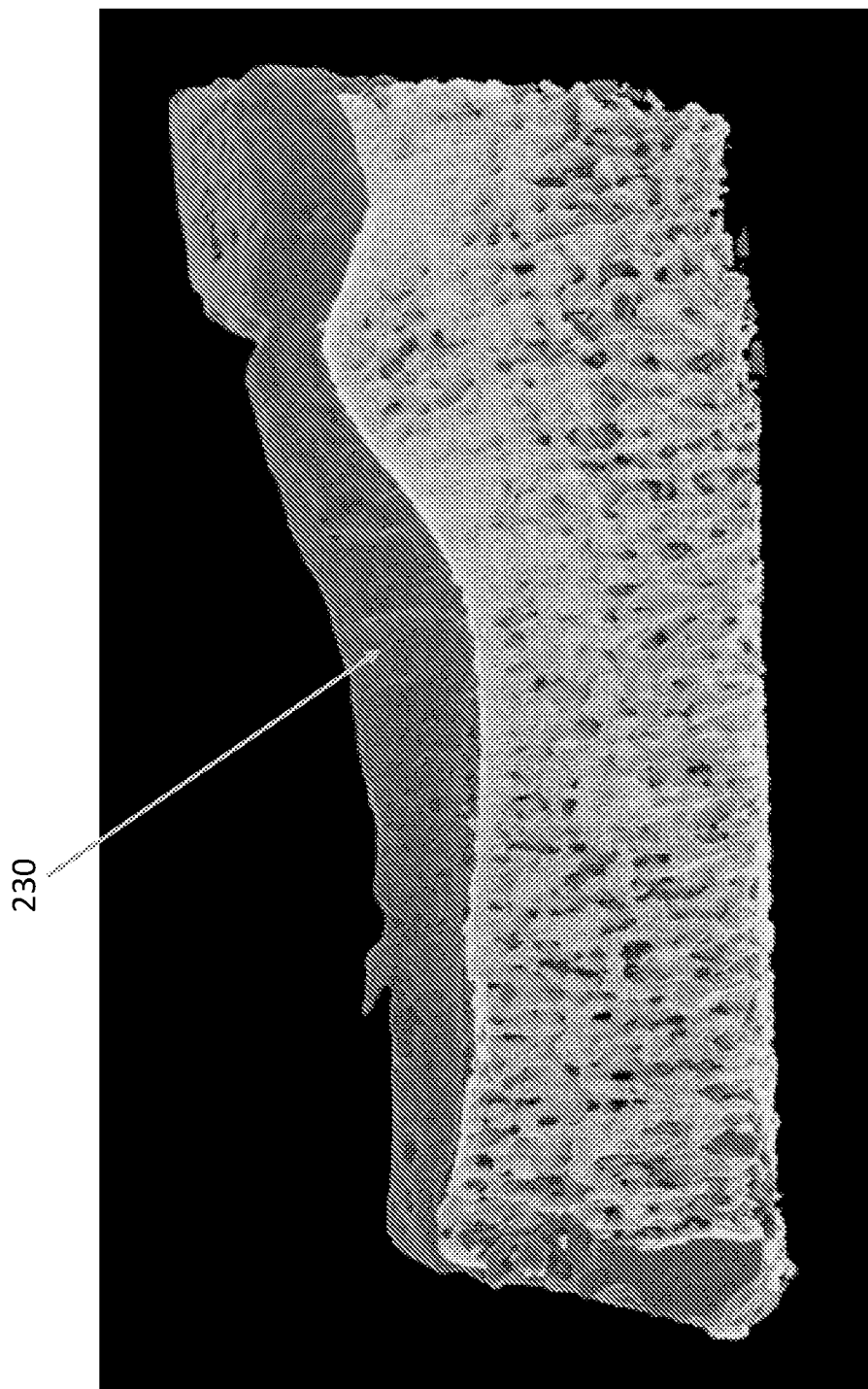
FIG. 28 shows a 3D material decomposition image of an excised arthritic human tibial plateau incubated in iodine contrast.
Figure 29:
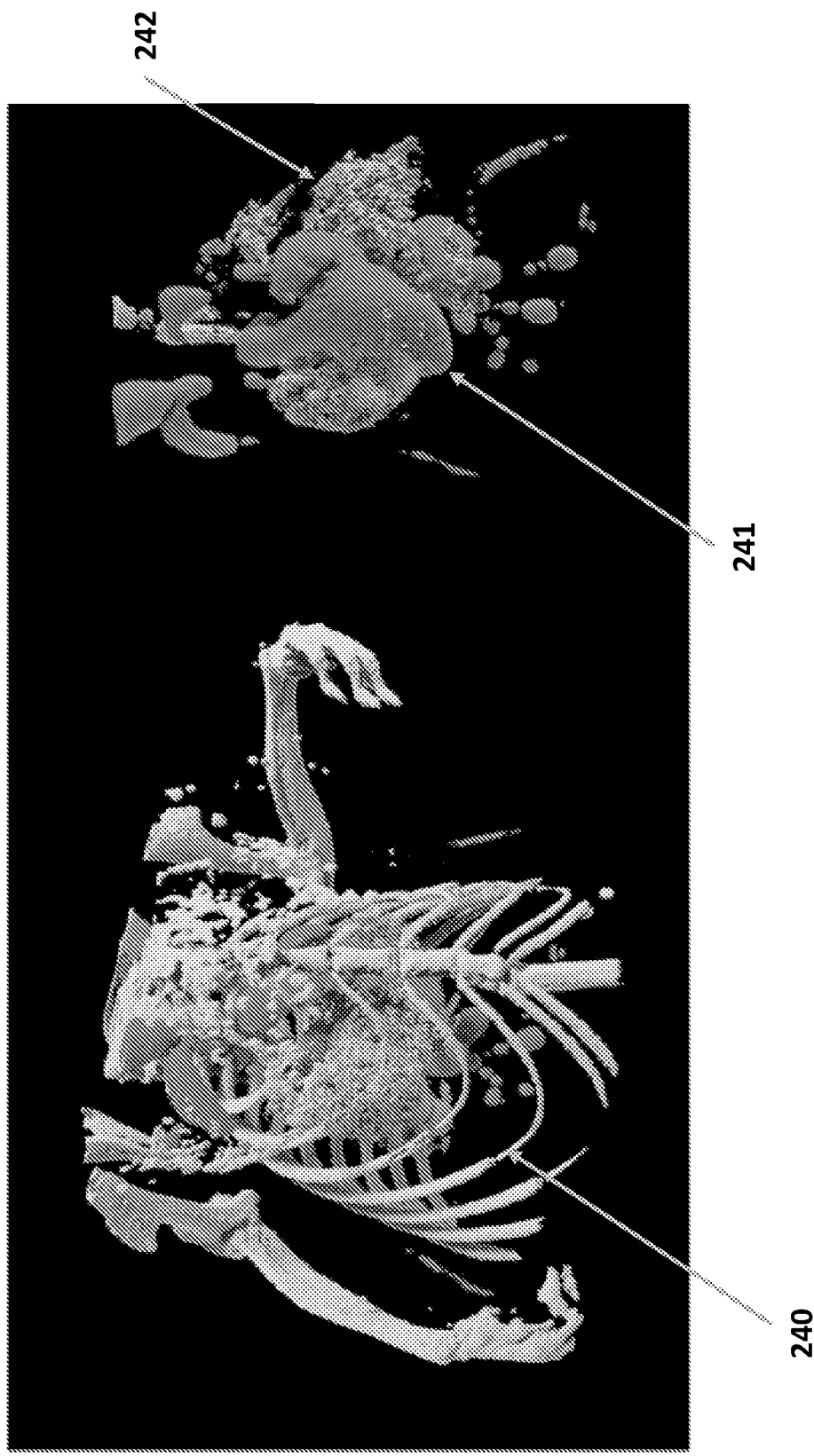
FIG. 29 shows a 3D material decomposition of "Mouse 12" dataset reprocessed using the methods of the present invention.

In the material decomposition images in FIG. 27 it can be seen when comparing the water image 220 and iodine image 221 that the iodine contrast has penetrated into the cartilage. The 3D material decomposition image in FIG. 28 shows a region where iodine contrast 230 penetrates the cartilage effectively reaching the bone underneath, thereby showing a region of severe arthritis.

Joint and Cartilage Imaging

The methods of the present invention can be used to extract molecular information relating to an ionic contrast agent and bone from an anatomical joint. The extracted signal will be of the material type and density that can be used to classify disease processes such as osteoarthritis (OA). The method provides molecular and functional information at high spatial resolution suitable for imaging of thin cartilage layers found in articulating surfaces of synovial joints such as the knee, hip, shoulder, and small joints of the extremities.

In one possible example of use, the imaging method involves injecting an ionic contrast agent to the joint space and acquiring multi-energy images of the cartilage-subchondral interface. Ionic contrast agents of concentrations starting from 10 mg/cc can be used to achieve equilibrium partitioning between glycosaminoglycans (present in the extracellular matrix of the cartilage) and the ionic agent.

Anionic and cationic contrast agents can be used for the multi-energy imaging. Examples of currently approved anionic contrast agents include Hexabrix (iodine based) and Multihance (gadolinium based) for imaging, but the methodology may apply to any current or future anionic or cationic contrast agent containing an element which is identifiable and quantifiable on spectral imaging using the methods of the present invention.

Negatively charged GAG repels anionic contrast agents and attracts cationic contrast agents. With osteoarthritis exhibiting non-linear depletion of GAG along the cartilage depth, density quantification of contrast agents using the current methods provides a system to grade cartilage health. Reference concentrations of the contrast agent employed and hydroxyapatite are used as an input to the MARS-MD algorithm to segment and quantify the contrast agent and subchondral bone density. A volume preservation constraint can then be employed to classify single and/or a combination of materials within a volume element.

The MARS-MD algorithm with or without nanocontrast can be applied to the multi-energy x-ray data to measure collagen content in cartilage, fibrous tissue or bone.

One end result of the joint and cartilage imaging method described above is a grading system to determine cartilage health and onset of cartilage degeneration enabling early diagnosis of osteoarthritis. Each material volume extracted using the MARS-MD algorithm represents a tissue-type or contrast agent or combination of both, with density information as an additional dimension besides the existing spatial dimensions. The MARS-MD algorithm provides localisation (contrast density vs. cartilage depth) and quantification (contrast density vs. cartilage health) and is directly related to the disease process.

Subchondral bone density is influenced by osteoarthritis and osteoporosis, and can be measured using MARS-MD method of the present invention. The MARS-MD algorithm enables measurement and monitoring of cartilage health including evaluation of the effectiveness of current and future cartilage repair treatment strategies in any joint disease affecting cartilage health, principally primary or secondary osteoarthritis. By repeating imaging at different time points in small animal models (mice, rats, rabbits etc.) or large animal models (pigs, sheep, deer, primates), or in humans, the disease process can be monitored, allowing opportunities to modify treatments based on knowledge of the inflammatory process occurring in situ at each time point.

Cancer

The MARS-MD method can be applied to cancer imaging to detect, localize, and quantify biomarkers of specific cancers in situ, determine heterogeneity of tumour cell markers and how tumour marker expression changes over time, in order to personalise cancer treatment so it matches the biology of the cancer.

Quantifiable nanocontrast agents can be used to label specific tumour cell markers, and markers of the cellular immune response (macrophages, T cells, and other immune response cell types) at any tumour site. The application can be for any tumour or cancer in a human or animal (including but not limited to carcinoma, neural, endocrine, lymphoma/leukaemia, germ cell, sarcoma, blastoma) in any organ in the head, neck, chest, abdomen and limbs (including but not limited to gastrointestinal tract, urinary tract, respiratory tract, skin, blood, brain and nervous system, endocrine glands) at any age (foetus, neonate, infant, child, adult).

The nanocontrast agents suitable for use with current method for identifying or monitoring cancer are functionalised nanoparticles. These typically include—a metal core, a coating to make them safe to administer in the body, and a ligand or aptimer or other biologically active macromolecule which specifically targets a cell marker. Two or more, usually five or more, different target components of the cancer including drug delivery can be measured from a single 3D volume scan.

The quantification of drug delivery to the tumour site can be obtained in the same way by combining the drug or pharmaceutical with the nanocontrast agent or separately labelling the drug with a metal marker such as gold, gadolinium or iodine. The method may be applied to excised tissue samples, euthanized animals, live animals or humans. By repeating imaging at different time points in small animal models or large animal models, the efficacy or rate of incorporation or growth of the tissue types can be monitored and modified in the individual.

In a similar fashion, the MARS-MD method can identify and quantify markers of hypoxia in tumours, fibrotic components of tumour, and microcalcifications in tumours.

Inflammatory and Infectious Diseases

Inflammation is a key pathological process in many acute and chronic diseases including but not limited to infection, arthritides, atherosclerosis, dementia, diabetes, autoimmune diseases and many cancers. Inflammation may be present at any site in the head, neck, chest, abdomen, pelvis, limbs and extremities. The methods of the present invention in combination with the use of nanocontrast agents can be used to identify and quantify the components of the inflammatory process and immune response, including but not limited to neutrophils, lymphocytes, natural killer cells, T cells, B cells, innate lymphoid cells, thymocytes, granulocytes, monocytes, macrophages, fibroblasts, eosinophils, platelets, megakaryocytes and the precursors of these cells.

In the case of infection, the MARS-MD algorithm can be used to identify and quantify the pathogen (including but not limited to bacteria, mycobacteria, viruses, protozoa, fungi, worms and prions) causing infection on the image—a form of microscope without the need to cut up or remove any tissue from the body. This is especially useful for hard to diagnose infections, or infections not responding rapidly to treatment. The method involves using a range of different functionalised metal containing nanocontrast agents targeted to different potential pathogens and which could be quantified by a single multi-energy CT scan. Each nanocontrast is specifically targeted to a characteristic marker for the pathogen.

In the case of arthritis caused by crystals such as monosodium urate, calcium-pyrophosphate dihydrate, calcium hydroxyapatite, and calcium oxalate (diseases such as gout and pseudogout), the MARS-MD method can identify the type of crystal within the joint enabling faster and more specific treatment. Simultaneously, that is in the same multi-energy CT scan, the MARS-MD algorithm can be used to determine the severity of inflammation, response to treatment and drug delivery.

In the case of altered immune competence, MARS-MD may be used to monitor and measure the reduction or increase in immune cells at sites of infection or other disease entities in the immunologically compromised individual.

The different components of the inflammatory/immune response may be targeted with a nanocontrast agent comprising a nanoparticle of any shape, for example nanorods based on metals such as gold, gadolinium, iodine, hafnium, tantalum, bismuth, ytterbium, platinum, yttrium, rubidium etc., coated with a material to make it safe to administer, and often a biologically active component such as a ligand or antibody or part of an antibody that will specifically bind to a specific cell surface marker, or be incorporated into a specific cell or tissue, with or without an accompanying pharmaceutical attached. The nanocontrast agent may be delivered by injection, topical application, or incorporated within an implantable device or scaffold such as a metal or biological stent.

Scaffolds and Engineered Tissues in Regenerative Medicine

A range of tissues can be engineered then placed in the body to help regeneration of body tissue or parts. This includes but is not restricted to bone, cartilage, nerve tissue, bladder, bowel, muscle, blood vessels). More complex structures such as liver or pancreas are known to be made by additive manufacturing techniques. Many of these engineered tissues start with a scaffold then cell or tissue types are grown in or on these scaffold before they are implanted.

Scaffolds may be metal, such as stainless steel, titanium, $TiAl_6V_4$, tantalum, cobalt chrome for example or organic (such as collagen, fibrin, hydrogel, gelatin, nanofibre, aerogel, bioglass, hydroxyapatite, chitosan for example) and they may be bioactive. They may be coated with growth factors or growth stimulators either biological or non-biological such as strontium, magnesium.

The methods of the present invention can be used to noninvasively determine the growth of the tissue in/on the scaffold, and to monitor the degree to which the engineered tissue is incorporating into the body.

The application of the MARS-MD algorithm to multi-energy x-ray data can be used to identify the scaffold and its components, and quantify the new tissue forming, and the resorption of the scaffold itself.

MARS-MD provides this identification and quantification in two ways. Firstly, by directly identifying the material such as the metal within a scaffold, or by identifying an agent eluting from a scaffold. Secondly, by targeting specific cell or tissue types with nanocontrast agents comprising a nanoparticle of any shape based on metals such as gold, gadolinium, iodine, hafnium, tantalum, bismuth, ytterbium, platinum, yttrium, rubidium etc., coated with a material to make it safe to administer, and often a biologically active component such as a ligand or antibody or part of an antibody that will specifically bind to a specific cell surface marker, or be incorporated into a specific cell or tissue, with or without an accompanying pharmaceutical attached.

The nanocontrast agent may be delivered by injection, topical application, or incorporated within the implantable scaffold or stent.

The quantification of the material is based on either measuring the tissue directly, or measuring the nanoparticle contrast marker tagged to that tissue.

The method may be applied to excised tissue samples, euthanized animals, live animals or humans. By repeating imaging at different time points in small animal models (mice, rats, rabbits etc.) or large animal models (pigs, sheep, deer, primates), or in humans, the region of interest can be monitored, allowing opportunities to modify treatment.

For orthopaedic and/or dental applications, the methods of the present invention can be used to determine the ingrowth of bone into an implant be measuring the bone quantity or density at the bone/implant interface. Many orthopaedic and dental implants in use today are formed with porous coatings or apertures within the implant surface to encourage osseointegration of healthy bone with the implant surface, stabilising the implant within the body. On insertion of an implant no bone ingrowth will be present at the bone/implant interface. By measuring the bone density and position over time using multi-energy CT with the MARS-MD techniques described herein, the progress of the bone integrating with the implant can be measured and used to help determine the success and progress of the implantation.

Similar measurements can also be used to determine implant failure or degeneration. By using the scanning methods and algorithms described herein, implants showing little or no connection between implant and bone at what should be the bone/implant interface can identify a failed or failing implant that will need revising. By conducting such measurements over a time period, the success or failure of implants can be monitored and patient treatment programmes can be managed more effectively to ensure positive outcomes.

Lipid Deposition

Intracellular lipid in the liver is a feature of the fatty liver disease-cirrhosis-hepatocellular carcinoma sequence. Quantification of fat within the liver, globally and regionally is useful in determining when, and how to prevent this sequence progressing. Multi-energy CT used with the MARS-MD algorithm may be used to quantify the lipid/fat directly by distinguishing it from water-like cells, and fibrous tissue.

Intra-tumoral fat is a feature of some benign and malignant tumours. Identifying it is very helpful in diagnosis of such tumours.

Multi-energy CT with the MARS-MD algorithm may be used to identify and quantify fat, whether intracellular or extracellular in any body organ or tissue anywhere in the head, neck, chest, abdomen, pelvis or limbs. In one example of the use in lipid quantification, as lipid is an integral part of myelinated nerve tissue in the brain and spinal cord, brain diseases which alter the amount of myelin, or which lead to displacement or destruction can be assessed.

Quantification of fat in tissue may also be used outside the medical field. Fat content in meat, particularly when mixed through the texture (for example marbling in steaks) is of prime interest to the entire "farm to plate" meat industry. Using techniques outlines above, the methods described herein may be used to measure and grade fat content and distribution within meat at any stage in the processing chain from live animal to carcass to final meat cut. The methods may be applied to any animal whether farmed or in the wild, including but not confined to sheep and lamb, pigs, cattle, deer, fish, and shellfish.

Measuring Permeability and Pore Size

As the liver becomes diseased, the pore size in the liver sieve changes; Multi-energy CT with the MARS-MD algorithm can be used to measure the permeability of blood vessels, the pore size of the liver sieve, the integrity of the blood brain barrier, renal etc. by using different nanomaterials each of a different size to measure the effective pore size.

New blood vessels in tumours tend to be leaky. This allows them to grow. Multi-energy x-ray scanning and the MARS-MD algorithm can assess neoangiogenesis in tumours and other diseases by measuring how much non-functionalised nanoparticle contrast persists in the extracellular space hours after intravascular injection.

In one embodiment the method involves using metal based nanoparticles coated so they can be transported through the blood stream safely. They can be attached to macromolecule drugs for site specific delivery. Each different nanoparticle is of a different size e.g. 15 nm, 50 nm, 100 nm, 200 nm.

After injection, the nanoparticles circulate. Those small enough to pass through the junctions between endothelial cells in the neovasculature will accumulate locally in the extracellular space. The larger nanoparticles continue to circulate and may be taken up by the reticuloendothelial system of the liver and spleen. The multi-energy imaging is performed at 12-36 or more preferably 18-24 hours after administration of the nanoparticles.

Measurement of the nanoparticle content at the site of interest using the MARS-MD algorithm quantifies the degree of angiogenesis. This can be monitored over time and in conjunction with treatment. Macromolecular drugs can be delivered to desired locations with leaky vessels in this way, and the drug delivery quantified.

Material Decomposition for Breast Imaging

Multi-energy CT scanning used with the MARS-MD algorithm can be used for identification and quantification of benign and malignant breast diseases. This may involve the use of a number of the applications described in more detail above, and includes imaging of fat in the breast and microcalcifications including distinguishing calcium oxalate from calcium hydroxyapatite. Nanocontrast agents targeted to specific breast tumour cell targets (including but not restricted to HER-2 and oestrogen receptors) with or without provision for targeted drug delivery may also be used for targeted imaging of breast tumours or tissues.

Drug Delivery

Toxic drugs can be delivered more safely to tumours, infection, and other disease sites if they are incorporated into larger structures such as macromolecules or micelles or liposomes. If the macromolecule or liposome also contains a nanoparticle/nanocontrast, then the MARS-MD algorithm can measure how much drug or pharmaceutical is delivered to the site of interest. This can be for active drugs within the macromolecule/micelle or pro-drugs which become activated at the target site. MARS-MD can be used for assessing not only drug delivery but assessing drug activation if activation involves cleaving the active component.

The active drug component is labelled with one nanoparticle, and the inactive component with a different nanoparticle. The MARS-MD algorithm identifies, distinguishes and measures both components. If both are together in the target area, then that measures prodrug delivery. If later only the active nanoparticle marker is measured, then the drug has been activated, and the inactive component metabolised.

Combination Scanning with PET or SPECT

Alternative scanning techniques such as PET or SPECT can be used to indicate a range of components within a body, for example residual sites of cancer after treatment. Multi-energy CT may be combined with PET or SPECT to further aid in the monitoring and quantification of such components.

In one example of use which is not intended to be limiting, a nanocontrast labelled drug may be administered to a patient and multi-energy CT scanning used with the MARS-MD algorithm used to determine if there is successful drug delivery to the residual tumour.

Simultaneous Contrast Imaging

Mice are a common test subject used in biomedical research for a variety of reasons including Size and reproduction speed. They are well understood and have many aspects similar to humans both physically and in their genetics. One application that mice are used for is simultaneous multiple contrast imaging. The high energy resolution of multi-energy CT and the MARS-MD algorithm enables discrimination of many different contrast pharmaceuticals simultaneously from soft tissue and bone. An advantage of multi-contrast imaging is that it opens up possibilities for functional imaging using targeted multi-contrast pharmaceuticals.

Mouse 12

"Mouse 12" is a dataset that has been previously published using a PCA material decomposition technique (N. Anderson et al. 2010 [25]) to show that both barium and iodine can be discriminated simultaneously in mice using multi-energy CT. Since this publication, the dataset has been reprocessed using the methods of the present invention and the results shown in FIG. 29.

This data was collected using a Si-Medipix-2MXR detector; 75 kVp tungsten x-ray beam; and measured using four energy bands (12-75, 23-75, 30-75, and 33-75 keV). The 3D material decomposition image shows three materials—bone 240, iodine 241 in the heart, and barium 242 in the lungs.

The methods of the present invention have a number of distinct advantages over the current known technology.

The inventors have developed a material decomposition algorithm which can discriminate between a large number of materials simultaneously. Three algorithms are disclosed: the statistical segmentation technique, combinatorial material decomposition, and the MARS-MD algorithm. By using these techniques the inventors have achieved a six-material decomposition using four energy bands which is a significant advancement over the current known art.

SST is designed to use multi-energy information to assist segmentation. It is demonstrated that using multiple energies enables images to be segmented at lower levels of SNR than if only a single energy is used.

Combinatorial material decomposition (CMD) is a method developed for finding sparse solutions to the post-spatial-reconstruction material decomposition problem. The solution for each voxel is calculated using each sub-matrix of the material matrix (with columns up to the maximum number of materials desired in the solution) and the best result is selected. The combinatorial nature of this approach enables non-physical solutions and material combinations to simply be rejected.

The inventors have further shown that the CMD algorithm is capable of decomposing dense materials into six materials. The CMD algorithm was compared to two basic material decomposition techniques, linear least squares and non-negative linear least squares, neither of which were are able to achieve the same degree of discrimination shown by the CMD algorithm.

The MARS-MD algorithm is an enhancement of the CMD algorithm using further constraints.

First the SST algorithm is used to identify voxels either containing soft tissue or dense material. Second is that a volume fraction conservation constraint is included in the soft tissue decomposition. These additional constraints both reduce the misidentification of low attenuating materials as dense materials and ensures that the solution for lipid and water are physically reasonable.

When used on the same dataset, the MARS-MD algorithm is shown to have far less material misidentification than the CMD algorithm. The only exception to this is for very low concentrations of dense materials which are identified as soft tissue due to the level of noise in the data.

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

For purposes of summarizing the disclosure, certain aspects, advantages and novel features of the inventions have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

Various modifications of the above described embodiments will be readily apparent, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

REFERENCES

[1] P. Sukovic and N. H. Clinthorne, "Basis material decomposition using triple-energy X-ray computed tomography," *Conference Record—IEEE Instrumentation and Measurement Technology Conference*, vol. 3, pp. 1615-1618, 1999.

[2] M. Firsching, D. Niederl¨ohner, T. Michel, and G. Anton, "Quantitative material reconstruction in CT with spectroscopic x-ray pixel detectors—A simulation study," in *IEEE Nuclear Science Symposium Conference Record*, vol. 4, pp. 2257-2259, 2007.

[3] H. Q. Le and S. Molloi, "Least squares parameter estimation methods for material decomposition with energy discriminating detectors," *Med. Phys.*, vol. 38, pp. 245-255, 2011.

[4] A. M. Alessio and L. R. MacDonald, "Quantitative material characterization from multi-energy photon counting CT," *Med. Phys.*, vol. 40(3), p. 031108, 2013.

[5] H. J. Vinegar and S. L. Wellington, "Tomographic imaging of three-phase flow experiments," *Review of Scientific Instruments*, vol. 58(1), pp. 96-107, 1987.

[6] X. Liu, L. Yu, A. Primak, and C. McCollough, "Quantitative imaging of element composition and mass fraction using dual-energy CT: Three-material decomposition," *Med. Phys.*, vol. 36, pp. 1602-1609, 2009.

[7] J. Wang, N. Garg, X. Duan, Y. Liu, S. Leng, L. Yu, E. L. Ritman, B. Kantor, and M. C. H., "Quantification of iron in the presence of calcium with dual-energy computed tomography (DECT) in an ex vivo porcine plaque model," *Phys. Med. Biol.*, vol. 56, pp. 7305-7316, 2011.

[8] H. Q. Le and S. Molloi, "Segmentation and quantification of materials with energy discriminating computed tomography: A phantom study," *Med. Phys.*, vol. 38(1), pp. 228-237, 2011.

[9] J. P. Ronaldson, R. Zainon, N. Scott, S. P. Gieseg, A. P. Butler, P. Butler, and N. G. Anderson, "Toward quantifying the composition of soft tissues by spectral CT with Medipix3," *Med. Phys.*, vol. 39, pp. 6847-6857, 2012.

[10] A. Rencher, *Methods of Multivariate Analysis*. John Wiley & Sons, Inc., 1995.

[11] "Tissue Substitutes in Radiation Dosimetry and Measurement," *International Commission on Radiological Units and Measurements, ICRU Report Issue* 44, 1989.

[12] https://w9.siemens.com/cms/oemproducts/home/x-ray-toolbox/spektrum/pages/default.aspx.

[13] M. Berger, J. Hubbell, S. Seltzer, J. Chang, J. Coursey, R. Sukumar, D. Zucker, and K. Olsen, "XCOM: Photon Cross Sections Database." http://www.nist.gov/pml/data/xcom/index.cfm.

[14] C. J. Bateman, J. McMahon, A. Malpas, N. de Ruiter, S. Bell, A. P. Butler, P. H. Butler, and P. F. Renaud, "Segmentation enhances material analysis in multi-energy CT: A simulation study," in *International Conference Image and Vision Computing New Zealand*, pp. 190-195, 2013.

[15] E. J. Candes and M. B. Wakin, "An introduction to compressive sampling: A sensing/sampling paradigm that goes against the common knowledge in data acquisition," *IEEE Signal Processing Magazine*, vol. 25, no. 2, pp. 21-30, 2008.

[16] R. Tibshirani, "Regression Shrinkage and Selection via the LASSO," *Journal of the Royal Statistical Society B*, vol. 58, no. 1, pp. 267-288, 1996.

[17] S. Chen, D. Donoho, and M. Saunders, "Atomic Decomposition by Basis Pursuit," *SIAM Review*, vol. 43, no. 1, pp. 129-159, 2001.

[18] N. D. Tang, N. De Ruiter, J. L. Mohr, A. P. H. Butler, P. H. Butler, and R. Aamir, "Using algebraic reconstruction in computed tomography," in *ACM International Conference Proceeding Series*, pp. 216-221, 2012.

[19] R. B. Zainon, *Spectral Micro-CT Imaging of Ex Vivo Atherosclerotic Plaque*. PhD thesis, University of Canterbury, New Zealand, 2012.

[20] R. Zainon, P. Ronaldson, A. Butler, and P. Butler, "Establishing a linear basis for quantifying material composition using spectral CT," in *In Proceedings of 2011 International Conference on Biomedical Engineering and Biotechnology* (BEB2011), IEEE, 2011.

[21] M. F. Walsh, S. J. Nik, S. Procz, M. Pichotka, S. T. Bell, C. J. Bateman, R. M. N. Doesburg, N. De Ruiter, A. I. Chernoglazov, R. K. Panta, A. P. H. Butler, and P. H. Butler, "Spectral CT data acquisition with Medipix3.1," *Journal of Instrumentation*, vol. 8, no. 10, 2013.

[22] N. G. Anderson and A. P. Butler, "Clinical applications of spectral molecular imaging: Potential and challenges," *Contrast Media and Molecular Imaging*, vol. 9, no. 1, pp. 3-12, 2014.

[23] R. Aamir, *Using MARS Spectral CT for Identifying Biomedical Nanoparticles*. PhD thesis, University of Canterbury, 2013.

[24] R. Aamir, A. Chernoglazov, C. J. Bateman, A. P. H. Butler, P. H. Butler, N. G. Anderson, S. T. Bell, R. K. Panta, J. L. Healy, J. L. Mohr, K. Rajendran, M. F. Walsh, N. De Ruiter, S. P. Gieseg, T. Woodfield, P. F. Renaud, L. Brooke, S. Abdul-Majid, M. Clyne, R. Glendenning, P. J. Bones, M. Billinghurst, C. Bartneck, H. Mandalika, R. Grasset, N. Schleich, N. Scott, S. J. Nik, A. Opie, T. Janmale, D. N. Tang, D. Kim, R. M. Doesburg, R. Zainon, J. P. Ronaldson, N. J. Cook, D. J. Smithies, and K. Hodge, "MARS spectral molecular imaging of lamb tissue: Data collection and image analysis," *Journal of Instrumentation*, vol. 9, no. 2, 2014.

[25] N. G. Anderson, A. P. Butler, N. J. A. Scott, N. J. Cook, J. S. Butzer, N. Schleich, M. Firsching, R. Grasset, N. de Ruiter, M. Campbell, and P. H. Butler, "Spectroscopic (multi-energy) colour CT distinguishes iodine and barium contrast in mice," *Eur. Radiol.*, vol. 20, pp. 2126-2134.

The invention claimed is:

1. A computer implemented method for identifying and/or quantifying a number of materials in an object using images produced by a multi-energy CT system using three or more energy bands using a computer program product, the method including the steps of;
    a) receiving a reconstructed or non-reconstructed multi-energy CT image data set produced using three or more energy bands in relation to an object;
    b) storing said data on a data storage medium;
    c) if data received in a) is non-reconstructed, processing the data using one or more reconstruction techniques to produce a data set of reconstructed voxels;
    d) comparing each voxel in the reconstructed data set to a reference set of material signal amplitude and noise properties stored on a data storage medium;
    e) classifying the voxels into air, low density or high density voxels;
    f) based on the determination of e), selecting a first material decomposition method to be applied to low density voxels and/or selecting a second material decomposition method to be applied to higher density voxels;
    g) applying a first material decomposition method to the low density voxels, the first material decomposition method including using volume constrained non-negative linear least squares to aid material identification; and/or
    h) applying a second material decomposition method to the high density voxels, the second material decomposition method including using an method that aids material identification by enforcing a sparse representation of the material composition for each voxel;
    i) identifying specific materials with the object based on the solutions from g) and h); and
    j) presenting material identification information to an interface.

2. The method of claim 1, wherein the method includes the further step of scanning an object using a multi-energy CT system to produce an image data set and the step of sending image data.

3. The method of claim 1, wherein the step of classifying voxels as air, low density or high density voxels includes comparing individual voxels to a reference distribution of a specific reference material using the Mahalanobis distance metric and Euclidian distance metric.

4. The method of claim 3, wherein the step of classifying voxels further includes the step of filtering the data to remove noise.

5. The method of claim 1 wherein the step of applying a second material decomposition method further includes the preliminary step of scanning an object using a multi-energy CT system using three or more energy bands to produce an image data set and sending the image data using a transmitter to be received at step a).

6. The method of claim 1, further comprising measuring drug penetration into animal tissue including the steps of;
    a) administering a nanocontrast agent targeted to drug to be identified within the tissue;
    b) scanning the tissue using a multi-energy CT scanner using three or more energy bands to produce an image data set;
    c) quantifying the drug within the tissue based on the image data.

7. The method of claim 1, further comprising monitoring or identifying the presence of, or changes in specific tissue, tissues or components in an animal or human including the steps of:
    a) scanning the tissue or component using a multi-energy CT scanner using three or more energy bands to produce an image data set;
    b) quantifying the tissue(s) or components of interest within the animal or human based on the image data;
    c) repeating steps a) and b) over a period of time to generate information identifying the presence of, or changes in specific tissue, tissues or components over time; and
    d) developing a treatment plan for the animal or human based on the information provided from step c).

8. The method of claim 1, further comprising determining bone and/or cartilage health in an animal or human including the steps of:
    a) scanning the bone and/or cartilage using a multi-energy CT scanner using three or more energy bands to produce an image data set;
    b) quantifying the bone and/or cartilage within the animal or human based on the image data.

9. The method of claim 1, further comprising identifying and/or quantifying biomarkers of specific cancers in an animal or human, including:
    a) scanning a tissue or region of interest in an animal or human using a multi-energy CT scanner using three or more energy bands to produce an image data set;
    b) identifying and/or quantifying biomarkers within the animal or human tissue based on the image data.

10. The method of claim 1, further comprising identifying and/or quantifying pathogens in an animal or human, including:
    a) scanning a tissue or region of interest in an animal or human using a multi-energy CT scanner using three or more energy bands to produce an image data set;
    b) identifying and/or quantifying pathogens within the animal or human tissue based on the image data.

11. The method of claim 1, further comprising determining the growth of tissue associated with an implanted scaffold or engineered tissue in an animal or human, including;
    a) scanning a tissue or region of interest in an animal or human using a multi-energy CT scanner using three or more energy bands to produce an image data set;
    b) identifying and/or quantifying the growth of tissue associated with an implanted scaffold or engineered tissue within the animal or human based on the image data.

12. The method of claim 1, further comprising identifying and/or quantifying intracellular or extracellular lipid in the body or an animal or human, including:
    a) scanning a tissue or region of interest in an animal or human using a multi-energy CT scanner using three or more energy bands to produce an image data set;
    b) identifying and/or quantifying intracellular or extracellular lipid within the animal or human based on the image data.

13. The method of claim 1, further comprising identifying and/or quantifying pore sizes in animal of human tissue, including:
    a) scanning a tissue or region of interest in an animal or human using a multi-energy CT scanner using three or more energy bands to produce an image data set;

b) identifying and/or quantifying pore sizes within tissue or region of interest in the animal or human based on the image data.

14. The method of claim 1, further comprising detecting and identifying benign and/or malignant breast diseases in an animal or human, including:
   a) scanning a tissue or region of interest in an animal or human using a multi-energy CT scanner using three or more energy bands to produce an image data set;
   b) identifying and/or quantifying benign and/or malignant breast diseases within tissue or region of interest in the animal or human based on the image data.

15. The method of claim 1, further comprising measuring activation of a pro-drug in an animal or human, including the steps of;
   a) labelling an active component of the pro-drug with a first nanocontrast agent;
   b) labelling an inactive component of the pro-drug with a second nanocontrast agent;
   c) administering the labelled pro-drug to the animal or human prior to imaging;
   d) performing a first scan of the target area in the animal or human using a multi-energy CT scanner using three or more energy bands to produce an image data set;
   e) determining the presence of and if present, measuring the inactive and active components of the pro-drug at the target area based on the image data;
   f) after a pre-determined period of time, performing a second scan of the target area in the animal or human using a multi-energy CT scanner using three or more energy bands, to produce a second image data set; and
   g) determining the presence of and if present, measuring the inactive and active components of the pro-drug at the target area based on the second image data;
   wherein the presence of the active component and absence of, or decrease in the quantity of the inactive component at step g) indicates drug activation.

16. The method of claim 1, further comprising identification or quantification of a component within, or excised from an animal or human, including the steps of;
   a) scanning the animal, human or part thereof using a PET or SPECT scanner to produce a visual image;
   b) using the results of step a), identifying a region of interest within the animal or human;
   c) administering a nanocontrast agent to the animal or human targeted to the region of interest or drug to be delivered to that region;
   d) scanning the animal or human using a multi-energy CT scanner using three or more energy bands to produce an image data set; and
   e) quantifying the nanocontrast agent based on the image data.

17. A system for identifying and presenting a number of different materials represented by data produced by a multi-energy CT system using three or more energy bands, the system comprising:
   a) a receiver for receiving a reconstructed or non-reconstructed multi-energy CT image data set in relation to an object;
   b) a data storage medium for storing said data;
   c) a processor for processing the data using one or more reconstruction techniques to produce a data set of reconstructed voxels;
   d) a processor for comparing each voxel in the reconstructed data set to a reference set of material signal amplitude and noise properties stored on a data storage medium;
   e) a processor for classifying the voxels into air, low density or high density voxels;
   f) a processor for selecting a first material decomposition method to be applied to low density voxels and/or selecting a second material decomposition method to be applied to higher density voxels;
   g) a processor for applying a first material decomposition method to the low density voxels, the first material decomposition method including using volume constrained non-negative linear least squares to aid material identification; and/or
   h) a processor for applying a second material decomposition method to the high density voxels, the second material decomposition method including using an method that aids material identification by enforcing a sparse representation of the material composition for each voxel;
   i) a processor for identifying specific materials with the object based on the solutions from g) and h); and
   j) an interface for presenting material identification information of step i).

18. The system of claim 17, wherein the system includes a multi-energy CT system using three or more energy bands for scanning an object to produce an image data set and a transmitter for sending image data to the receiver.

19. The method of claim 1, further comprising identification or quantification of one or more materials within, or excised from an animal or human, the method including the steps of;
   a) scanning the animal, human or part thereof using a multi-energy CT system using three or more energy bands to produce an image data set or receiving a multi-energy CT image data set produced using three or more energy bands for the animal, human or part thereof;
   b) quantifying or identifying the one or more materials based on the CT image data set.

20. The method of claim 19, wherein the material to be identified or quantified is selected from plaque, cancer, cancerous tumors or markers and biological identifiers thereof, components associated with the inflammatory process or infection, bone or cartilage, pathogens, crystals, lipids or fats.

21. The method as claimed in claim 19, wherein the method includes the step of administering a nanocontrast agent targeted to the material to be identified to the animal, human or part thereof prior to scanning.

* * * * *